US009999660B2

(12) United States Patent
Mueller et al.

(10) Patent No.: US 9,999,660 B2
(45) Date of Patent: Jun. 19, 2018

(54) TOLEROGENIC COMPOSITIONS COMPRISING AND USES THEREOF

(71) Applicants: UNIVERSITAT ZURICH, Zurich (CH); LEIDEN UNIVERSITY MEDICAL CENTER, Leiden (NL)

(72) Inventors: Anne Mueller, Dübendorf (CH); Daniela Engler-Anders, Zurich (CH); Christian Taube, Wassenaar (NL)

(73) Assignees: UNIVERSITAT ZURICH, Zurich (CH); LEIDEN UNIVERSITY MEDICAL CENTER, Leiden (NL)

( * ) Notice: Subject to any disclaimer, the term of this patent is extended or adjusted under 35 U.S.C. 154(b) by 0 days. days.

(21) Appl. No.: 15/115,377

(22) PCT Filed: Jan. 30, 2015

(86) PCT No.: PCT/IB2015/050703
§ 371 (c)(1),
(2) Date: Jul. 29, 2016

(87) PCT Pub. No.: WO2015/114575
PCT Pub. Date: Aug. 6, 2015

(65) Prior Publication Data
US 2017/0007683 A1    Jan. 12, 2017

(30) Foreign Application Priority Data
Jan. 31, 2014  (EP) .................................... 14153365

(51) Int. Cl.
A61K 39/00     (2006.01)
A61K 49/00     (2006.01)
A61K 39/38     (2006.01)
A61K 38/16     (2006.01)
A61K 39/02     (2006.01)
A61K 45/06     (2006.01)
C07K 14/205    (2006.01)

(52) U.S. Cl.
CPC .......... A61K 39/001 (2013.01); A61K 38/164 (2013.01); A61K 39/0208 (2013.01); A61K 45/06 (2013.01); C07K 14/205 (2013.01); A61K 2039/54 (2013.01); A61K 2039/542 (2013.01); A61K 2039/577 (2013.01)

(58) Field of Classification Search
CPC ...................................................... A61K 39/00
USPC .................. 424/9.1, 9.2, 184.1, 185.1, 234.1
See application file for complete search history.

(56) References Cited
U.S. PATENT DOCUMENTS
2017/0007649 A1    1/2017 Mueller et al.

FOREIGN PATENT DOCUMENTS

| EP | 1 582 215 | 10/2005 | |
|---|---|---|---|
| WO | WO 02/04017 | 1/2002 | |
| WO | WO03/018054 | * 3/2003 | ........... A61K 39/106 |
| WO | WO 03/018054 | 3/2003 | |
| WO | WO 2015/114576 | 8/2015 | |

OTHER PUBLICATIONS

Arnold, I.C. et al. "*Helicobacter pylori* infection prevents allergic asthma in mouse models through the induction of regulatory T cells" *The Journal of Clinical Investigation*, Aug. 2011, pp. 3088-3093, vol. 121, No. 8.
Arnold, I.C. et al. "Tolerance Rather Than Immunity Protects From *Helicobacter pylori*-Induced Gastric Preneoplasia" *Gastroenterology*, Jan. 2011, pp. 199-209 and 209.e1-209.e8, vol. 140, No. 1.
Bhaduri, S. et al. "Simple and Rapid Method for Disruption of Bacteria for Protein Studies" *Applied and Environmental Microbiology*, Oct. 1983, pp. 941-943, vol. 46, No. 4.
Chen, Y. et al. "Inverse Associations of *Helicobacter pylori* With Asthma and Allergy" *Arch Internal Medicine*, Apr. 23, 2007, pp. 821-827, vol. 167.
Chen, Y. et al. "*Helicobacter pylori* colonization is inversely associated with childhood asthma" *Journal of Infectious Diseases*, Aug. 15, 2008, pp. 553-560, vol. 198, No. 4.
Cover, T.L. et al. "Characterization of and Human Serologic Response to Proteins in *Helicobacter pylori* Broth Culture Supernatants with Vacuolizing Cytotoxin Activity" *Infection and Immunity*, Mar. 1990, pp. 603-610, vol. 58, No. 3.
Cover, T.L. et al. "Purification and Characterization of the Vacuolating Toxin from *Helicobacter pylori*" *The Journal of Biological Chemistry*, May 25, 1992, pp. 10570-10575, vol. 267, No. 15.
Cover, T.L. et al. "Acid-induced Dissociation of VacA, the *Helicobacter pylori* Vacuolating Cytotoxin, Reveals Its Pattern of Assembly" *The Journal of Cell Biology*, Aug. 25, 1997, pp. 759-769, vol. 138, No. 4.
DeBernard, M. et al. "The multiple cellular activities of the VacA cytotoxin of *Helicobacter pylori*" *International Journal of Medical Microbiology*, 2004, pp. 589-597, vol. 293.
Engler, D. et al. "Beneficial effects of early childhood *Helicobacter pylori* infection on the development of allergic and chronic inflammatory disorders" #197, *Allergy*, 2012, p. 93, vol. 67, Suppl. 96.
Engler, D. et al. "Effective treatment of allergic airway inflammation with *Helicobacter pylori* immunomodulators requires BATF3-dependent dendritic cells and IL-10" *Proceedings of the National Academy of Sciences*, Aug. 12, 2014, pp. 11810-11815, vol. 111, No. 32.
Fischer, W. et al. "Novel activities of the *Helicobacter pylori* vacuolating cytotoxin: from epithelial cells towards the immune system" *International Journal of Medical Microbiology*, 2004, pp. 539-547, vol. 293, No. 7-8.
Gangwer, K.A. et al. "Crystal structure of the *Helicobacter pylori* vacuolating toxin p55 domain" *Proceedings of the National Academy of Sciences*, Oct. 9, 2007, pp. 16293-16298, vol. 104, No. 41.

(Continued)

*Primary Examiner* — Rodney P Swartz
(74) *Attorney, Agent, or Firm* — Saliwanchik, Lloyd & Eisenschenk

(57) ABSTRACT

The present invention is directed to polypeptides and compositions thereof useful for the prevention and treatment of allergic disorders, in particular atopic asthma. More particularly, the invention relates to tolerogenic agents and compositions thereof that are useful for the prevention and treatment of hypersensitivity to allergens, in particular strategies of desensitization to allergens.

18 Claims, 18 Drawing Sheets

(56) References Cited

OTHER PUBLICATIONS

González-Rivera, C. et al. "Reconstitution of *Helicobacter pylori* VacA toxin from purified components" *Biochemistry*, Jul. 13, 2010, pp. 5743-5752, vol. 49, No. 27.

Harris, P.R. et al. "*Helicobacter pylori* Gastritis in Children Is Associated With a Regulatory T-Cell Response" *Gastroenterology*, 2008, pp. 491-499, vol. 134, No. 2.

Kelemen, M.V. et al. "Controlled Cell Disruption: A Comparison of the Forces Required to Disrupt Different Micro-Organisms" *Journal of Cell Science*, 1979, pp. 431-441, vol. 35.

Khinchi, M.S. et al. "Clinical efficacy of sublingual and subcutaneous birch pollen allergen-specific immunotherapy: a randomized, placebo-controlled, double-blind, double-dummy study" *Allergy*, Jan. 2004, pp. 45-53, vol. 59, No. 1.

Malfertheiner, P. et al. "Safety and Immunogenicity of an Intramuscular *Helicobacter pylori* Vaccine in Noninfected Volunteers: A Phase I Study" *Gastroenterology*, 2008, pp. 787-795, vol. 135, No. 3.

McClain, M.S. et al. "Essential Role of GXXXG Motif for Membrane Channel Formation by *Helicobacter pylori* Vacuolating Toxin" *The Journal of Biological Chemistry*, Apr. 4, 2003, pp. 12101-12108, vol. 278, No. 14.

Oertli, M. et al. "DC-derived IL-18 drives Treg differentiation, murine *Helicobacter pylori*-specific immune tolerance, and asthma protection" *The Journal of Clinical Investigation*, Mar. 2012, pp. 1082-1096, vol. 122, No. 3.

Oertli, M. et al. "*Helicobacter pylori* γ-glutamyl transpeptidase and vacuolating cytotoxin promote gastric persistence and immune tolerance" *Proceedings of the National Academy of Sciences*, Feb. 19, 2013, pp. 3047-3052 and supporting information pp. 1-7, vol. 110, No. 8.

Oertli, M. et al. "Dendritic cell-derived interleukin-18 drives regulatory T-cell differentiation and induces Helicobacter pylorispecific immune tolerance and asthma protection" *WIRM*, 2012, W27—poster abstract, p. 1.

Parsonnet, J. et al. "*Helicobacter pylori* Infection and the Risk of Gastric Carcinoma" *New England Journal of Medicine*, Oct. 17, 1991, pp. 1127-1131, vol. 325, No. 16.

Pfefferle, P.I. et al. "Microbial influence on tolerance and opportunities for intervention with prebiotics/probiotics and bacterial lysates" *Journal of Allergy Clinical Immunology*, Jun. 2013, pp. 1453-1463, vol. 131, No. 6.

Sayi, A. et al. "TLR-2-Activated B Cells Suppress *Helicobacter*-Induced Preneoplastic Gastric Immunopathology by Inducing T Regulartory-1 Cells" *The Journal of Immunology*, 2011, pp. 878-890, vol. 186.

Sun, J. et al. "Impact of DC40 Ligand, B Cells, and Mast Cells in Peanut-Induced Anaphylactic Responses" *The Journal of Immunology*, 2007, pp. 6696-6703, vol. 179.

Vinion-Dubiel, A.D. et al. "A Dominant Negative Mutant of *Helicobacter pylori* Vacuolating Toxin (VacA) Inhibits VacA-induced Cell Vacuolation" *The Journal of Biological Chemistry*, Dec. 31, 1999, pp. 37736-37742, vol. 274, No. 53.

Engler, D.B. et al. "Beneficial effects of early childhood Helicobacter pylori infection on the development of allergic and chronic inflammatory disorders" *WIRM*, 2012, P44—poster abstract, pp. 1-2.

Written Opinion in International Application No. PCT/IB2015/050703, dated May 7, 2015, pp. 1-7.

Huang, J.Q. et al. "Meta-Analysis of the Relationship Between cagA Seropositivity and Gastric Cancer" *Gastroenterology*, Dec. 2003, pp. 1636-1644, vol. 125, No. 6.

Luther, J.L. et al. "Association Between *Helicobacter pylori* Infection and Inflammatory Bowel Disease: A Meta-analysis and Systematic Review of the Literature" *Inflammatory Bowel Diseases*, Jun. 2010, pp. 1077-1084, vol. 16, No. 6.

Oertili, M. et al. "MicroRNA-155 Is Essential for the T Cell-Mediated Control of *Helicobacter pylori* Infection and for the Induction of Chronic Gastritis and Colitis" *The Journal of Immunology*, 2011, pp. 3578-3586, vol. 187.

Database BIOSIS [online], Accession No. PREV200600211957, "Helicobacter pylori extract upregulates PTEN and Cox2 in gastric epithelial cells: Implications for cell proliferation, survival and injury healing" May 2005, p. 1, XP-002739966.

Database WPI [online], Accession No. 2009-A66714, 2008, pp. 1-2, XP-002739965.

Koch, K. et al. "*Helicobacter* urease—induced activation of the TLR2/NLRP3/IL-18 axis protects against asthma" *The Journal of Clinical Investigation*, Aug. 2015, pp. 3297-3302, vol. 125, No. 8.

Koch, K. et al. "*Helicobacter pylori* activates the TLR2/NLRP3/caspase-1/IL-18 axis to induce regulatory T-cells, establish persistent infection and promote tolerance to allergens" *Gut Microbes*, Dec. 2015, pp. 382-387, vol. 6, No. 6.

Kyburz, A. et al. "*Helicobacter pylori* and Extragastric Diseases" *Current Topics in Microbiology and Immunology*, Molecular Pathogenesis and Signal Transduction by Helicobacter pylori, N. Tegtmeyer and S. Backert (eds.), 2017, pp. 325-347, vol. 400, Springer International Publishing.

Kyburz, A. et al. "*The Gastrointestinal Tract Microbiota and Allergic Diseases*" *Digestive Diseases*, 2016, pp. 230-243, vol. 34.

Djekic, A. et al. "The Immunomodulator VacA Promotes Immune Tolerance and Persistent *Helicobacter pylori* Infection through Its Activities on T-Cells and Antigen-Presenting Cells" *Toxins*, 2016, pp. 1-9, vol. 8, No. 187.

Engler, D. et al. "Helicobacter pylori—specific Protection Against Inflammatory Bowel Disease Requires the NLRP3 Inflammasome and IL-18" *Inflamm Bowel Dis*, 2015, pp. 1-8, vol. 21, No. 4.

ATCC product information for *Helicobacter pylori* (Marshall et al.) Goodwin et al. (ATCC 49503), 2016, pp. 1-2.

* cited by examiner

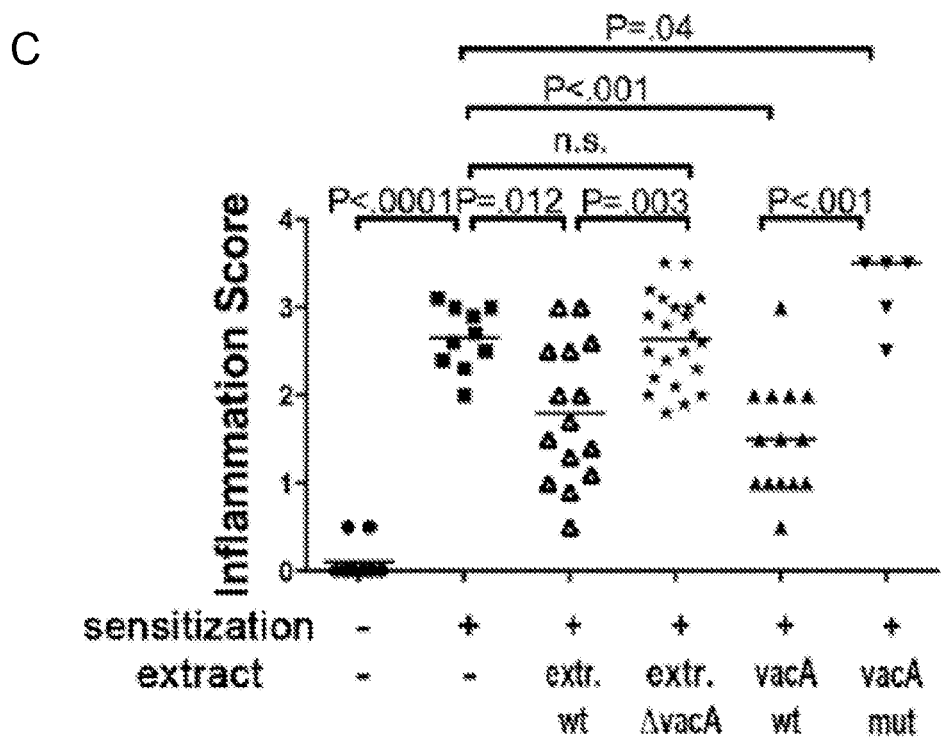
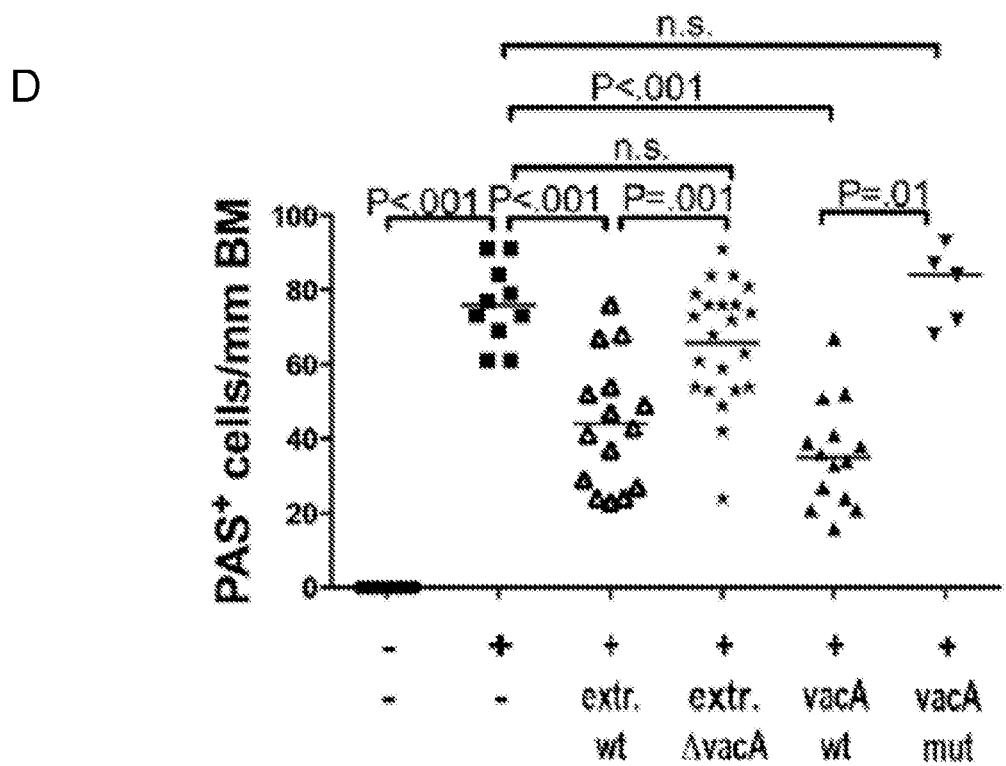
Figure 3 (continued)

A

**Q48245 *H. pylori* strain ATCC 49503/60190 (Cover et. al., 1994) (SEQ ID NO: 1)**

AFFTTVIIPAIVGGIATGTAVGTVSGLLGWGLKQAEEANKTPDKPDKVWRIQAGKGFNEFPN
KEYDLYKSLLSSKIDGGWDWGNAATHYWIKGGQWNKLEVDMKDAVGTYKLSGLRNFTGG
DLDVNMQKATLRLGQFNGNSFTSYKDSADRTTRVDFNAKNILIDNFLEINNRVGSGAGRKA
SSTVLTLQASEGITSSKNAEISLYDGATLNLASNSVKLNGNVVMGRLQYVGAYLAPSYSTIN
TSKVTGEVNFNHLTVGDHNAAQAGIIASNKTHIGTLDLWQSAGLNIIAPPEGGYKDKPNNTP
SQSGAKNDKQESSQNNSNTQVINPPNSTQKTEVQPTQVIDGPFAGGKDTVVNIDRINTKAD
GTIKVGGFKASLTTNAAHLNIGKGGVNLSNQASGRTLLVENLTGNITVDGPLRVNNQVGGYA
LAGSSANFEFKAGVDTKNGTATFNNDISLGRFVNLKVDAHTANFKGIDTGNGGFNTLDFSG
VTNKVNINKLITASTNVAVKNFNINELIVKTNGVSVGEYTHFSEDIGSQSRINTVRLETGTRSIF
SGGVKFKSGEKLVIDEFYYSPWNYFDARNIKNVEITRKFASSTPENPWGTSKLMFNNLTLGQ
NAVMDYSQFSNLTIQGDFINNQGTINYLVRGGKVATLNVGNAAAMMFNNDIDSATGFYKPLI
KINSAQDLIKNTEHVLLKAKIIGYGNVSTGTNGISNVNLEEQFKERLALYNNNNRMDTCVVRN
TDDIKACGMAIGNQSMVNNPDNYKYLIGKAWKNIGISKTANGSKISVYYLGNSTPTENGGNT
TNLPTNTTNNARFASYALIKNAPFAHSATPNLVAINQHDFGTIESVFELANRSKDIDTLYANS
GAQGRDLLQTLLIDSHDAGYARTMIDATSANEITKQLNTATTTLNNIASLEHKTSSLQTLSLSN
AMILNSRLVNLSRRHTNNIDSFAKRLQALKDQRFASLESAAEVLYQFAP

**s2m2 VacA from strain *H. pylori* Tx30a (*Atherton et al., 1995, J. Biol. Chem..***
B ***270 (30), 17771-17777*) (SEQ ID NO: 2)**

MEIQQTHRKINRPIISLALVGVLMGTELGANTPNDPIHSESRAFFTTVIIPAIVGGIATGAAVGT
VSGLLSWGLKQAEQANKAPDKPDKVWRIQAGRGFDNFPHKQYDLYKSLLSSKIDGGWDW
GNAARHYWVKDGQWNKLEVDMQNAVGTYNLSGLINFTGGDLDVNMQKATLRLGQFNGNS
FTSFKDGANRTTRVNFDAKNILIDNFVEINNRVGSGAGRKASSTVLTLKSSEKITSRENAEISL
YDGATLNLVSSSNQSVDLYGKVVMGRLQYVGAYLAPSYSTIDTSKVQGEMNFRHLAVGDQ
NAAQAGIIANKKTNIGTLDLWQSAGLSIITPPEGGYESKTKDNPQNNPKNDAQKTEIQPTQVI
DGPFAGGKDTVVNIFHLNTKADGTLRAGGFKASLSTNAAHLHIGEGGVNLSNQASGRTLLV
ENLTGNITVEGTLRVNNQVGGAAIAGSSANFEFKAGEDTNNATATFNNDIHLGKAVNLRVDA
HTANFNGNIYLGKSTNLRVNGHTAHFKNIDATKSDNGLNTSTLDFSGVTDKVNINKLTTAAT
NVNIKNFDIKELVVTTRVQSFGQYTIFGENIGDKSRIGVVSLQTGYSPAYSGGVTFKGGKKLV
IDEIYHAPWNYFDARNVTDVEINKRILFGAPGNIAGKTGLMFNNLTLNSNASMDYGKDLDLTI
QGHFTNNQGTMNLFVQDGRVATLNAGHQASMIFNNLVDSTTGFYKPLIKINNAQNLTKNKE
HVLVKARNIDYNLVGVQGASYDNISASNTNLQEQFKERLALYNNNNRMDTCVVRKDNLNDI
KACGMAIGNQSMVNNPENYKYLEGKAWKNTGINKTANNTTIAVNLGNNSTPTNSTTDTTNL
PTNTTNNARFASYALIKNAPFAHSATPNLVAINQHDFGTIESVFELANRSSDIDTLYANSGAQ
GRDLLQTLLIDSHDAGYARTMIDATSANEITQQLNAATTTLNNIASLEHKTSGLQTLSLSNAMI
LNSRLVNLSRKHTNHIDSFAKRLQALKDQRFASLESAAEVLYQFAPKYEKPTNVWANAIGGT
SLNNGSNASLYGTSAGVDAYLNGEVEAIVGGFGSYGYSSFSNQANSLNSGANNTNFGVYS
RIFANQHEFDFEAQGALGSDQSSLNFKSALLQDLNQSYHYLAYSATTRASYGYDFAFFRNA
LVLKPSVGVSYNHLGSTNFKSNSNQVALSNGSSSQHLFNANANVEARYYYGDTSYFYMNA
GVLQEFARFGSNNAVSLNTFKVNATRNPLNTHARVMMGGELQLAKEVFLNLGVVYLHNLIS
NASHFASNLGMRYSF

Figure 5

C   Negative control mutant (Δ6-27) VacA (SEQ ID NO: 3)

AFFTTLGWGLKQAEEANKTPDKPDKVWRIQAGKGFNEFPNKEYDLYKSLLSSKIDGGWD
WGNAATHYWIKGGQWNKLEVDMKDAVGTYKLSGLRNFTGGDLDVNMQKATLRLGQFNG
NSFTSYKDSADRTTRVDFNAKNILIDNFLEINNRVGSGAGRKASSTVLTLQASEGITSSKNA
EISLYDGATLNLASNSVKLNGNVWMGRLQYVGAYLAPSYSTINTSKVTGEVNFNHLTVGD
HNAAQAGIIASNKTHIGTLDLWQSAGLNIIAPPEGGYKDKPNNTPSQSGAKNDKQESSQNN
SNTQVINPPNSTQKTEVQPTQVIDGPFAGGKDTVVNIDRINTKADGTIKVGGFKASLTTNAA
HLNIGKGGVNLSNQASGRTLLVENLTGNITVDGPLRVNNQVGGYALAGSSANFEFKAGVD
TKNGTATFNNDISLGRFVNLKVDAHTANFKGIDTGNGGFNTLDFSGVTNKVNINKLITASTN
VAVKNFNINELIVKTNGVSVGEYTHFSEDIGSQSRINTVRLETGTRSIFSGGVKFKSGEKLVI
DEFYYSPWNYFDARNIKNVEITRKFASSTPENPWGTSKLMFNNLTLGQNAVMDYSQFSNL
TIQGDFINNQGTINYLVRGGKVATLNVGNAAAMMFNNDIDSATGFYKPLIKINSAQDLIKNTE
HVLLKAKIIGYGNVSTGTNGISNVNLEEQFKERLALYNNNRMDTCVVRNTDDIKACGMAI
GNQSMVNNPDNYKYLIGKAWKNIGISKTANGSKISVYYLGNSTPTENGGNTTNLPTNTTNN
ARFASYALIKNAPFAHSATPNLVAINQHDFGTIESVFELANRSKDIDTLYANSGAQGRDLLQ
TLLIDSHDAGYARTMIDATSANEITKQLNTATTTLNNIASLEHKTSSLQTLSLSNAMILNSRLV
NLSRRHTNNIDSFAKRLQALKDQRFASLESAAEVLYQFAP

D   **s1m1 VacA from strain *H. pylori* G27 (*Baltrus et al., 2009, J. Bacteriol., 191(1):447-8*) (SEQ ID NO: 4)**

MEIQQTHRKMNRPLVSLVLAGALISAIPQESHAAFFTTVIIPAIVGGIATGTAVGTVSGLLSWGL
KQAEEANKNPDKPDKVWRIQAGKGFNEFPNKEYDLYKSLLSSKIDGGWDWGNAARHYWVK
GGGQWNKLEVDMKDAVGTYKLSGLRNFTGGDLDVNMQKATLRLGQFNGNSFTSYKDAADR
TTRVNFNAKNISIDNFVEINNRVGSGAGRKASSTVLTLQASEGITSDKNAEISLYDGATLNLAS
SSVKLMGNVWMGRLQYVGAYLAPSYSTINTSKVTGEVNFNHLTVGDKNAAQAGIIASNKTHI
GTLDLWQSAGLNIIAPPEGGYKDKPNNTPSQSGTKNDKNESAKNDKQESSQNNSNTQVINP
PNSTQKTEIQPTQVIDGPFAGGKDTVVNINRINTNADGTIRVGGFKASLTTNAAHLHIGKGGV
NLSNQASGRTLLVENLTGNITVDGPLRVNNQVGGYALAGSSANFEFKAGVDTKNGTATFNN
DISLGRFVNLKVDAHTANFKGIDTGNGGFNTLDFSGVTDKVNINKLITASTNVAVKNFNINELI
VKTNGISVGEYTHFSEDIGSQSRINTVRLETGTRSIFSGGVKFKSGEKLVIDEFYYSPWNYFD
ARNVKNVEITRKFASSTPENPWGTSKLMFNNLTLGQNAVMDYSQFSNLTIQGDFINNQGTIN
YLVRGGKVATLSVGNAAAMMFNNDIDSATGFYKPLIKINSAQDLIKNTEHVLLKAKIIGYGNVS
TGTNSISNVNLEEQFKERLALYNNNRMDTCVVRNTDDIKACGMAIGNQSMVNNPDNYKYLI
GKAWKNIGISKTANGSKISVYYLGNSTPTENGGNTTNLPTNTTNNARSANYALVKNAPFAHS
ATPNLVAINQHDFGTIESVFELANRSKDIDTLYTHSGVQGRDLLQTLLIDSHDAGYARQMIDN
TSTGEITKQLNAATDALNNIASLEHKTSGLQTLSLSNAMILNSRLVNLSRKHTNHIDSFAQRLQ
ALKGQRFASLESAAEVLYQFAPKYEKPTNVWANAIGGASLNNGGNASLYGTSAGVDAYLNG
EVEAIVGGFGSYGYSSFSNRANSLNSGANNANFGVYSRIFANQHEFDFEAQGALGSDQSSL
NFKSALLQDLNQSYHYLAYSAATRASYGYDFAFFRNALVLKPSVGVSYNHLGSTNFKSSSN
QVALKNGSSSQHLFNANANVEARYYYGDTSYFYMNAGVLQEFARFGSNNAASLNTFKVNT
ARNPLNTHARVMMGGELQLAKEVFLNLGVVYLHNLISNIGHFASNLGMRYSF

Figure 5 (continued)

E **s1m1 VacA from strain *H. pylori* 60190 (*Cover et al., 1994, J. Biol. Chem., 269(14):10566-73*) (SEQ ID NO: 5)**

MEIQQTHRKINRPLVSLALVGALVSITPQQSHAAFFTTVIIPAIVGGIATGTAVGTVSGLLGWGL
KQAEEANKTPDKPDKVWRIQAGKGFNEFPNKEYDLYKSLLSSKIDGGWDWGNAATHYWIKG
GQWNKLEVDMKDAVGTYKLSGLRNFTGGDLDVNMQKATLRLGQFNGNSFTSYKDSADRTT
RVDFNAKNILIDNFLEINNRVGSGAGRKASSTVLTLQASEGITSSKNAEISLYDGATLNLASNSV
KLNGNVWMGRLQYVGAYLAPSYSTINTSKVTGEVNFNHLTVGDHNAAQAGIIASNKTHIGTLD
LWQSAGLNIIAPPEGGYKDKPNNTPSQSGAKNDKQESSQNNSNTQVINPPNSTQKTEVQPT
QVIDGPFAGGKDTVVNIDRINTKADGTIKVGGFKASLTTNAAHLNIGKGGVNLSNQASGRTLLV
ENLTGNITVDGPLRVNNQVGGYALAGSSANFEFKAGVDTKNGTATFNNDISLGRFVNLKVDA
HTANFKGIDTGNGGFNTLDFSGVTNKVNINKLITASTNVAVKNFNINELIVKTNGVSVGEYTHF
SEDIGSQSRINTVRLETGTRSIFSGGVKFKSGEKLVIDEFYYSPWNYFDARNIKNVEITRKFAS
STPENPWGTSKLMFNNLTLGQNAVMDYSQFSNLTIQGDFINNQGTINYLVRGGKVATLNVGN
AAAMMFNNDIDSATGFYKPLIKINSAQDLIKNTEHVLLKAKIIGYGNVSTGTNGISNVNLEEQFK
ERLALYNNNNRMDTCVVRNTDDIKACGMAIGNQSMVNNPDNYKYLIGKAWKNIGISKTANGS
KISVYYLGNSTPTENGGNTTNLPTNTTNNARFASYALIKNAPFAHSATPNLVAINQHDFGTIES
VFELANRSKDIDTLYANSGAQGRDLLQTLLIDSHDAGYARTMIDATSANEITKQLNTATTTLNNI
ASLEHKTSSLQTLSLSNAMILNSRLVNLSRRHTNNIDSFAKRLQALKDQRFASLESAAEVLYQF
APKYEKPTNVWANAIGGASLNNGGNASLYGTSAGVDAYLNGQVEAIVGGFGSYGYSSFNNQ
ANSLNSGANNTNFGVYSRIFANQHEFDFEAQGALGSDQSSLNFKSALLRDLNQSYNYLAYSA
ATRASYGYDFAFFRNALVLKPSVGVSYNHLGSTNFKSNSTNKVALSNGSSSQHLFNASANVE
ARYYYGDTSYFYMNAGVLQEFANFGSSNAVSLNTFKVNATRNPLNTHARVMMGGELKLAKE
VFLNLGVVYLHNLISNIGHFASNLGMRYSF

F **s1m1 VacA from strain *H. pylori* 26695 (*Tomb et al., 1997, Nature, 388(6642):539-47*) (SEQ ID NO: 6)**

MEIQQTHRKINRPLVSLALVGALVSITPQQSHAAFFTTVIIPAIVGGIATGAAVGTVSGLLGWG
LKQAEEANKTPDKPDKVWRIQAGKGFNEFPNKEYDLYRSLLSSKIDGGWDWGNAATHYWV
KGGQWNKLEVDMKDAVGTYNLSGLRNFTGGDLDVNMQKATLRLGQFNGNSFTSYKDSAD
RTTRVDFNAKNILIDNFLEINNRVGSGAGRKASSTVLTLQASEGITSSKNAEISLYDGATLNLA
SNSVKLMGNVWMGRLQYVGAYLAPSYSTINTSKVTGEVNFNHLTVGDHNAAQAGIIASNKT
HIGTLDLWQSAGLNIIAPPEGGYKDKPKDKPSNTTQNNANNNQQNSAQNNSNTQVINPPNS
AQKTEIQPTQVIDGPFAGGKDTVVNIDRINTNADGTIKVGGYKASLTTNAAHLHIGKGGINLSN
QASGRTLLVENLTGNITVDGPLRVNNQVGGYALAGSSANFEFKAGTDTKNGTATFNNDISLG
RFVNLKVDAHTANFKGIDTGNGGFNTLDFSGVTGKVNINKLITASTNVAVKNFNINELVVKTN
GVSVGEYTHFSEDIGSQSRINTVRLETGTRSIFSGGVKFKSGEKLVIDEFYYSPWNYFDARNI
KNVEITRKFASSTPENPWGTSKLMFNNLTLGQNAVMDYSQFSNLTIQGDFINNQGTINYLVR
GGQVATLNVGNAAAMFFSNNVDSATGFYQPLMKINSAQDLIKNKEHVLLKAKIIGYGNVSLG
TNSISNVNLIEQFKERLALYNNNNRMDICVVRNTDDIKACGTAIGNQSMVNNPDNYKYLIGKA
WKNIGISKTANGSKISVYYLGNSTPTEKGGNTTNLPTNTTSNVRSANNALAQNAPFAQPSAT
PNLVAINQHDFGTIESVFELANRSKDIDTLYANSGAQGRDLLQTLLIDSHDAGYARQMIDNTS
TGEITKQLNAATTTLNNIASLEHKTSSLQTLSLSNAMILNSRLVNLSRRHTNNIDSFAQRLQAL
KDQKFASLESAAEVLYQFAPKYEKPTNVWANAIGGTSLNNGGNASLYGTSAGVDAYLNGEV
EAIVGGFGSYGYSSFNNQANSLNSGANNTNFGVYSRIFANQHEFDFEAQGALGSDQSSLNF
KSALLRDLNQSYNYLAYSAATRASYGYDFAFFRNALVLKPSVGVSYNHLGSTNFKSNSNQV
ALKNGSSSQHLFNASANVEARYYYGDTSYFYMNAGVLQEFANFGSSNAVSLNTFKVNAAH
NPLSTHARVMMGGELKLAKEVFLNLGFVYLHNLISNIGHFASNLGMRYSF

Figure 5 (continued)

G  **s1m1 VacA of strain *H. pylori* J99 (*Merrell et al., 2003, Infect Immun., 71(11):6510-25*) (SEQ ID NO: 7)**

MEIQQTHRKINRPLVSLVLAGALISAIPQESHAAFFTTVIIPAIVGGIATGTAVGTVSGLLSWGL
KQAEEANKTPDKPDKVWRIQAGKGFNEFPNKEYDLYKSLLSSKIDGGWDWGNAARHYWV
KGGQWNKLEVDMKDAVGTYKLSGLRNFTGGDLDVNMQKATLRLGQFNGNSFTSYKDSAD
RTTRVNFNAKNISIDNFVEINNRVGSGAGRKASSTVLTLQASEGITSSKNAEISLYDGATLNL
ASNSVKLNGNVWMGRLQYVGAYLAPSYSTINTSKVQGEVDFNHLTVGDQNAAQAGIIASNK
THIGTLDLWQSAGLNIIAPPEGGYKDKPNSTTSQSGTKNDKKEISQNNNSNTEVINPPNNTQ
KTETEPTQVIDGPFAGGKDTVVNIFHLNTKADGTIKVGGFKASLTTNAAHLNIGKGGVNLSN
QASGRTLLVENLTGNITVDGPLRVNNQVGGYALAGSSANFEFKAGVDTKNGTATFNNDISL
GRFVNLKVDAHTANFKGIDTGNGGFNTLDFSGVTDKVNINKLITASTNVAVKNFNINELIVKT
NGISVGEYTHFSEDIGSQSRINTVRLETGTRSIFSGGVKFKSGEKLVINDFYYSPWNYFDAR
NVKNVEITRKFASSTPENPWGTSKLMFNNLTLGQNAVMDYSQFSNLTIQGDFINNQGTINYL
VRGGKVATLNVGNAAAMMFNNDIDSATGFYKPLIKINSAQDLIKNTEHVLLKAKIIGYGNVST
GTNGISNVNLEEQFKERLALYNNNRMDTCVVRNTDDIKACGMAIGNQSMVNNPDNYKYLI
GKAWRNIGISKTANGSKISVYYLGNSTPTENGGNTTNLPTNTTNNAHSANYALVKNAPFAHS
ATPNLVAINQHDFGTIESVFELANRSKDIDTLYTHSGAQGRDLLQTLLIDSHDAGYARQMIDN
TSTGEITKQLNAATDALNNVASLEHKQSGLQTLSLSNAMILNSRLVNLSRKHTNHINSFAQRL
QALKGQEFASLESAAEVLYQFAPKYEKPTNVWANAIGGASLNSGSNASLYGTSAGVDAFLN
GNVEAIVGGFGSYGYSSFSNQANSLNSGANNANFGVYSRFFANQHEFDFEAQGALGSDQS
SLNFKSTLLQDLNQSYNYLAYSATARASYGYDFAFFRNALVLKPSVGVSYNHLGSTNFKSN
SQSQVALKNGASSQHLFNANANVEARYYYGDTSYFYLHAGVLQEFAHFGSNDVASLNTFKI
NAARSPLSTYARAMMGGELQLAKEVFLNLGVVYLHNLISNASHFASNLGMRYSF

H  **s1m1 VacA from strain NCTC 11637 (*Ito et al., 1998, J. Infect. Dis., 178(5):1391-8*) (SEQ ID NO: 8)**

MEIQQTHRKINRPLVSLALVGALVSITPQQSHAAFFTTVIIPAIVGGIATGAAVGTVSGLLSWG
LKQAEEANKTPDKPDKVWRIQAGRGFNNFPHKEYDLYKSLLSSKIDGGWDWGNAARHYW
VKGGQWNKLEVDMKDAVGTYKLSGLINFTGGDLDVNMQKATLRLGQFNGNSFTSYKDSA
DRTTRVDFNAKNILIDNFLEINNRVGSGAGRKASSTVLTLQASEGITSSKNAEISLYDGATLN
LASSSVKLMGNVWMGRLQYVGAYLAPSYSTINTSKVTGEVNFNHLTVGDHNAAQAGIIASN
KTHIGTLDLWQSAGLNIIAPPEGGYKDKPKDKPSNTTQNNANNNQQNSAQNNNNTQVINPP
NSAQKTEIQPTQVINGPFAGGKDTVVNINRINTNADGTIRVGGYKASLTTNAAHLHIGKGGIN
LSNQASGRSLLVENLTGNITVDGPLRVNNQVGGYALAGSNANFEFKAGTDTKNGTATFNN
DISLGRFVNLKVDAHTANFKGIDTGNGGFNTLDFSGVTDKVNINKLITASTNVAIKNFNINELL
VKTNGVSVGEYTHFSEDIGSQSRINTVRLETGTRSIFSGGVKFKSGEKLVIDEFYYSPWNYF
DARNIKNVEITRKFASSTPENPWGTSKLMFNNLTLGQNAVMDYSQFSNLTIQGDFINNQGTI
NYLVRGGKVATLNVGNAAAMMFNNDIDSATGFYKPLIKINSAQDLIKNTEHVLLKAKIIGYGN
VSTGTNGISNVNLEEQFKERLALYNNNRMDTCVVRNTDDIKACGMAIGNQSMVNNPDNY
KYLIGKAWKNIGISKTANGSKISVYYLGNSTPTENGGNTTNLPTNTTNNARSANYALVKNAP
FAHSATPNLVAINQHDFGTIESVFELANRSKDIDTLYTHSGAKGRDLLQTLLIDSHDAGYARQ
MIDNTSTGEITKQLNAATTTLNNIASLEHKTSSLQTLSLSNAMILNSRLVNLSRKHTNNIDSFA
KRLQALKDQRFASLESAAEVLYQFAPKYEKPTNVWANAIGGASLNNGSNASLYGTSAGVD
AYLNGQVEAIVGGFGSYGYSSFSNRANSLNSGANNTNFGVYSRIFANQHEFDFEAQGALG
SDQSSLNFKSALLQDLNQSYNYLAYSAATRASYGYDFAFFKNALVLKPSVGVSYNHLGSTN
FKSNSTNKVALSNGSSSQHLFNASANVEARYYYGDTSYFYMNAGVLQEFANFGSSNAVSL
NTFKVNAARNPLNTHARVMMGGELQLAKEVFLNLGFVYLHNLISNIGHFASNLGMRYSF

Figure 5 (continued)

I s1m1 VacA of strain *H. pylori* P12 (*Fischer et al., 2010, Nucleic Acids Res. 38(18):6089-101*) (SEQ ID NO: 9)

MEIQQTHRKINRPLVSLALVGALVSITPQQSHAAFFTTVIIPAIVGGIASGAAVGTVSGLLGWGL
KQAEEANKTPDKPDKVWRIQAGKGFNEFPNKEYDLYRSLLSSKIDGGWDWGNAATHYWVK
GGQWNKLEVDMKDAVGTYNLSGLRNFTGGDLDVNMQKATLRLGQFNGNSFTSYKDSADRT
TRVDFNAKNISIDNFLEINNRVGSGAGRKASSTVLTLQASEGITSSKNAEISLYDGATLNLASSS
VKLMGNVWMGRLQYVGAYLAPSYSTINTSKVTGEVNFNHLTVGDRNAAQAGIIASNKTHIGTL
DLWQSAGLNIIAPPEGGYKDKPNNTPSQSGAKNDKNESAKNDKQESSQNNSNTQVINPPNS
AQKTEVQPTQVIDGPFAGGKDTVVNINRINTNADGTIRVGGYKASLTTNAAHLHIGKGGVNLS
NQASGRTLLVENLTGNITVDGPLRVNNQVGGYALAGSSANFEFKAGTDTKNGTATFNNDISL
GRFVNLKVDAHTANFKGIDTGNGGFNTLDFSGVTDKVNINKLITASTNVAIKNFNINELLVKTNG
VSVGEYTHFSEDIGSQSRINTVRLETGTRSIFSGGVKFKGGEKLVINDFYYAPWNYFDARNIKN
VEITNKLAFGPQGSPWGTSKLMFNNLTLGQNAVMDYSQFSNLTIQGDFVNNQGTINYLVRGG
QVATLNVGNAAAMFFNNNVDSATGFYQPLMKINSAQDLIKNKEHVLLKAKIIGYGNVSAGTNSI
SNVNLIEQFKERLALYEHNNRMDICVVRNTDDIKACGTAIGNQSMVNNPDNYKYLIGKAWKNI
GISKTANGSKISVHYLGNSTPTENSGNTTNLPTNTTSNARSAKNALAQNAPFAQPSATPSLVAI
NQHDFGTIESVFELANRSKDIDTLYTHSGAQGRNLLQTLLIDSHDAGYARQMIDNTSTGEIIKQL
NAATTTLNNVASLEHKQSGLQTLSLSNAMILNSRLVNLSRRHTNNIDSFAQRLQALKDQKFAS
LESAAEVLYQFAPKYEKPTNVWANAIGGTSLNNGGNASLYGTSAGVDAYLNGEVEAIVGGFG
SYGYSSFSNQANSLNSGANNTNFGVYSRLFANQHEFDFEAQGALGSDQSSLNFKSALLRDL
NQSYNYLAYSAATRASYGYDFAFFRNALVLKPSVGVSYNHLGSTNFKSNSTNQVALKNGSSS
QHLFNASANVEARYYYGDTSYFYMNAGVLQEFANFGSSNAVSLNTFKVNAARNPLNTHARV
MMGGELKLAKEVFLNLGFVYLHNLISNIGHFASNLGMRYSF

J s1m1 VacA of strain *H. pylori* (*Haas et al., 1994, Mol. Microbiol., 12:307-319*) (SEQ ID NO: 10)

MEIQQTHRKINRPLVSLALVGALVSITPQQSHAAFFTTVIIPAIVGGIATGAAVGTVSGLLGWGL
KQAEEANKTPDKPDKVWRIQAGKGFNEFPNKEYDLYKSLLSSKIDGGWDWGNAARHYWVK
DGQWNKLEVDMQNAVGTYNLSGLINFTGGDLDVNMQKATLRLGQFNGNSFTSYKDSADRT
TRVDFNAKNILIDNFLEINNRVGSGAGRKASSTVLTLQASEGITSRENAEISLYDGATLNLASN
SVKLMGNVWMGRLQYVGAYLAPSYSTINTSKVTGEVNFNHLTVGDHNAAQAGIIASNKTHIG
TLDLWQSAGLNIIAPPEGGYKDKPNDKPSNTTQNNAKNDKQESSQNNSNTQVINPPNSAQKT
EIQPTQVIDGPFAGGKNTVVNINRINTNADGTIRVGGFKASLTTNAAHLHIGKGGINLSNQASG
RSLLVENLTGNITVDGPLRVNNQVGGYALAGSSANFEFKAGTDTKNGTATFNNDISLGRFVN
LKVDAHTANFKGIDTGNGGFNTLDFSGVTNKVNINKLITASTNVAVKNFNINELVVKTNGVSVG
EYTHFSEDIGSQSRINTVRLETGTRSIYSGGVKFKGGEKLVINDFYYAPWNYFDARNIKNVEIT
NKLAFGPQGSPWGTAKLMFNNLTLGQNAVMDYSQFSNLTIQGDFVNNQGTINYLVRGGQVA
TLNVGNAAAMFFSNNVDSATGFYQPLMKINSAQDLIKNKEHVLLKAKIIGYGNVSAGTDSIANV
NLIEQFKERLALYNNNRMDICVVRNTDDIKACGTAIGNQSMVNNPENYKYLEGKAWKNIGIS
KTANGSKISVHYLGNSTPTENGGNTTNLPTNTTNKVRFASYALIKNAPFARYSATPNLVAINQ
HDFGTIESVFELANRSNDIDTLYANSGAQGRDLLQTLLIDSHDAGYARTMIDATSANEITKQLN
TATTTLNNIASLEHKTSGLQTLSLSNAMILNSRLVNLSRRHTNHIDSFAKRLQALKDQRFASLE
SAAEVLYQFAPKYEKPTNVWANAIGGTSLNSGGNASLYGTSAGVDAYLNGEVEAIVGGFGSY
GYSSFSNQANSLNSGANNTNFGVYSRIFANQHEFDFEAQGALGSDQSSLNFKSALLRDLNQ
SYNYLAYSAATRASYGYDFAFFRNALVLKPSVGVSYNHLGSTNFKSNSNQKVALKNGASSQ
HLFNASANVEARYYYGDTSYFYMNAGVLQEFANFGSSNAVSLNTFKVNATRNPLNTHARVM
MGGELKLAKEVFLNLGFVYLHNLISNIGHFASNLGMRYSF

Figure 5 (continued)

K  s1m1 VacA of strain *H. pylori* NCTC 11638 (*Phadnis et al., 1994, Infect. Immun. 62:1557-1565*) (SEQ ID NO: 11)

MEIQQTHRKINRPLVSLALVGALVSITPQQSHAAFFTTVIIPAIVGGIATGTAVGTVSGLLSWGLK
QAEEANKTPDKPDKVWRIQAGKGFNEFPNKEYDLYRSLLSSKIDGGWDWGNAARHYWVKG
GQQNKLEVDMKDAVGTYTLSGLRNFTGGDLDVNMQKATLRLGQFNGNSFTSYKDSADRTTR
VDFNAKNISIDNFVEINNRVGSGAGRKASSTVLTLQASEGITSDKNAEISLYDGATLNLASSS
VKLMGNVWMGRLQYVGAYLAPSYSTINTSKVTGEVNFNHLTVGDKNAAQAGIIANKKTNIGTL
DLWQSAGLNIIAPPEGGYKDKPNNTPSQSGAKNDKNESAKNDKQESSQNNSNTQVINPPNS
AQKTEVQPTQVIDGPFAGGKDTVVNINRINTNADGTIRVGGFKASLTTNAAHLHIGKGGVNLS
NQASGRSLIVENLTGNITVDGPLRVNNQVGGYALAGSSANFEFKAGTDTKNGTATFNNDISLG
RFVNLKVDAHTANFKGIDTGNGGFNTLDFSGVTDKVNINKLITASTNVAVKNFNINELIVKTNGI
SVGEYTHFSEDIGSQSRINTVRLETGTRSLFSGGVKFKGGEKLVIDEFYYSPWNYFDARNIKN
VEITNKLAFGPQGSPWGTSKLMFNNLTLGQNAVMDYSQFSNLTIQGDFINNQGTINYLVRGGK
VATLSVGNAAAMMFNNDIDSATGFYKPLIKINSAQDLIKNTEHVLLKAKIIGYGNVSTGTNGISN
VNLEEQFKERLALYNNNRMDTCVVRNTDDIKACGMAIGDQSMVNNPDNYKYLIGKAWKNIG
ISKTANGSKISVYYLGNSTPTENGGNTTNLPTNTTSNARSANNALAQNAPFAQPSATPNLVAI
NQHDFGTIESVFELANRSKDIDTLYANSGAQGRDLLQTLLIDSHDAGYARKMIDATSANEITKQ
LNTATTTLNNIASLEHKTSGLQTLSLSNAMILNSRLVNLSRRHTNHIDSFAKRLQALKDQKFASL
ESAAEVLYQFAPKYEKPTNVWANAIGGTSLNNGSNASLYGTSAGVDAYLNGQVEAIVGGFGS
YGYSSFNNRANSLNSGANNTNFGVYSRIFANQHEFDFEAQGALGSDQSSLNFKSALLQDLNQ
SYHYLAYSAATRASYGYDFAFFRNALVLKPSVGVSYNHLGSTNFKSNSTNQVALKNGSSSQH
LFNASANVEARYYYGDTSYFYMNAGVLQEFAHVGSNNAASLNTFKVNAARNPLNTHARVMM
GGELKLAKEVFLNLGVVYLHNLISNIGHFASNLGMRYSFF

Figure 5 (continued)

**K s1m1 VacA of strain H. pylori NCTC 11638 (*Phadnis et al., 1994, Infect. Immun. 62:1557-1565*) (SEQ ID NO: 11)**

MEIQQTHRKINRPLVSLALVGALVSITPQQSHAAFFTTVIIPAIVGGIATGTAVGTVSGLLSWGLK
QAEEANKTPDKPDKVWRIQAGKGFNEFPNKEYDLYRSLLSSKIDGGWDWGNAARHYWVKG
GQQNKLEVDMKDAVGTYTLSGLRNFTGGDLDVNMQKATLRLGQFNGNSFTSYKDSADRTTR
VDFNAKNISIDNFVEINNRVGSGAGRKASSTVLTLQASEGITSDKNAEISLYDGATLNLASSS
VKLMGNVWMGRLQYVGAYLAPSYSTINTSKVTGEVNFNHLTVGDKNAAQAGIIANKKTNIGTL
DLWQSAGLNIIAPPEGGYKDKPNNTPSQSGAKNDKNESAKNDKQESSQNNSNTQVINPPNS
AQKTEVQPTQVIDGPFAGGKDTVVNINRINTNADGTIRVGGFKASLTTNAAHLHIGKGGVNLS
NQASGRSLIVENLTGNITVDGPLRVNNQVGGYALAGSSANFEFKAGTDTKNGTATFNNDISLG
RFVNLKVDAHTANFKGIDTGNGGFNTLDFSGVTDKVNINKLITASTNVAVKNFNINELIVKTNGI
SVGEYTHFSEDIGSQSRINTVRLETGTRSLFSGGVKFKGGEKLVIDEFYYSPWNYFDARNIKN
VEITNKLAFGPQGSPWGTSKLMFNNLTLGQNAVMDYSQFSNLTIQGDFINNQGTINYLVRGGK
VATLSVGNAAAMMFNNDIDSATGFYKPLIKINSAQDLIKNTEHVLLKAKIIGYGNVSTGTNGISN
VNLEEQFKERLALYNNNNRMDTCVVRNTDDIKACGMAIGDQSMVNNPDNYKYLIGKAWKNIG
ISKTANGSKISVYYLGNSTPTENGGNTTNLPTNTTSNARSANNALAQNAPFAQPSATPNLVAI
NQHDFGTIESVFELANRSKDIDTLYANSGAQGRDLLQTLLIDSHDAGYARKMIDATSANEITKQ
LNTATTTLNNIASLEHKTSGLQTLSLSNAMILNSRLVNLSRRHTNHIDSFAKRLQALKDQKFASL
ESAAEVLYQFAPKYEKPTNVWANAIGGTSLNNGSNASLYGTSAGVDAYLNGQVEAIVGGFGS
YGYSSFNNRANSLNSGANNTNFGVYSRIFANQHEFDFEAQGALGSDQSSLNFKSALLQDLNQ
SYHYLAYSAATRASYGYDFAFFRNALVLKPSVGVSYNHLGSTNFKSNSTNQVALKNGSSSQH
LFNASANVEARYYYGDTSYFYMNAGVLQEFAHVGSNNAASLNTFKVNAARNPLNTHARVMM
GGELKLAKEVFLNLGVVYLHNLISNIGHFASNLGMRYSFF

SEQUENCE LISTING

```
<160> NUMBER OF SEQ ID NOS: 11

<210> SEQ ID NO 1
<211> LENGTH: 980
<212> TYPE: PRT
<213> ORGANISM: Helicobacter pylori strain ATCC 49503/60190

<400> SEQUENCE: 1

Ala Phe Phe Thr Thr Val Ile Ile Pro Ala Ile Val Gly Gly Ile Ala
1               5                   10                  15

Thr Gly Thr Ala Val Gly Thr Val Ser Gly Leu Leu Gly Trp Gly Leu
                20                  25                  30

Lys Gln Ala Glu Glu Ala Asn Lys Thr Pro Asp Lys Pro Asp Lys Val
            35                  40                  45

Trp Arg Ile Gln Ala Gly Lys Gly Phe Asn Glu Phe Pro Asn Lys Glu
        50                  55                  60

Tyr Asp Leu Tyr Lys Ser Leu Leu Ser Ser Lys Ile Asp Gly Gly Trp
65                  70                  75                  80

Asp Trp Gly Asn Ala Ala Thr His Tyr Trp Ile Lys Gly Gly Gln Trp
                85                  90                  95

Asn Lys Leu Glu Val Asp Met Lys Asp Ala Val Gly Thr Tyr Lys Leu
                100                 105                 110
```

-continued

```
Ser Gly Leu Arg Asn Phe Thr Gly Gly Asp Leu Asp Val Asn Met Gln
        115                 120                 125

Lys Ala Thr Leu Arg Leu Gly Gln Phe Asn Gly Asn Ser Phe Thr Ser
130                 135                 140

Tyr Lys Asp Ser Ala Asp Arg Thr Thr Arg Val Asp Phe Asn Ala Lys
145                 150                 155                 160

Asn Ile Leu Ile Asp Asn Phe Leu Glu Ile Asn Asn Arg Val Gly Ser
                165                 170                 175

Gly Ala Gly Arg Lys Ala Ser Ser Thr Val Leu Thr Leu Gln Ala Ser
            180                 185                 190

Glu Gly Ile Thr Ser Ser Lys Asn Ala Glu Ile Ser Leu Tyr Asp Gly
        195                 200                 205

Ala Thr Leu Asn Leu Ala Ser Asn Ser Val Lys Leu Asn Gly Asn Val
210                 215                 220

Trp Met Gly Arg Leu Gln Tyr Val Gly Ala Tyr Leu Ala Pro Ser Tyr
225                 230                 235                 240

Ser Thr Ile Asn Thr Ser Lys Val Thr Gly Glu Val Asn Phe Asn His
                245                 250                 255

Leu Thr Val Gly Asp His Asn Ala Ala Gln Ala Gly Ile Ile Ala Ser
            260                 265                 270

Asn Lys Thr His Ile Gly Thr Leu Asp Leu Trp Gln Ser Ala Gly Leu
        275                 280                 285

Asn Ile Ile Ala Pro Pro Glu Gly Gly Tyr Lys Asp Lys Pro Asn Asn
290                 295                 300

Thr Pro Ser Gln Ser Gly Ala Lys Asn Asp Lys Gln Glu Ser Ser Gln
305                 310                 315                 320

Asn Asn Ser Asn Thr Gln Val Ile Asn Pro Pro Asn Ser Thr Gln Lys
                325                 330                 335

Thr Glu Val Gln Pro Thr Gln Val Ile Asp Gly Pro Phe Ala Gly Gly
            340                 345                 350

Lys Asp Thr Val Val Asn Ile Asp Arg Ile Asn Thr Lys Ala Asp Gly
        355                 360                 365

Thr Ile Lys Val Gly Gly Phe Lys Ala Ser Leu Thr Thr Asn Ala Ala
370                 375                 380

His Leu Asn Ile Gly Lys Gly Gly Val Asn Leu Ser Asn Gln Ala Ser
385                 390                 395                 400

Gly Arg Thr Leu Leu Val Glu Asn Leu Thr Gly Asn Ile Thr Val Asp
                405                 410                 415

Gly Pro Leu Arg Val Asn Asn Gln Val Gly Gly Tyr Ala Leu Ala Gly
            420                 425                 430

Ser Ser Ala Asn Phe Glu Phe Lys Ala Gly Val Asp Thr Lys Asn Gly
        435                 440                 445

Thr Ala Thr Phe Asn Asn Asp Ile Ser Leu Gly Arg Phe Val Asn Leu
450                 455                 460

Lys Val Asp Ala His Thr Ala Asn Phe Lys Gly Ile Asp Thr Gly Asn
465                 470                 475                 480

Gly Gly Phe Asn Thr Leu Asp Phe Ser Gly Val Thr Asn Lys Val Asn
                485                 490                 495

Ile Asn Lys Leu Ile Thr Ala Ser Thr Asn Val Ala Val Lys Asn Phe
            500                 505                 510

Asn Ile Asn Glu Leu Ile Val Lys Thr Asn Gly Val Ser Val Gly Glu
        515                 520                 525
```

```
Tyr Thr His Phe Ser Glu Asp Ile Gly Ser Gln Ser Arg Ile Asn Thr
    530                 535                 540

Val Arg Leu Glu Thr Gly Thr Arg Ser Ile Phe Ser Gly Gly Val Lys
545                 550                 555                 560

Phe Lys Ser Gly Glu Lys Leu Val Ile Asp Glu Phe Tyr Tyr Ser Pro
                565                 570                 575

Trp Asn Tyr Phe Asp Ala Arg Asn Ile Lys Asn Val Glu Ile Thr Arg
            580                 585                 590

Lys Phe Ala Ser Ser Thr Pro Glu Asn Pro Trp Gly Thr Ser Lys Leu
        595                 600                 605

Met Phe Asn Asn Leu Thr Leu Gly Gln Asn Ala Val Met Asp Tyr Ser
    610                 615                 620

Gln Phe Ser Asn Leu Thr Ile Gln Gly Asp Phe Ile Asn Asn Gln Gly
625                 630                 635                 640

Thr Ile Asn Tyr Leu Val Arg Gly Gly Lys Val Ala Thr Leu Asn Val
                645                 650                 655

Gly Asn Ala Ala Ala Met Met Phe Asn Asn Asp Ile Asp Ser Ala Thr
            660                 665                 670

Gly Phe Tyr Lys Pro Leu Ile Lys Ile Asn Ser Ala Gln Asp Leu Ile
        675                 680                 685

Lys Asn Thr Glu His Val Leu Leu Lys Ala Lys Ile Ile Gly Tyr Gly
    690                 695                 700

Asn Val Ser Thr Gly Thr Gly Ile Ser Asn Val Asn Leu Glu Glu
705                 710                 715                 720

Gln Phe Lys Glu Arg Leu Ala Leu Tyr Asn Asn Asn Arg Met Asp
                725                 730                 735

Thr Cys Val Val Arg Asn Thr Asp Asp Ile Lys Ala Cys Gly Met Ala
            740                 745                 750

Ile Gly Asn Gln Ser Met Val Asn Asn Pro Asp Asn Tyr Lys Tyr Leu
        755                 760                 765

Ile Gly Lys Ala Trp Lys Asn Ile Gly Ile Ser Lys Thr Ala Asn Gly
    770                 775                 780

Ser Lys Ile Ser Val Tyr Tyr Leu Gly Asn Ser Thr Pro Thr Glu Asn
785                 790                 795                 800

Gly Gly Asn Thr Thr Asn Leu Pro Thr Asn Thr Thr Asn Asn Ala Arg
                805                 810                 815

Phe Ala Ser Tyr Ala Leu Ile Lys Asn Ala Pro Phe Ala His Ser Ala
            820                 825                 830

Thr Pro Asn Leu Val Ala Ile Asn Gln His Asp Phe Gly Thr Ile Glu
        835                 840                 845

Ser Val Phe Glu Leu Ala Asn Arg Ser Lys Asp Ile Asp Thr Leu Tyr
    850                 855                 860

Ala Asn Ser Gly Ala Gln Gly Arg Asp Leu Leu Gln Thr Leu Leu Ile
865                 870                 875                 880

Asp Ser His Asp Ala Gly Tyr Ala Arg Thr Met Ile Asp Ala Thr Ser
                885                 890                 895

Ala Asn Glu Ile Thr Lys Gln Leu Asn Thr Ala Thr Thr Thr Leu Asn
            900                 905                 910

Asn Ile Ala Ser Leu Glu His Lys Thr Ser Ser Leu Gln Thr Leu Ser
        915                 920                 925

Leu Ser Asn Ala Met Ile Leu Asn Ser Arg Leu Val Asn Leu Ser Arg
    930                 935                 940

Arg His Thr Asn Asn Ile Asp Ser Phe Ala Lys Arg Leu Gln Ala Leu
```

```
            945                 950                 955                 960
Lys Asp Gln Arg Phe Ala Ser Leu Glu Ser Ala Ala Glu Val Leu Tyr
                    965                 970                 975
Gln Phe Ala Pro
                980

<210> SEQ ID NO 2
<211> LENGTH: 1309
<212> TYPE: PRT
<213> ORGANISM: Helicobacter pylori strainTx30a

<400> SEQUENCE: 2

Met Glu Ile Gln Gln Thr His Arg Lys Ile Asn Arg Pro Ile Ile Ser
1               5                   10                  15

Leu Ala Leu Val Gly Val Leu Met Gly Thr Glu Leu Gly Ala Asn Thr
                20                  25                  30

Pro Asn Asp Pro Ile His Ser Glu Ser Arg Ala Phe Phe Thr Thr Val
            35                  40                  45

Ile Ile Pro Ala Ile Val Gly Gly Ile Ala Thr Gly Ala Ala Val Gly
        50                  55                  60

Thr Val Ser Gly Leu Leu Ser Trp Gly Leu Lys Gln Ala Glu Gln Ala
65                  70                  75                  80

Asn Lys Ala Pro Asp Lys Pro Asp Lys Val Trp Arg Ile Gln Ala Gly
                85                  90                  95

Arg Gly Phe Asp Asn Phe Pro His Lys Gln Tyr Asp Leu Tyr Lys Ser
                100                 105                 110

Leu Leu Ser Ser Lys Ile Asp Gly Gly Trp Asp Trp Gly Asn Ala Ala
            115                 120                 125

Arg His Tyr Trp Val Lys Asp Gly Gln Trp Asn Lys Leu Glu Val Asp
        130                 135                 140

Met Gln Asn Ala Val Gly Thr Tyr Asn Leu Ser Gly Leu Ile Asn Phe
145                 150                 155                 160

Thr Gly Gly Asp Leu Asp Val Asn Met Gln Lys Ala Thr Leu Arg Leu
                165                 170                 175

Gly Gln Phe Asn Gly Asn Ser Phe Thr Ser Phe Lys Asp Gly Ala Asn
            180                 185                 190

Arg Thr Thr Arg Val Asn Phe Asp Ala Lys Asn Ile Leu Ile Asp Asn
        195                 200                 205

Phe Val Glu Ile Asn Asn Arg Val Gly Ser Gly Ala Gly Arg Lys Ala
    210                 215                 220

Ser Ser Thr Val Leu Thr Leu Lys Ser Ser Glu Lys Ile Thr Ser Arg
225                 230                 235                 240

Glu Asn Ala Glu Ile Ser Leu Tyr Asp Gly Ala Thr Leu Asn Leu Val
                245                 250                 255

Ser Ser Ser Asn Gln Ser Val Asp Leu Tyr Gly Lys Val Trp Met Gly
            260                 265                 270

Arg Leu Gln Tyr Val Gly Ala Tyr Leu Ala Pro Ser Tyr Ser Thr Ile
        275                 280                 285

Asp Thr Ser Lys Val Gln Gly Glu Met Asn Phe Arg His Leu Ala Val
    290                 295                 300

Gly Asp Gln Asn Ala Ala Gln Ala Gly Ile Ile Ala Asn Lys Lys Thr
305                 310                 315                 320

Asn Ile Gly Thr Leu Asp Leu Trp Gln Ser Ala Gly Leu Ser Ile Ile
                325                 330                 335
```

-continued

```
Thr Pro Pro Glu Gly Gly Tyr Glu Ser Lys Thr Lys Asp Asn Pro Gln
                340                 345                 350

Asn Asn Pro Lys Asn Asp Ala Gln Lys Thr Glu Ile Gln Pro Thr Gln
            355                 360                 365

Val Ile Asp Gly Pro Phe Ala Gly Gly Lys Asp Thr Val Val Asn Ile
        370                 375                 380

Phe His Leu Asn Thr Lys Ala Asp Gly Thr Leu Arg Ala Gly Gly Phe
385                 390                 395                 400

Lys Ala Ser Leu Ser Thr Asn Ala Ala His Leu His Ile Gly Glu Gly
                405                 410                 415

Gly Val Asn Leu Ser Asn Gln Ala Ser Gly Arg Thr Leu Leu Val Glu
            420                 425                 430

Asn Leu Thr Gly Asn Ile Thr Val Glu Gly Thr Leu Arg Val Asn Asn
        435                 440                 445

Gln Val Gly Gly Ala Ala Ile Ala Gly Ser Ser Ala Asn Phe Glu Phe
    450                 455                 460

Lys Ala Gly Glu Asp Thr Asn Asn Ala Thr Ala Thr Phe Asn Asn Asp
465                 470                 475                 480

Ile His Leu Gly Lys Ala Val Asn Leu Arg Val Asp Ala His Thr Ala
                485                 490                 495

Asn Phe Asn Gly Asn Ile Tyr Leu Gly Lys Ser Thr Asn Leu Arg Val
            500                 505                 510

Asn Gly His Thr Ala His Phe Lys Asn Ile Asp Ala Thr Lys Ser Asp
        515                 520                 525

Asn Gly Leu Asn Thr Ser Thr Leu Asp Phe Ser Gly Val Thr Asp Lys
    530                 535                 540

Val Asn Ile Asn Lys Leu Thr Thr Ala Ala Thr Asn Val Asn Ile Lys
545                 550                 555                 560

Asn Phe Asp Ile Lys Glu Leu Val Val Thr Thr Arg Val Gln Ser Phe
                565                 570                 575

Gly Gln Tyr Thr Ile Phe Gly Glu Asn Ile Gly Asp Lys Ser Arg Ile
            580                 585                 590

Gly Val Val Ser Leu Gln Thr Gly Tyr Ser Pro Ala Tyr Ser Gly Gly
        595                 600                 605

Val Thr Phe Lys Gly Gly Lys Lys Leu Val Ile Asp Glu Ile Tyr His
    610                 615                 620

Ala Pro Trp Asn Tyr Phe Asp Ala Arg Asn Val Thr Asp Val Glu Ile
625                 630                 635                 640

Asn Lys Arg Ile Leu Phe Gly Ala Pro Gly Asn Ile Ala Gly Lys Thr
                645                 650                 655

Gly Leu Met Phe Asn Asn Leu Thr Leu Asn Ser Asn Ala Ser Met Asp
            660                 665                 670

Tyr Gly Lys Asp Leu Asp Leu Thr Ile Gln Gly His Phe Thr Asn Asn
        675                 680                 685

Gln Gly Thr Met Asn Leu Phe Val Gln Asp Gly Arg Val Ala Thr Leu
    690                 695                 700

Asn Ala Gly His Gln Ala Ser Met Ile Phe Asn Asn Leu Val Asp Ser
705                 710                 715                 720

Thr Thr Gly Phe Tyr Lys Pro Leu Ile Lys Ile Asn Asn Ala Gln Asn
                725                 730                 735

Leu Thr Lys Asn Lys Glu His Val Leu Val Lys Ala Arg Asn Ile Asp
            740                 745                 750

Tyr Asn Leu Val Gly Val Gln Gly Ala Ser Tyr Asp Asn Ile Ser Ala
```

```
                    755                 760                 765
Ser Asn Thr Asn Leu Gln Glu Gln Phe Lys Glu Arg Leu Ala Leu Tyr
770                 775                 780

Asn Asn Asn Asn Arg Met Asp Thr Cys Val Val Arg Lys Asp Asn Leu
785                 790                 795                 800

Asn Asp Ile Lys Ala Cys Gly Met Ala Ile Gly Asn Gln Ser Met Val
                805                 810                 815

Asn Asn Pro Glu Asn Tyr Lys Tyr Leu Glu Gly Lys Ala Trp Lys Asn
                820                 825                 830

Thr Gly Ile Asn Lys Thr Ala Asn Asn Thr Thr Ile Ala Val Asn Leu
                835                 840                 845

Gly Asn Asn Ser Thr Pro Thr Asn Ser Thr Thr Asp Thr Thr Asn Leu
850                 855                 860

Pro Thr Asn Thr Thr Asn Asn Ala Arg Phe Ala Ser Tyr Ala Leu Ile
865                 870                 875                 880

Lys Asn Ala Pro Phe Ala His Ser Ala Thr Pro Asn Leu Val Ala Ile
                885                 890                 895

Asn Gln His Asp Phe Gly Thr Ile Glu Ser Val Phe Glu Leu Ala Asn
                900                 905                 910

Arg Ser Ser Asp Ile Asp Thr Leu Tyr Ala Asn Ser Gly Ala Gln Gly
                915                 920                 925

Arg Asp Leu Leu Gln Thr Leu Leu Ile Asp Ser His Asp Ala Gly Tyr
930                 935                 940

Ala Arg Thr Met Ile Asp Ala Thr Ser Ala Asn Glu Ile Thr Gln Gln
945                 950                 955                 960

Leu Asn Ala Ala Thr Thr Thr Leu Asn Asn Ile Ala Ser Leu Glu His
                965                 970                 975

Lys Thr Ser Gly Leu Gln Thr Leu Ser Leu Ser Asn Ala Met Ile Leu
                980                 985                 990

Asn Ser Arg Leu Val Asn Leu Ser Arg Lys His Thr Asn His Ile Asp
                995                 1000                1005

Ser Phe Ala Lys Arg Leu Gln Ala Leu Lys Asp Gln Arg Phe Ala
                1010                1015                1020

Ser Leu Glu Ser Ala Ala Glu Val Leu Tyr Gln Phe Ala Pro Lys
                1025                1030                1035

Tyr Glu Lys Pro Thr Asn Val Trp Ala Asn Ala Ile Gly Gly Thr
                1040                1045                1050

Ser Leu Asn Asn Gly Ser Asn Ala Ser Leu Tyr Gly Thr Ser Ala
                1055                1060                1065

Gly Val Asp Ala Tyr Leu Asn Gly Glu Val Glu Ala Ile Val Gly
                1070                1075                1080

Gly Phe Gly Ser Tyr Gly Tyr Ser Ser Phe Ser Asn Gln Ala Asn
                1085                1090                1095

Ser Leu Asn Ser Gly Ala Asn Asn Thr Asn Phe Gly Val Tyr Ser
                1100                1105                1110

Arg Ile Phe Ala Asn Gln His Glu Phe Asp Phe Glu Ala Gln Gly
                1115                1120                1125

Ala Leu Gly Ser Asp Gln Ser Leu Asn Phe Lys Ser Ala Leu
                1130                1135                1140

Leu Gln Asp Leu Asn Gln Ser Tyr His Tyr Leu Ala Tyr Ser Ala
                1145                1150                1155

Thr Thr Arg Ala Ser Tyr Gly Tyr Asp Phe Ala Phe Phe Arg Asn
                1160                1165                1170
```

Ala Leu Val Leu Lys Pro Ser Val Gly Val Ser Tyr Asn His Leu
    1175                1180                1185

Gly Ser Thr Asn Phe Lys Ser Asn Ser Asn Gln Val Ala Leu Ser
    1190                1195                1200

Asn Gly Ser Ser Ser Gln His Leu Phe Asn Ala Asn Ala Asn Val
    1205                1210                1215

Glu Ala Arg Tyr Tyr Gly Asp Thr Ser Tyr Phe Tyr Met Asn
    1220                1225                1230

Ala Gly Val Leu Gln Glu Phe Ala Arg Phe Gly Ser Asn Asn Ala
    1235                1240                1245

Val Ser Leu Asn Thr Phe Lys Val Asn Ala Thr Arg Asn Pro Leu
    1250                1255                1260

Asn Thr His Ala Arg Val Met Met Gly Gly Glu Leu Gln Leu Ala
    1265                1270                1275

Lys Glu Val Phe Leu Asn Leu Gly Val Val Tyr Leu His Asn Leu
    1280                1285                1290

Ile Ser Asn Ala Ser His Phe Ala Ser Asn Leu Gly Met Arg Tyr
    1295                1300                1305

Ser

<210> SEQ ID NO 3
<211> LENGTH: 957
<212> TYPE: PRT
<213> ORGANISM: Artificial sequence
<220> FEATURE:
<223> OTHER INFORMATION: Deletion variant del 6-27 VacA

<400> SEQUENCE: 3

Ala Phe Phe Thr Thr Leu Gly Trp Gly Leu Lys Gln Ala Glu Ala
1               5                   10                  15

Asn Lys Thr Pro Asp Lys Pro Asp Lys Val Trp Arg Ile Gln Ala Gly
                20                  25                  30

Lys Gly Phe Asn Glu Phe Pro Asn Lys Glu Tyr Asp Leu Tyr Lys Ser
                35                  40                  45

Leu Leu Ser Ser Lys Ile Asp Gly Gly Trp Asp Trp Gly Asn Ala Ala
    50                  55                  60

Thr His Tyr Trp Ile Lys Gly Gly Gln Trp Asn Lys Leu Glu Val Asp
65                  70                  75                  80

Met Lys Asp Ala Val Gly Thr Tyr Lys Leu Ser Gly Leu Arg Asn Phe
                85                  90                  95

Thr Gly Gly Asp Leu Asp Val Asn Met Gln Lys Ala Thr Leu Arg Leu
                100                 105                 110

Gly Gln Phe Asn Gly Asn Ser Phe Thr Ser Tyr Lys Asp Ser Ala Asp
            115                 120                 125

Arg Thr Thr Arg Val Asp Phe Asn Ala Lys Asn Ile Leu Ile Asp Asn
    130                 135                 140

Phe Leu Glu Ile Asn Asn Arg Val Gly Ser Gly Ala Gly Arg Lys Ala
145                 150                 155                 160

Ser Ser Thr Val Leu Thr Leu Gln Ala Ser Glu Gly Ile Thr Ser Ser
                165                 170                 175

Lys Asn Ala Glu Ile Ser Leu Tyr Asp Gly Ala Thr Leu Asn Leu Ala
                180                 185                 190

Ser Asn Ser Val Lys Leu Asn Gly Asn Val Trp Met Gly Arg Leu Gln
            195                 200                 205

-continued

```
Tyr Val Gly Ala Tyr Leu Ala Pro Ser Tyr Ser Thr Ile Asn Thr Ser
    210                 215                 220
Lys Val Thr Gly Glu Val Asn Phe Asn His Leu Thr Val Gly Asp His
225                 230                 235                 240
Asn Ala Ala Gln Ala Gly Ile Ile Ala Ser Asn Lys Thr His Ile Gly
                245                 250                 255
Thr Leu Asp Leu Trp Gln Ser Ala Gly Leu Asn Ile Ile Ala Pro Pro
            260                 265                 270
Glu Gly Gly Tyr Lys Asp Lys Pro Asn Asn Thr Pro Ser Gln Ser Gly
        275                 280                 285
Ala Lys Asn Asp Lys Gln Glu Ser Ser Gln Asn Asn Ser Asn Thr Gln
    290                 295                 300
Val Ile Asn Pro Pro Asn Ser Thr Gln Lys Thr Glu Val Gln Pro Thr
305                 310                 315                 320
Gln Val Ile Asp Gly Pro Phe Ala Gly Gly Lys Asp Thr Val Val Asn
                325                 330                 335
Ile Asp Arg Ile Asn Thr Lys Ala Asp Gly Thr Ile Lys Val Gly Gly
            340                 345                 350
Phe Lys Ala Ser Leu Thr Thr Asn Ala Ala His Leu Asn Ile Gly Lys
        355                 360                 365
Gly Gly Val Asn Leu Ser Asn Gln Ala Ser Gly Arg Thr Leu Leu Val
    370                 375                 380
Glu Asn Leu Thr Gly Asn Ile Thr Val Asp Gly Pro Leu Arg Val Asn
385                 390                 395                 400
Asn Gln Val Gly Gly Tyr Ala Leu Ala Gly Ser Ser Ala Asn Phe Glu
                405                 410                 415
Phe Lys Ala Gly Val Asp Thr Lys Asn Gly Thr Ala Thr Phe Asn Asn
            420                 425                 430
Asp Ile Ser Leu Gly Arg Phe Val Asn Leu Lys Val Asp Ala His Thr
        435                 440                 445
Ala Asn Phe Lys Gly Ile Asp Thr Gly Asn Gly Phe Asn Thr Leu
    450                 455                 460
Asp Phe Ser Gly Val Thr Asn Lys Val Asn Ile Asn Lys Leu Ile Thr
465                 470                 475                 480
Ala Ser Thr Asn Val Ala Val Lys Asn Phe Asn Ile Asn Glu Leu Ile
                485                 490                 495
Val Lys Thr Asn Gly Val Ser Val Gly Glu Tyr Thr His Phe Ser Glu
            500                 505                 510
Asp Ile Gly Ser Gln Ser Arg Ile Asn Thr Val Arg Leu Glu Thr Gly
        515                 520                 525
Thr Arg Ser Ile Phe Ser Gly Gly Val Lys Phe Lys Ser Gly Glu Lys
    530                 535                 540
Leu Val Ile Asp Glu Phe Tyr Tyr Ser Pro Trp Asn Tyr Phe Asp Ala
545                 550                 555                 560
Arg Asn Ile Lys Asn Val Glu Ile Thr Arg Lys Phe Ala Ser Ser Thr
                565                 570                 575
Pro Glu Asn Pro Trp Gly Thr Ser Lys Leu Met Phe Asn Asn Leu Thr
            580                 585                 590
Leu Gly Gln Asn Ala Val Met Asp Tyr Ser Gln Phe Ser Asn Leu Thr
        595                 600                 605
Ile Gln Gly Asp Phe Ile Asn Asn Gln Gly Thr Ile Asn Tyr Leu Val
    610                 615                 620
Arg Gly Gly Lys Val Ala Thr Leu Asn Val Gly Asn Ala Ala Ala Met
```

```
            625                 630                 635                 640
Met Phe Asn Asn Asp Ile Asp Ser Ala Thr Gly Phe Tyr Lys Pro Leu
                    645                 650                 655

Ile Lys Ile Asn Ser Ala Gln Asp Leu Ile Lys Asn Thr Glu His Val
                    660                 665                 670

Leu Leu Lys Ala Lys Ile Ile Gly Tyr Gly Asn Val Ser Thr Gly Thr
                    675                 680                 685

Asn Gly Ile Ser Asn Val Asn Leu Glu Glu Gln Phe Lys Glu Arg Leu
                    690                 695                 700

Ala Leu Tyr Asn Asn Asn Asn Arg Met Asp Thr Cys Val Val Arg Asn
705                 710                 715                 720

Thr Asp Asp Ile Lys Ala Cys Gly Met Ala Ile Gly Asn Gln Ser Met
                    725                 730                 735

Val Asn Asn Pro Asp Asn Tyr Lys Tyr Leu Ile Gly Lys Ala Trp Lys
                    740                 745                 750

Asn Ile Gly Ile Ser Lys Thr Ala Asn Gly Ser Lys Ile Ser Val Tyr
                    755                 760                 765

Tyr Leu Gly Asn Ser Thr Pro Thr Glu Asn Gly Gly Asn Thr Thr Asn
                    770                 775                 780

Leu Pro Thr Asn Thr Thr Asn Asn Ala Arg Phe Ala Ser Tyr Ala Leu
785                 790                 795                 800

Ile Lys Asn Ala Pro Phe Ala His Ser Ala Thr Pro Asn Leu Val Ala
                    805                 810                 815

Ile Asn Gln His Asp Phe Gly Thr Ile Glu Ser Val Phe Glu Leu Ala
                    820                 825                 830

Asn Arg Ser Lys Asp Ile Asp Thr Leu Tyr Ala Asn Ser Gly Ala Gln
                    835                 840                 845

Gly Arg Asp Leu Leu Gln Thr Leu Leu Ile Asp Ser His Asp Ala Gly
                    850                 855                 860

Tyr Ala Arg Thr Met Ile Asp Ala Thr Ser Ala Asn Glu Ile Thr Lys
865                 870                 875                 880

Gln Leu Asn Thr Ala Thr Thr Leu Asn Asn Ile Ala Ser Leu Glu
                    885                 890                 895

His Lys Thr Ser Ser Leu Gln Thr Leu Ser Leu Ser Asn Ala Met Ile
                    900                 905                 910

Leu Asn Ser Arg Leu Val Asn Leu Ser Arg Arg His Thr Asn Asn Ile
                    915                 920                 925

Asp Ser Phe Ala Lys Arg Leu Gln Ala Leu Lys Asp Gln Arg Phe Ala
                    930                 935                 940

Ser Leu Glu Ser Ala Ala Glu Val Leu Tyr Gln Phe Ala
945                 950                 955

<210> SEQ ID NO 4
<211> LENGTH: 1293
<212> TYPE: PRT
<213> ORGANISM: Helicobacter pylori strain G27

<400> SEQUENCE: 4

Met Glu Ile Gln Gln Thr His Arg Lys Met Asn Arg Pro Leu Val Ser
1               5                   10                  15

Leu Val Leu Ala Gly Ala Leu Ile Ser Ala Ile Pro Gln Glu Ser His
                    20                  25                  30

Ala Ala Phe Phe Thr Thr Val Ile Ile Pro Ala Ile Val Gly Gly Ile
                    35                  40                  45
```

```
Ala Thr Gly Thr Ala Val Gly Thr Val Ser Gly Leu Leu Ser Trp Gly
    50                  55                  60
Leu Lys Gln Ala Glu Glu Ala Asn Lys Asn Pro Asp Lys Pro Asp Lys
65                  70                  75                  80
Val Trp Arg Ile Gln Ala Gly Lys Gly Phe Asn Glu Phe Pro Asn Lys
                85                  90                  95
Glu Tyr Asp Leu Tyr Lys Ser Leu Leu Ser Ser Lys Ile Asp Gly Gly
                100                 105                 110
Trp Asp Trp Gly Asn Ala Ala Arg His Tyr Trp Val Lys Gly Gly Gln
            115                 120                 125
Trp Asn Lys Leu Glu Val Asp Met Lys Asp Ala Val Gly Thr Tyr Lys
130                 135                 140
Leu Ser Gly Leu Arg Asn Phe Thr Gly Gly Asp Leu Asp Val Asn Met
145                 150                 155                 160
Gln Lys Ala Thr Leu Arg Leu Gly Gln Phe Asn Gly Asn Ser Phe Thr
                165                 170                 175
Ser Tyr Lys Asp Ala Ala Asp Arg Thr Thr Arg Val Asn Phe Asn Ala
                180                 185                 190
Lys Asn Ile Ser Ile Asp Asn Phe Val Glu Ile Asn Asn Arg Val Gly
            195                 200                 205
Ser Gly Ala Gly Arg Lys Ala Ser Ser Thr Val Leu Thr Leu Gln Ala
    210                 215                 220
Ser Glu Gly Ile Thr Ser Asp Lys Asn Ala Glu Ile Ser Leu Tyr Asp
225                 230                 235                 240
Gly Ala Thr Leu Asn Leu Ala Ser Ser Val Lys Leu Met Gly Asn
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
            275                 280                 285
His Leu Thr Val Gly Asp Lys Asn Ala Ala Gln Ala Gly Ile Ile Ala
        290                 295                 300
Ser Asn Lys Thr His Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asn Thr Pro Ser Gln Ser Gly Thr Lys Asn Asp Lys Asn Glu Ser Ala
            340                 345                 350
Lys Asn Asp Lys Gln Glu Ser Ser Gln Asn Asn Ser Asn Thr Gln Val
        355                 360                 365
Ile Asn Pro Pro Asn Ser Thr Gln Lys Thr Glu Ile Gln Pro Thr Gln
    370                 375                 380
Val Ile Asp Gly Pro Phe Ala Gly Gly Lys Asp Thr Val Val Asn Ile
385                 390                 395                 400
Asn Arg Ile Asn Thr Asn Ala Asp Gly Thr Ile Arg Val Gly Gly Phe
            405                 410                 415
Lys Ala Ser Leu Thr Thr Asn Ala Ala His Leu His Ile Gly Lys Gly
                420                 425                 430
Gly Val Asn Leu Ser Asn Gln Ala Ser Gly Arg Thr Leu Leu Val Glu
            435                 440                 445
Asn Leu Thr Gly Asn Ile Thr Val Asp Gly Pro Leu Arg Val Asn Asn
450                 455                 460
Gln Val Gly Gly Tyr Ala Leu Ala Gly Ser Ser Ala Asn Phe Glu Phe
```

```
            465                 470                 475                 480
Lys Ala Gly Val Asp Thr Lys Asn Gly Thr Ala Thr Phe Asn Asn Asp
                    485                 490                 495
Ile Ser Leu Gly Arg Phe Val Asn Leu Lys Val Asp Ala His Thr Ala
                500                 505                 510
Asn Phe Lys Gly Ile Asp Thr Gly Asn Gly Phe Asn Thr Leu Asp
            515                 520                 525
Phe Ser Gly Val Thr Asp Lys Val Asn Ile Asn Lys Leu Ile Thr Ala
530                 535                 540
Ser Thr Asn Val Ala Val Lys Asn Phe Asn Ile Asn Glu Leu Ile Val
545                 550                 555                 560
Lys Thr Asn Gly Ile Ser Val Gly Glu Tyr Thr His Phe Ser Glu Asp
                565                 570                 575
Ile Gly Ser Gln Ser Arg Ile Asn Thr Val Arg Leu Glu Thr Gly Thr
                580                 585                 590
Arg Ser Ile Phe Ser Gly Gly Val Lys Phe Lys Ser Gly Glu Lys Leu
            595                 600                 605
Val Ile Asp Glu Phe Tyr Tyr Ser Pro Trp Asn Tyr Phe Asp Ala Arg
            610                 615                 620
Asn Val Lys Asn Val Glu Ile Thr Arg Lys Phe Ala Ser Ser Thr Pro
625                 630                 635                 640
Glu Asn Pro Trp Gly Thr Ser Lys Leu Met Phe Asn Asn Leu Thr Leu
                645                 650                 655
Gly Gln Asn Ala Val Met Asp Tyr Ser Gln Phe Ser Asn Leu Thr Ile
                660                 665                 670
Gln Gly Asp Phe Ile Asn Asn Gln Gly Thr Ile Asn Tyr Leu Val Arg
            675                 680                 685
Gly Gly Lys Val Ala Thr Leu Ser Val Gly Asn Ala Ala Ala Met Met
            690                 695                 700
Phe Asn Asn Asp Ile Asp Ser Ala Thr Gly Phe Tyr Lys Pro Leu Ile
705                 710                 715                 720
Lys Ile Asn Ser Ala Gln Asp Leu Ile Lys Asn Thr Glu His Val Leu
                725                 730                 735
Leu Lys Ala Lys Ile Ile Gly Tyr Gly Asn Val Ser Thr Gly Thr Asn
                740                 745                 750
Ser Ile Ser Asn Val Asn Leu Glu Glu Gln Phe Lys Glu Arg Leu Ala
            755                 760                 765
Leu Tyr Asn Asn Asn Asn Arg Met Asp Thr Cys Val Val Arg Asn Thr
    770                 775                 780
Asp Asp Ile Lys Ala Cys Gly Met Ala Ile Gly Asn Gln Ser Met Val
785                 790                 795                 800
Asn Asn Pro Asp Asn Tyr Lys Tyr Leu Ile Gly Lys Ala Trp Lys Asn
                805                 810                 815
Ile Gly Ile Ser Lys Thr Ala Asn Gly Ser Lys Ile Ser Val Tyr Tyr
            820                 825                 830
Leu Gly Asn Ser Thr Pro Thr Glu Asn Gly Gly Asn Thr Thr Asn Leu
            835                 840                 845
Pro Thr Asn Thr Thr Asn Asn Ala Arg Ser Ala Asn Tyr Ala Leu Val
        850                 855                 860
Lys Asn Ala Pro Phe Ala His Ser Ala Thr Pro Asn Leu Val Ala Ile
865                 870                 875                 880
Asn Gln His Asp Phe Gly Thr Ile Glu Ser Val Phe Glu Leu Ala Asn
                885                 890                 895
```

-continued

```
Arg Ser Lys Asp Ile Asp Thr Leu Tyr Thr His Ser Gly Val Gln Gly
            900                 905                 910

Arg Asp Leu Leu Gln Thr Leu Leu Ile Asp Ser His Asp Ala Gly Tyr
            915                 920                 925

Ala Arg Gln Met Ile Asp Asn Thr Ser Thr Gly Glu Ile Thr Lys Gln
            930                 935                 940

Leu Asn Ala Ala Thr Asp Ala Leu Asn Asn Ile Ala Ser Leu Glu His
945                 950                 955                 960

Lys Thr Ser Gly Leu Gln Thr Leu Ser Leu Ser Asn Ala Met Ile Leu
            965                 970                 975

Asn Ser Arg Leu Val Asn Leu Ser Arg Lys His Thr Asn His Ile Asp
            980                 985                 990

Ser Phe Ala Gln Arg Leu Gln Ala Leu Lys Gly Gln Arg Phe Ala Ser
            995                 1000                1005

Leu Glu Ser Ala Ala Glu Val Leu Tyr Gln Phe Ala Pro Lys Tyr
            1010                1015                1020

Glu Lys Pro Thr Asn Val Trp Ala Asn Ala Ile Gly Gly Ala Ser
            1025                1030                1035

Leu Asn Asn Gly Gly Asn Ala Ser Leu Tyr Gly Thr Ser Ala Gly
            1040                1045                1050

Val Asp Ala Tyr Leu Asn Gly Glu Val Glu Ala Ile Val Gly Gly
            1055                1060                1065

Phe Gly Ser Tyr Gly Tyr Ser Ser Phe Ser Asn Arg Ala Asn Ser
            1070                1075                1080

Leu Asn Ser Gly Ala Asn Asn Ala Asn Phe Gly Val Tyr Ser Arg
            1085                1090                1095

Ile Phe Ala Asn Gln His Glu Phe Asp Phe Glu Ala Gln Gly Ala
            1100                1105                1110

Leu Gly Ser Asp Gln Ser Ser Leu Asn Phe Lys Ser Ala Leu Leu
            1115                1120                1125

Gln Asp Leu Asn Gln Ser Tyr His Tyr Leu Ala Tyr Ser Ala Ala
            1130                1135                1140

Thr Arg Ala Ser Tyr Gly Tyr Asp Phe Ala Phe Phe Arg Asn Ala
            1145                1150                1155

Leu Val Leu Lys Pro Ser Val Gly Val Ser Tyr Asn His Leu Gly
            1160                1165                1170

Ser Thr Asn Phe Lys Ser Ser Asn Gln Val Ala Leu Lys Asn
            1175                1180                1185

Gly Ser Ser Ser Gln His Leu Phe Asn Ala Asn Ala Asn Val Glu
            1190                1195                1200

Ala Arg Tyr Tyr Tyr Gly Asp Thr Ser Tyr Phe Tyr Met Asn Ala
            1205                1210                1215

Gly Val Leu Gln Glu Phe Arg Phe Gly Ser Asn Asn Ala Ala
            1220                1225                1230

Ser Leu Asn Thr Phe Lys Val Asn Thr Ala Arg Asn Pro Leu Asn
            1235                1240                1245

Thr His Ala Arg Val Met Met Gly Gly Glu Leu Gln Leu Ala Lys
            1250                1255                1260

Glu Val Phe Leu Asn Leu Gly Val Val Tyr Leu His Asn Leu Ile
            1265                1270                1275

Ser Asn Ile Gly His Phe Ala Ser Asn Leu Gly Met Arg Tyr Ser
            1280                1285                1290
```

<210> SEQ ID NO 5
<211> LENGTH: 1287
<212> TYPE: PRT
<213> ORGANISM: Helicobacter pylori strain 60190

<400> SEQUENCE: 5

```
Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
                20                  25                  30

Ala Ala Phe Phe Thr Thr Val Ile Ile Pro Ala Ile Val Gly Gly Ile
            35                  40                  45

Ala Thr Gly Thr Ala Val Gly Thr Val Ser Gly Leu Leu Gly Trp Gly
        50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Thr His Tyr Trp Ile Lys Gly Gly Gln
        115                 120                 125

Trp Asn Lys Leu Glu Val Asp Met Lys Asp Ala Val Gly Thr Tyr Lys
130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Leu Ile Asp Asn Phe Leu Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Asn Ser Val Lys Leu Asn Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp His Asn Ala Ala Gln Ala Gly Ile Ile Ala
    290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Ala Lys Asn Asp Lys Gln Glu Ser Ser
            340                 345                 350

Gln Asn Asn Ser Asn Thr Gln Val Ile Asn Pro Pro Asn Ser Thr Gln
        355                 360                 365

Lys Thr Glu Val Gln Pro Thr Gln Val Ile Asp Gly Pro Phe Ala Gly
    370                 375                 380
```

```
Gly Lys Asp Thr Val Val Asn Ile Asp Arg Ile Asn Thr Lys Ala Asp
385                 390                 395                 400

Gly Thr Ile Lys Val Gly Gly Phe Lys Ala Ser Leu Thr Thr Asn Ala
            405                 410                 415

Ala His Leu Asn Ile Gly Lys Gly Gly Val Asn Leu Ser Asn Gln Ala
        420                 425                 430

Ser Gly Arg Thr Leu Leu Val Glu Asn Leu Thr Gly Asn Ile Thr Val
    435                 440                 445

Asp Gly Pro Leu Arg Val Asn Asn Gln Val Gly Gly Tyr Ala Leu Ala
450                 455                 460

Gly Ser Ser Ala Asn Phe Glu Phe Lys Ala Gly Val Asp Thr Lys Asn
465                 470                 475                 480

Gly Thr Ala Thr Phe Asn Asn Asp Ile Ser Leu Gly Arg Phe Val Asn
            485                 490                 495

Leu Lys Val Asp Ala His Thr Ala Asn Phe Lys Gly Ile Asp Thr Gly
        500                 505                 510

Asn Gly Gly Phe Asn Thr Leu Asp Phe Ser Gly Val Thr Asn Lys Val
    515                 520                 525

Asn Ile Asn Lys Leu Ile Thr Ala Ser Thr Asn Val Ala Val Lys Asn
530                 535                 540

Phe Asn Ile Asn Glu Leu Ile Val Lys Thr Asn Gly Val Ser Val Gly
545                 550                 555                 560

Glu Tyr Thr His Phe Ser Glu Asp Ile Gly Ser Gln Ser Arg Ile Asn
            565                 570                 575

Thr Val Arg Leu Glu Thr Gly Thr Arg Ser Ile Phe Ser Gly Gly Val
        580                 585                 590

Lys Phe Lys Ser Gly Glu Lys Leu Val Ile Asp Glu Phe Tyr Tyr Ser
    595                 600                 605

Pro Trp Asn Tyr Phe Asp Ala Arg Asn Ile Lys Asn Val Glu Ile Thr
610                 615                 620

Arg Lys Phe Ala Ser Ser Thr Pro Glu Asn Pro Trp Gly Thr Ser Lys
625                 630                 635                 640

Leu Met Phe Asn Asn Leu Thr Leu Gly Gln Asn Ala Val Met Asp Tyr
            645                 650                 655

Ser Gln Phe Ser Asn Leu Thr Ile Gln Gly Asp Phe Ile Asn Asn Gln
        660                 665                 670

Gly Thr Ile Asn Tyr Leu Val Arg Gly Gly Lys Val Ala Thr Leu Asn
    675                 680                 685

Val Gly Asn Ala Ala Ala Met Met Phe Asn Asn Asp Ile Asp Ser Ala
690                 695                 700

Thr Gly Phe Tyr Lys Pro Leu Ile Lys Ile Asn Ser Ala Gln Asp Leu
705                 710                 715                 720

Ile Lys Asn Thr Glu His Val Leu Leu Lys Ala Lys Ile Ile Gly Tyr
            725                 730                 735

Gly Asn Val Ser Thr Gly Thr Asn Gly Ile Ser Asn Val Asn Leu Glu
        740                 745                 750

Glu Gln Phe Lys Glu Arg Leu Ala Leu Tyr Asn Asn Asn Asn Arg Met
    755                 760                 765

Asp Thr Cys Val Val Arg Asn Thr Asp Ile Lys Ala Cys Gly Met
770                 775                 780

Ala Ile Gly Asn Gln Ser Met Val Asn Asn Pro Asp Asn Tyr Lys Tyr
785                 790                 795                 800
```

Leu Ile Gly Lys Ala Trp Lys Asn Ile Gly Ile Ser Lys Thr Ala Asn
                805                 810                 815

Gly Ser Lys Ile Ser Val Tyr Tyr Leu Gly Asn Ser Thr Pro Thr Glu
        820                 825                 830

Asn Gly Gly Asn Thr Thr Asn Leu Pro Thr Asn Thr Thr Asn Asn Ala
        835                 840                 845

Arg Phe Ala Ser Tyr Ala Leu Ile Lys Asn Ala Pro Phe Ala His Ser
    850                 855                 860

Ala Thr Pro Asn Leu Val Ala Ile Asn Gln His Asp Phe Gly Thr Ile
865                 870                 875                 880

Glu Ser Val Phe Glu Leu Ala Asn Arg Ser Lys Asp Ile Asp Thr Leu
                885                 890                 895

Tyr Ala Asn Ser Gly Ala Gln Gly Arg Asp Leu Leu Gln Thr Leu Leu
                900                 905                 910

Ile Asp Ser His Asp Ala Gly Tyr Ala Arg Thr Met Ile Asp Ala Thr
            915                 920                 925

Ser Ala Asn Glu Ile Thr Lys Gln Leu Asn Thr Ala Thr Thr Thr Leu
        930                 935                 940

Asn Asn Ile Ala Ser Leu Glu His Lys Thr Ser Ser Leu Gln Thr Leu
945                 950                 955                 960

Ser Leu Ser Asn Ala Met Ile Leu Asn Ser Arg Leu Val Asn Leu Ser
                965                 970                 975

Arg Arg His Thr Asn Asn Ile Asp Ser Phe Ala Lys Arg Leu Gln Ala
                980                 985                 990

Leu Lys Asp Gln Arg Phe Ala Ser Leu Glu Ser Ala Ala Glu Val Leu
            995                 1000                1005

Tyr Gln Phe Ala Pro Lys Tyr Glu Lys Pro Thr Asn Val Trp Ala
    1010                1015                1020

Asn Ala Ile Gly Gly Ala Ser Leu Asn Asn Gly Gly Asn Ala Ser
    1025                1030                1035

Leu Tyr Gly Thr Ser Ala Gly Val Asp Ala Tyr Leu Asn Gly Gln
    1040                1045                1050

Val Glu Ala Ile Val Gly Gly Phe Gly Ser Tyr Gly Tyr Ser Ser
    1055                1060                1065

Phe Asn Asn Gln Ala Asn Ser Leu Asn Ser Gly Ala Asn Asn Thr
    1070                1075                1080

Asn Phe Gly Val Tyr Ser Arg Ile Phe Ala Asn Gln His Glu Phe
    1085                1090                1095

Asp Phe Glu Ala Gln Gly Ala Leu Gly Ser Asp Gln Ser Ser Leu
    1100                1105                1110

Asn Phe Lys Ser Ala Leu Leu Arg Asp Leu Asn Gln Ser Tyr Asn
    1115                1120                1125

Tyr Leu Ala Tyr Ser Ala Ala Thr Arg Ala Ser Tyr Gly Tyr Asp
    1130                1135                1140

Phe Ala Phe Phe Arg Asn Ala Leu Val Leu Lys Pro Ser Val Gly
    1145                1150                1155

Val Ser Tyr Asn His Leu Gly Ser Thr Asn Phe Lys Ser Asn Ser
    1160                1165                1170

Thr Asn Lys Val Ala Leu Ser Asn Gly Ser Ser Gln His Leu
    1175                1180                1185

Phe Asn Ala Ser Ala Asn Val Glu Ala Arg Tyr Tyr Tyr Gly Asp
    1190                1195                1200

Thr Ser Tyr Phe Tyr Met Asn Ala Gly Val Leu Gln Glu Phe Ala

```
                    1205                1210                1215

Asn Phe Gly Ser Ser Asn Ala Val Ser Leu Asn Thr Phe Lys Val
                1220                1225                1230

Asn Ala Thr Arg Asn Pro Leu Asn Thr His Ala Arg Val Met Met
            1235                1240                1245

Gly Gly Glu Leu Lys Leu Ala Lys Glu Val Phe Leu Asn Leu Gly
        1250                1255                1260

Val Val Tyr Leu His Asn Leu Ile Ser Asn Ile Gly His Phe Ala
    1265                1270                1275

Ser Asn Leu Gly Met Arg Tyr Ser Phe
        1280                1285

<210> SEQ ID NO 6
<211> LENGTH: 1290
<212> TYPE: PRT
<213> ORGANISM: Helicobacter pylori strain 26695

<400> SEQUENCE: 6

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
            20                  25                  30

Ala Ala Phe Phe Thr Thr Val Ile Ile Pro Ala Ile Val Gly Gly Ile
        35                  40                  45

Ala Thr Gly Ala Ala Val Gly Thr Val Ser Gly Leu Leu Gly Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Arg Ser Leu Leu Ser Ser Lys Ile Asp Gly Gly
            100                 105                 110

Trp Asp Trp Gly Asn Ala Ala Thr His Tyr Trp Val Lys Gly Gly Gln
        115                 120                 125

Trp Asn Lys Leu Glu Val Asp Met Lys Asp Ala Val Gly Thr Tyr Asn
    130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Leu Ile Asp Asn Phe Leu Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Asn Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285
```

His Leu Thr Val Gly Asp His Asn Ala Ala Gln Ala Gly Ile Ile Ala
290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Lys
            325                 330                 335

Asp Lys Pro Ser Asn Thr Thr Gln Asn Asn Ala Asn Asn Gln Gln
        340                 345                 350

Asn Ser Ala Gln Asn Asn Ser Asn Thr Gln Val Ile Asn Pro Pro Asn
            355                 360                 365

Ser Ala Gln Lys Thr Glu Ile Gln Pro Thr Gln Val Ile Asp Gly Pro
370                 375                 380

Phe Ala Gly Gly Lys Asp Thr Val Val Asn Ile Asp Arg Ile Asn Thr
385                 390                 395                 400

Asn Ala Asp Gly Thr Ile Lys Val Gly Gly Tyr Lys Ala Ser Leu Thr
            405                 410                 415

Thr Asn Ala Ala His Leu His Ile Gly Lys Gly Gly Ile Asn Leu Ser
            420                 425                 430

Asn Gln Ala Ser Gly Arg Thr Leu Leu Val Glu Asn Leu Thr Gly Asn
        435                 440                 445

Ile Thr Val Asp Gly Pro Leu Arg Val Asn Asn Gln Val Gly Gly Tyr
    450                 455                 460

Ala Leu Ala Gly Ser Ser Ala Asn Phe Glu Phe Lys Ala Gly Thr Asp
465                 470                 475                 480

Thr Lys Asn Gly Thr Ala Thr Phe Asn Asn Asp Ile Ser Leu Gly Arg
            485                 490                 495

Phe Val Asn Leu Lys Val Asp Ala His Thr Ala Asn Phe Lys Gly Ile
            500                 505                 510

Asp Thr Gly Asn Gly Phe Asn Thr Leu Asp Phe Ser Gly Val Thr
        515                 520                 525

Gly Lys Val Asn Ile Asn Lys Leu Ile Thr Ala Ser Thr Asn Val Ala
530                 535                 540

Val Lys Asn Phe Asn Ile Asn Glu Leu Val Val Lys Thr Asn Gly Val
545                 550                 555                 560

Ser Val Gly Glu Tyr Thr His Phe Ser Glu Asp Ile Gly Ser Gln Ser
            565                 570                 575

Arg Ile Asn Thr Val Arg Leu Glu Thr Gly Thr Arg Ser Ile Phe Ser
        580                 585                 590

Gly Gly Val Lys Phe Lys Ser Gly Glu Lys Leu Val Ile Asp Glu Phe
        595                 600                 605

Tyr Tyr Ser Pro Trp Asn Tyr Phe Asp Ala Arg Asn Ile Lys Asn Val
    610                 615                 620

Glu Ile Thr Arg Lys Phe Ala Ser Ser Thr Pro Glu Asn Pro Trp Gly
625                 630                 635                 640

Thr Ser Lys Leu Met Phe Asn Asn Leu Thr Leu Gly Gln Asn Ala Val
            645                 650                 655

Met Asp Tyr Ser Gln Phe Ser Asn Leu Thr Ile Gln Gly Asp Phe Ile
            660                 665                 670

Asn Asn Gln Gly Thr Ile Asn Tyr Leu Val Arg Gly Gly Gln Val Ala
        675                 680                 685

Thr Leu Asn Val Gly Asn Ala Ala Ala Met Phe Phe Ser Asn Val
690                 695                 700

Asp Ser Ala Thr Gly Phe Tyr Gln Pro Leu Met Lys Ile Asn Ser Ala

-continued

```
            705                 710                 715                 720
        Gln Asp Leu Ile Lys Asn Lys Glu His Val Leu Leu Lys Ala Lys Ile
                        725                 730                 735
        Ile Gly Tyr Gly Asn Val Ser Leu Gly Thr Asn Ser Ile Ser Asn Val
                        740                 745                 750
        Asn Leu Ile Glu Gln Phe Lys Glu Arg Leu Ala Leu Tyr Asn Asn Asn
                        755                 760                 765
        Asn Arg Met Asp Ile Cys Val Val Arg Asn Thr Asp Asp Ile Lys Ala
                        770                 775                 780
        Cys Gly Thr Ala Ile Gly Asn Gln Ser Met Val Asn Asn Pro Asp Asn
        785                 790                 795                 800
        Tyr Lys Tyr Leu Ile Gly Lys Ala Trp Lys Asn Ile Gly Ile Ser Lys
                        805                 810                 815
        Thr Ala Asn Gly Ser Lys Ile Ser Val Tyr Tyr Leu Gly Asn Ser Thr
                        820                 825                 830
        Pro Thr Glu Lys Gly Gly Asn Thr Thr Asn Leu Pro Thr Asn Thr Thr
                        835                 840                 845
        Ser Asn Val Arg Ser Ala Asn Asn Ala Leu Ala Gln Asn Ala Pro Phe
        850                 855                 860
        Ala Gln Pro Ser Ala Thr Pro Asn Leu Val Ala Ile Asn Gln His Asp
        865                 870                 875                 880
        Phe Gly Thr Ile Glu Ser Val Phe Glu Leu Ala Asn Arg Ser Lys Asp
                        885                 890                 895
        Ile Asp Thr Leu Tyr Ala Asn Ser Gly Ala Gln Gly Arg Asp Leu Leu
                        900                 905                 910
        Gln Thr Leu Leu Ile Asp Ser His Asp Ala Gly Tyr Ala Arg Gln Met
                        915                 920                 925
        Ile Asp Asn Thr Ser Thr Gly Glu Ile Thr Lys Gln Leu Asn Ala Ala
                        930                 935                 940
        Thr Thr Thr Leu Asn Asn Ile Ala Ser Leu Glu His Lys Thr Ser Ser
        945                 950                 955                 960
        Leu Gln Thr Leu Ser Leu Ser Asn Ala Met Ile Leu Asn Ser Arg Leu
                        965                 970                 975
        Val Asn Leu Ser Arg Arg His Thr Asn Asn Ile Asp Ser Phe Ala Gln
                        980                 985                 990
        Arg Leu Gln Ala Leu Lys Asp Gln Lys Phe Ala Ser Leu Glu Ser Ala
                        995                 1000                1005
        Ala Glu Val Leu Tyr Gln Phe Ala Pro Lys Tyr Glu Lys Pro Thr
                        1010                1015                1020
        Asn Val Trp Ala Asn Ala Ile Gly Gly Thr Ser Leu Asn Asn Gly
                        1025                1030                1035
        Gly Asn Ala Ser Leu Tyr Gly Thr Ser Ala Gly Val Asp Ala Tyr
                        1040                1045                1050
        Leu Asn Gly Glu Val Glu Ala Ile Val Gly Gly Phe Gly Ser Tyr
                        1055                1060                1065
        Gly Tyr Ser Ser Phe Asn Asn Gln Ala Asn Ser Leu Asn Ser Gly
                        1070                1075                1080
        Ala Asn Asn Thr Asn Phe Gly Val Tyr Ser Arg Ile Phe Ala Asn
                        1085                1090                1095
        Gln His Glu Phe Asp Phe Glu Ala Gln Gly Ala Leu Gly Ser Asp
                        1100                1105                1110
        Gln Ser Ser Leu Asn Phe Lys Ser Ala Leu Leu Arg Asp Leu Asn
                        1115                1120                1125
```

```
Gln Ser Tyr Asn Tyr Leu Ala Tyr Ser Ala Ala Thr Arg Ala Ser
    1130                1135                1140

Tyr Gly Tyr Asp Phe Ala Phe Phe Arg Asn Ala Leu Val Leu Lys
    1145                1150                1155

Pro Ser Val Gly Val Ser Tyr Asn His Leu Gly Ser Thr Asn Phe
    1160                1165                1170

Lys Ser Asn Ser Asn Gln Val Ala Leu Lys Asn Gly Ser Ser Ser
    1175                1180                1185

Gln His Leu Phe Asn Ala Ser Ala Asn Val Glu Ala Arg Tyr Tyr
    1190                1195                1200

Tyr Gly Asp Thr Ser Tyr Phe Tyr Met Asn Ala Gly Val Leu Gln
    1205                1210                1215

Glu Phe Ala Asn Phe Gly Ser Ser Asn Ala Val Ser Leu Asn Thr
    1220                1225                1230

Phe Lys Val Asn Ala Ala His Asn Pro Leu Ser Thr His Ala Arg
    1235                1240                1245

Val Met Met Gly Gly Glu Leu Lys Leu Ala Lys Glu Val Phe Leu
    1250                1255                1260

Asn Leu Gly Phe Val Tyr Leu His Asn Leu Ile Ser Asn Ile Gly
    1265                1270                1275

His Phe Ala Ser Asn Leu Gly Met Arg Tyr Ser Phe
    1280                1285                1290

<210> SEQ ID NO 7
<211> LENGTH: 1288
<212> TYPE: PRT
<213> ORGANISM: Helicobacter pylori strain J99

<400> SEQUENCE: 7

Met Glu Ile Gln Gln Thr His Arg Lys Ile Asn Arg Pro Leu Val Ser
1               5                   10                  15

Leu Val Leu Ala Gly Ala Leu Ile Ser Ala Ile Pro Gln Glu Ser His
            20                  25                  30

Ala Ala Phe Phe Thr Thr Val Ile Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Trp Asn Lys Leu Glu Val Asp Met Lys Asp Ala Val Gly Thr Tyr Lys
    130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asn Phe Asn Ala
            180                 185                 190

Lys Asn Ile Ser Ile Asp Asn Phe Val Glu Ile Asn Asn Arg Val Gly
```

-continued

```
            195                 200                 205
Ser Gly Ala Gly Arg Lys Ala Ser Ser Thr Val Leu Thr Leu Gln Ala
210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Asn Ser Val Lys Leu Asn Gly Asn
                    245                 250                 255

Val Trp Met Gly Arg Leu Gln Tyr Val Gly Ala Tyr Leu Ala Pro Ser
                260                 265                 270

Tyr Ser Thr Ile Asn Thr Ser Lys Val Gln Gly Glu Val Asp Phe Asn
                275                 280                 285

His Leu Thr Val Gly Asp Gln Asn Ala Ala Gln Ala Gly Ile Ile Ala
290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                    325                 330                 335

Ser Thr Thr Ser Gln Ser Gly Thr Lys Asn Asp Lys Lys Glu Ile Ser
                340                 345                 350

Gln Asn Asn Asn Ser Asn Thr Glu Val Ile Asn Pro Pro Asn Asn Thr
                355                 360                 365

Gln Lys Thr Glu Thr Glu Pro Thr Gln Val Ile Asp Gly Pro Phe Ala
370                 375                 380

Gly Gly Lys Asp Thr Val Val Asn Ile Phe His Leu Asn Thr Lys Ala
385                 390                 395                 400

Asp Gly Thr Ile Lys Val Gly Gly Phe Lys Ala Ser Leu Thr Thr Asn
                    405                 410                 415

Ala Ala His Leu Asn Ile Gly Lys Gly Val Asn Leu Ser Asn Gln
                420                 425                 430

Ala Ser Gly Arg Thr Leu Leu Val Glu Asn Leu Thr Gly Asn Ile Thr
                435                 440                 445

Val Asp Gly Pro Leu Arg Val Asn Asn Gln Val Gly Gly Tyr Ala Leu
450                 455                 460

Ala Gly Ser Ser Ala Asn Phe Glu Phe Lys Ala Gly Val Asp Thr Lys
465                 470                 475                 480

Asn Gly Thr Ala Thr Phe Asn Asn Asp Ile Ser Leu Gly Arg Phe Val
                    485                 490                 495

Asn Leu Lys Val Asp Ala His Thr Ala Asn Phe Lys Gly Ile Asp Thr
                500                 505                 510

Gly Asn Gly Gly Phe Asn Thr Leu Asp Phe Ser Gly Val Thr Asp Lys
                515                 520                 525

Val Asn Ile Asn Lys Leu Ile Thr Ala Ser Thr Asn Val Ala Val Lys
                530                 535                 540

Asn Phe Asn Ile Asn Glu Leu Ile Val Lys Thr Asn Gly Ile Ser Val
545                 550                 555                 560

Gly Glu Tyr Thr His Phe Ser Glu Asp Ile Gly Ser Gln Ser Arg Ile
                    565                 570                 575

Asn Thr Val Arg Leu Glu Thr Gly Thr Arg Ser Ile Phe Ser Gly Gly
                580                 585                 590

Val Lys Phe Lys Ser Gly Glu Lys Leu Val Ile Asn Asp Phe Tyr Tyr
                595                 600                 605

Ser Pro Trp Asn Tyr Phe Asp Ala Arg Asn Val Lys Asn Val Glu Ile
610                 615                 620
```

```
Thr Arg Lys Phe Ala Ser Ser Thr Pro Glu Asn Pro Trp Gly Thr Ser
625                 630                 635                 640

Lys Leu Met Phe Asn Asn Leu Thr Leu Gly Gln Asn Ala Val Met Asp
            645                 650                 655

Tyr Ser Gln Phe Ser Asn Leu Thr Ile Gln Gly Asp Phe Ile Asn Asn
                660                 665                 670

Gln Gly Thr Ile Asn Tyr Leu Val Arg Gly Gly Lys Val Ala Thr Leu
            675                 680                 685

Asn Val Gly Asn Ala Ala Ala Met Met Phe Asn Asn Asp Ile Asp Ser
690                 695                 700

Ala Thr Gly Phe Tyr Lys Pro Leu Ile Lys Ile Asn Ser Ala Gln Asp
705                 710                 715                 720

Leu Ile Lys Asn Thr Glu His Val Leu Leu Lys Ala Lys Ile Ile Gly
                725                 730                 735

Tyr Gly Asn Val Ser Thr Gly Thr Asn Gly Ile Ser Asn Val Asn Leu
            740                 745                 750

Glu Glu Gln Phe Lys Glu Arg Leu Ala Leu Tyr Asn Asn Asn Asn Arg
                755                 760                 765

Met Asp Thr Cys Val Val Arg Asn Thr Asp Asp Ile Lys Ala Cys Gly
770                 775                 780

Met Ala Ile Gly Asn Gln Ser Met Val Asn Asn Pro Asp Asn Tyr Lys
785                 790                 795                 800

Tyr Leu Ile Gly Lys Ala Trp Arg Asn Ile Gly Ile Ser Lys Thr Ala
            805                 810                 815

Asn Gly Ser Lys Ile Ser Val Tyr Tyr Leu Gly Asn Ser Thr Pro Thr
            820                 825                 830

Glu Asn Gly Gly Asn Thr Thr Asn Leu Pro Thr Asn Thr Thr Asn Asn
            835                 840                 845

Ala His Ser Ala Asn Tyr Ala Leu Val Lys Asn Ala Pro Phe Ala His
            850                 855                 860

Ser Ala Thr Pro Asn Leu Val Ala Ile Asn Gln His Asp Phe Gly Thr
865                 870                 875                 880

Ile Glu Ser Val Phe Glu Leu Ala Asn Arg Ser Lys Asp Ile Asp Thr
                885                 890                 895

Leu Tyr Thr His Ser Gly Ala Gln Gly Arg Asp Leu Leu Gln Thr Leu
            900                 905                 910

Leu Ile Asp Ser His Asp Ala Gly Tyr Ala Arg Gln Met Ile Asp Asn
            915                 920                 925

Thr Ser Thr Gly Glu Ile Thr Lys Gln Leu Asn Ala Ala Thr Asp Ala
930                 935                 940

Leu Asn Asn Val Ala Ser Leu Glu His Lys Gln Ser Gly Leu Gln Thr
945                 950                 955                 960

Leu Ser Leu Ser Asn Ala Met Ile Leu Asn Ser Arg Leu Val Asn Leu
            965                 970                 975

Ser Arg Lys His Thr Asn His Ile Asn Ser Phe Ala Gln Arg Leu Gln
            980                 985                 990

Ala Leu Lys Gly Gln Glu Phe Ala  Ser Leu Glu Ser Ala  Ala Glu Val
            995                 1000                1005

Leu Tyr  Gln Phe Ala Pro Lys  Tyr Glu Lys Pro Thr  Asn Val Trp
    1010                1015                1020

Ala Asn  Ala Ile Gly Gly Ala  Ser Leu Asn Ser Gly  Ser Asn Ala
    1025                1030                1035
```

```
Ser Leu Tyr Gly Thr Ser Ala Gly Val Asp Ala Phe Leu Asn Gly
    1040                1045                1050

Asn Val Glu Ala Ile Val Gly Phe Gly Ser Tyr Gly Tyr Ser
    1055                1060                1065

Ser Phe Ser Asn Gln Ala Asn Ser Leu Asn Ser Gly Ala Asn Asn
    1070                1075                1080

Ala Asn Phe Gly Val Tyr Ser Arg Phe Ala Asn Gln His Glu
    1085                1090                1095

Phe Asp Phe Glu Ala Gln Gly Ala Leu Gly Ser Asp Gln Ser Ser
    1100                1105                1110

Leu Asn Phe Lys Ser Thr Leu Leu Gln Asp Leu Asn Gln Ser Tyr
    1115                1120                1125

Asn Tyr Leu Ala Tyr Ser Ala Thr Ala Arg Ala Ser Tyr Gly Tyr
    1130                1135                1140

Asp Phe Ala Phe Phe Arg Asn Ala Leu Val Leu Lys Pro Ser Val
    1145                1150                1155

Gly Val Ser Tyr Asn His Leu Gly Ser Thr Asn Phe Lys Ser Asn
    1160                1165                1170

Ser Gln Ser Gln Val Ala Leu Lys Asn Gly Ala Ser Ser Gln His
    1175                1180                1185

Leu Phe Asn Ala Asn Ala Asn Val Glu Ala Arg Tyr Tyr Tyr Gly
    1190                1195                1200

Asp Thr Ser Tyr Phe Tyr Leu His Ala Gly Val Leu Gln Glu Phe
    1205                1210                1215

Ala His Phe Gly Ser Asn Asp Val Ala Ser Leu Asn Thr Phe Lys
    1220                1225                1230

Ile Asn Ala Ala Arg Ser Pro Leu Ser Thr Tyr Ala Arg Ala Met
    1235                1240                1245

Met Gly Gly Glu Leu Gln Leu Ala Lys Glu Val Phe Leu Asn Leu
    1250                1255                1260

Gly Val Val Tyr Leu His Asn Leu Ile Ser Asn Ala Ser His Phe
    1265                1270                1275

Ala Ser Asn Leu Gly Met Arg Tyr Ser Phe
    1280                1285

<210> SEQ ID NO 8
<211> LENGTH: 1290
<212> TYPE: PRT
<213> ORGANISM: Helicobacter pylori strain NCTC 11637

<400> SEQUENCE: 8

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
            20                  25                  30

Ala Ala Phe Phe Thr Thr Val Ile Ile Pro Ala Ile Val Gly Gly Ile
        35                  40                  45

Ala Thr Gly Ala Ala Val Gly Thr Val Ser Gly Leu Leu Ser Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Arg Gly Phe Asn Asn Phe Pro His Lys
                85                  90                  95

Glu Tyr Asp Leu Tyr Lys Ser Leu Leu Ser Ser Lys Ile Asp Gly Gly
            100                 105                 110
```

```
Trp Asp Trp Gly Asn Ala Ala Arg His Tyr Trp Val Lys Gly Gly Gln
        115                 120                 125

Trp Asn Lys Leu Glu Val Asp Met Lys Asp Ala Val Gly Thr Tyr Lys
    130                 135                 140

Leu Ser Gly Leu Ile Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
                180                 185                 190

Lys Asn Ile Leu Ile Asp Asn Phe Leu Glu Ile Asn Asn Arg Val Gly
                195                 200                 205

Ser Gly Ala Gly Arg Lys Ala Ser Ser Thr Val Leu Thr Leu Gln Ala
        210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Ser Val Lys Leu Met Gly Asn
                245                 250                 255

Val Trp Met Gly Arg Leu Gln Tyr Val Gly Ala Tyr Leu Ala Pro Ser
        260                 265                 270

Tyr Ser Thr Ile Asn Thr Ser Lys Val Thr Gly Glu Val Asn Phe Asn
    275                 280                 285

His Leu Thr Val Gly Asp His Asn Ala Ala Gln Ala Gly Ile Ile Ala
    290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Lys
                325                 330                 335

Asp Lys Pro Ser Asn Thr Thr Gln Asn Asn Ala Asn Asn Asn Gln Gln
                340                 345                 350

Asn Ser Ala Gln Asn Asn Asn Thr Gln Val Ile Asn Pro Pro Asn
        355                 360                 365

Ser Ala Gln Lys Thr Glu Ile Gln Pro Thr Gln Val Ile Asn Gly Pro
    370                 375                 380

Phe Ala Gly Gly Lys Asp Thr Val Val Asn Ile Asn Arg Ile Asn Thr
385                 390                 395                 400

Asn Ala Asp Gly Thr Ile Arg Val Gly Gly Tyr Lys Ala Ser Leu Thr
                405                 410                 415

Thr Asn Ala Ala His Leu His Ile Gly Lys Gly Gly Ile Asn Leu Ser
                420                 425                 430

Asn Gln Ala Ser Gly Arg Ser Leu Leu Val Glu Asn Leu Thr Gly Asn
        435                 440                 445

Ile Thr Val Asp Gly Pro Leu Arg Val Asn Asn Gln Val Gly Gly Tyr
    450                 455                 460

Ala Leu Ala Gly Ser Asn Ala Asn Phe Glu Phe Lys Ala Gly Thr Asp
465                 470                 475                 480

Thr Lys Asn Gly Thr Ala Thr Phe Asn Asn Asp Ile Ser Leu Gly Arg
                485                 490                 495

Phe Val Asn Leu Lys Val Asp Ala His Thr Ala Asn Phe Lys Gly Ile
                500                 505                 510

Asp Thr Gly Asn Gly Gly Phe Asn Thr Leu Asp Phe Ser Gly Val Thr
            515                 520                 525
```

```
Asp Lys Val Asn Ile Asn Lys Leu Ile Thr Ala Ser Thr Asn Val Ala
    530                 535                 540

Ile Lys Asn Phe Asn Ile Asn Glu Leu Leu Val Lys Thr Asn Gly Val
545                 550                 555                 560

Ser Val Gly Glu Tyr Thr His Phe Ser Glu Asp Ile Gly Ser Gln Ser
                565                 570                 575

Arg Ile Asn Thr Val Arg Leu Glu Thr Gly Thr Arg Ser Ile Phe Ser
            580                 585                 590

Gly Gly Val Lys Phe Lys Ser Gly Glu Lys Leu Val Ile Asp Glu Phe
        595                 600                 605

Tyr Tyr Ser Pro Trp Asn Tyr Phe Asp Ala Arg Asn Ile Lys Asn Val
    610                 615                 620

Glu Ile Thr Arg Lys Phe Ala Ser Ser Thr Pro Glu Asn Pro Trp Gly
625                 630                 635                 640

Thr Ser Lys Leu Met Phe Asn Asn Leu Thr Leu Gly Gln Asn Ala Val
                645                 650                 655

Met Asp Tyr Ser Gln Phe Ser Asn Leu Thr Ile Gln Gly Asp Phe Ile
            660                 665                 670

Asn Asn Gln Gly Thr Ile Asn Tyr Leu Val Arg Gly Gly Lys Val Ala
        675                 680                 685

Thr Leu Asn Val Gly Asn Ala Ala Met Met Phe Asn Asn Asp Ile
    690                 695                 700

Asp Ser Ala Thr Gly Phe Tyr Lys Pro Leu Ile Lys Ile Asn Ser Ala
705                 710                 715                 720

Gln Asp Leu Ile Lys Asn Thr Glu His Val Leu Leu Lys Ala Lys Ile
                725                 730                 735

Ile Gly Tyr Gly Asn Val Ser Thr Gly Thr Asn Gly Ile Ser Asn Val
            740                 745                 750

Asn Leu Glu Glu Gln Phe Lys Glu Arg Leu Ala Leu Tyr Asn Asn Asn
        755                 760                 765

Asn Arg Met Asp Thr Cys Val Val Arg Asn Thr Asp Asp Ile Lys Ala
    770                 775                 780

Cys Gly Met Ala Ile Gly Asn Gln Ser Met Val Asn Asn Pro Asp Asn
785                 790                 795                 800

Tyr Lys Tyr Leu Ile Gly Lys Ala Trp Lys Asn Ile Gly Ile Ser Lys
                805                 810                 815

Thr Ala Asn Gly Ser Lys Ile Ser Val Tyr Tyr Leu Gly Asn Ser Thr
            820                 825                 830

Pro Thr Glu Asn Gly Gly Asn Thr Thr Asn Leu Pro Thr Asn Thr Thr
        835                 840                 845

Asn Asn Ala Arg Ser Ala Asn Tyr Ala Leu Val Lys Asn Ala Pro Phe
    850                 855                 860

Ala His Ser Ala Thr Pro Asn Leu Val Ala Ile Asn Gln His Asp Phe
865                 870                 875                 880

Gly Thr Ile Glu Ser Val Phe Glu Leu Ala Asn Arg Ser Lys Asp Ile
                885                 890                 895

Asp Thr Leu Tyr Thr His Ser Gly Ala Lys Gly Arg Asp Leu Leu Gln
            900                 905                 910

Thr Leu Leu Ile Asp Ser His Asp Ala Gly Tyr Ala Arg Gln Met Ile
        915                 920                 925

Asp Asn Thr Ser Thr Gly Glu Ile Thr Lys Gln Leu Asn Ala Ala Thr
    930                 935                 940

Thr Thr Leu Asn Asn Ile Ala Ser Leu Glu His Lys Thr Ser Ser Leu
```

```
                    945                 950                 955                 960
                Gln Thr Leu Ser Leu Ser Asn Ala Met Ile Leu Asn Ser Arg Leu Val
                            965                 970                 975

Asn Leu Ser Arg Lys His Thr Asn Asn Ile Asp Ser Phe Ala Lys Arg
                            980                 985                 990

Leu Gln Ala Leu Lys Asp Gln Arg Phe Ala Ser Leu Glu Ser Ala Ala
                            995                 1000                1005

Glu Val Leu Tyr Gln Phe Ala Pro Lys Tyr Glu Lys Pro Thr Asn
                        1010                1015                1020

Val Trp Ala Asn Ala Ile Gly Gly Ala Ser Leu Asn Asn Gly Ser
                        1025                1030                1035

Asn Ala Ser Leu Tyr Gly Thr Ser Ala Gly Val Asp Ala Tyr Leu
                        1040                1045                1050

Asn Gly Gln Val Glu Ala Ile Val Gly Gly Phe Gly Ser Tyr Gly
                        1055                1060                1065

Tyr Ser Ser Phe Ser Asn Arg Ala Asn Ser Leu Asn Ser Gly Ala
                        1070                1075                1080

Asn Asn Thr Asn Phe Gly Val Tyr Ser Arg Ile Phe Ala Asn Gln
                        1085                1090                1095

His Glu Phe Asp Phe Glu Ala Gln Gly Ala Leu Gly Ser Asp Gln
                        1100                1105                1110

Ser Ser Leu Asn Phe Lys Ser Ala Leu Leu Gln Asp Leu Asn Gln
                        1115                1120                1125

Ser Tyr Asn Tyr Leu Ala Tyr Ser Ala Ala Thr Arg Ala Ser Tyr
                        1130                1135                1140

Gly Tyr Asp Phe Ala Phe Phe Lys Asn Ala Leu Val Leu Lys Pro
                        1145                1150                1155

Ser Val Gly Val Ser Tyr Asn His Leu Gly Ser Thr Asn Phe Lys
                        1160                1165                1170

Ser Asn Ser Thr Asn Lys Val Ala Leu Ser Asn Gly Ser Ser Ser
                        1175                1180                1185

Gln His Leu Phe Asn Ala Ser Ala Asn Val Glu Ala Arg Tyr Tyr
                        1190                1195                1200

Tyr Gly Asp Thr Ser Tyr Phe Tyr Met Asn Ala Gly Val Leu Gln
                        1205                1210                1215

Glu Phe Ala Asn Phe Gly Ser Ser Asn Ala Val Ser Leu Asn Thr
                        1220                1225                1230

Phe Lys Val Asn Ala Ala Arg Asn Pro Leu Asn Thr His Ala Arg
                        1235                1240                1245

Val Met Met Gly Gly Glu Leu Gln Leu Ala Lys Glu Val Phe Leu
                        1250                1255                1260

Asn Leu Gly Phe Val Tyr Leu His Asn Leu Ile Ser Asn Ile Gly
                        1265                1270                1275

His Phe Ala Ser Asn Leu Gly Met Arg Tyr Ser Phe
                        1280                1285                1290

<210> SEQ ID NO 9
<211> LENGTH: 1296
<212> TYPE: PRT
<213> ORGANISM: Helicobacter pylori P12

<400> SEQUENCE: 9

Met Glu Ile Gln Gln Thr His Arg Lys Ile Asn Arg Pro Leu Val Ser
1               5                   10                  15
```

-continued

Leu Ala Leu Val Gly Ala Leu Val Ser Ile Thr Pro Gln Gln Ser His
              20                  25                  30

Ala Ala Phe Phe Thr Thr Val Ile Ile Pro Ala Ile Val Gly Gly Ile
         35                  40                  45

Ala Ser Gly Ala Ala Val Gly Thr Val Ser Gly Leu Leu Gly Trp Gly
     50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                 85                  90                  95

Glu Tyr Asp Leu Tyr Arg Ser Leu Leu Ser Ser Lys Ile Asp Gly Gly
                100                 105                 110

Trp Asp Trp Gly Asn Ala Ala Thr His Tyr Trp Val Lys Gly Gly Gln
            115                 120                 125

Trp Asn Lys Leu Glu Val Asp Met Lys Asp Ala Val Gly Thr Tyr Asn
        130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Ser Ile Asp Asn Phe Leu Glu Ile Asn Asn Arg Val Gly
        195                 200                 205

Ser Gly Ala Gly Arg Lys Ala Ser Ser Thr Val Leu Thr Leu Gln Ala
210                 215                 220

Ser Glu Gly Ile Thr Ser Ser Lys Asn Ala Glu Ile Ser Leu Tyr Asp
225                 230                 235                 240

Gly Ala Thr Leu Asn Leu Ala Ser Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp Arg Asn Ala Ala Gln Ala Gly Ile Ile Ala
290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Ala Lys Asn Asp Lys Asn Glu Ser Ala
            340                 345                 350

Lys Asn Asp Lys Gln Glu Ser Ser Gln Asn Asn Ser Asn Thr Gln Val
        355                 360                 365

Ile Asn Pro Pro Asn Ser Ala Gln Lys Thr Glu Val Gln Pro Thr Gln
    370                 375                 380

Val Ile Asp Gly Pro Phe Ala Gly Gly Lys Asp Thr Val Val Asn Ile
385                 390                 395                 400

Asn Arg Ile Asn Thr Asn Ala Asp Gly Thr Ile Arg Val Gly Gly Tyr
                405                 410                 415

Lys Ala Ser Leu Thr Thr Asn Ala Ala His Leu His Ile Gly Lys Gly
            420                 425                 430

Gly Val Asn Leu Ser Asn Gln Ala Ser Gly Arg Thr Leu Leu Val Glu

```
            435                 440                 445
Asn Leu Thr Gly Asn Ile Thr Val Asp Gly Pro Leu Arg Val Asn Asn
    450                 455                 460

Gln Val Gly Gly Tyr Ala Leu Ala Gly Ser Ser Ala Asn Phe Glu Phe
465                 470                 475                 480

Lys Ala Gly Thr Asp Thr Lys Asn Gly Thr Ala Thr Phe Asn Asn Asp
                485                 490                 495

Ile Ser Leu Gly Arg Phe Val Asn Leu Lys Val Asp Ala His Thr Ala
                500                 505                 510

Asn Phe Lys Gly Ile Asp Thr Gly Asn Gly Gly Phe Asn Thr Leu Asp
            515                 520                 525

Phe Ser Gly Val Thr Asp Lys Val Asn Ile Asn Lys Leu Ile Thr Ala
        530                 535                 540

Ser Thr Asn Val Ala Ile Lys Asn Phe Asn Ile Asn Glu Leu Leu Val
545                 550                 555                 560

Lys Thr Asn Gly Val Ser Val Gly Glu Tyr Thr His Phe Ser Glu Asp
                565                 570                 575

Ile Gly Ser Gln Ser Arg Ile Asn Thr Val Arg Leu Glu Thr Gly Thr
            580                 585                 590

Arg Ser Ile Phe Ser Gly Gly Val Lys Phe Lys Gly Gly Glu Lys Leu
        595                 600                 605

Val Ile Asn Asp Phe Tyr Tyr Ala Pro Trp Asn Tyr Phe Asp Ala Arg
610                 615                 620

Asn Ile Lys Asn Val Glu Ile Thr Asn Lys Leu Ala Phe Gly Pro Gln
625                 630                 635                 640

Gly Ser Pro Trp Gly Thr Ser Lys Leu Met Phe Asn Asn Leu Thr Leu
                645                 650                 655

Gly Gln Asn Ala Val Met Asp Tyr Ser Gln Phe Ser Asn Leu Thr Ile
            660                 665                 670

Gln Gly Asp Phe Val Asn Asn Gln Gly Thr Ile Asn Tyr Leu Val Arg
        675                 680                 685

Gly Gly Gln Val Ala Thr Leu Asn Val Gly Asn Ala Ala Ala Met Phe
    690                 695                 700

Phe Asn Asn Asn Val Asp Ser Ala Thr Gly Phe Tyr Gln Pro Leu Met
705                 710                 715                 720

Lys Ile Asn Ser Ala Gln Asp Leu Ile Lys Asn Lys Glu His Val Leu
                725                 730                 735

Leu Lys Ala Lys Ile Ile Gly Tyr Gly Asn Val Ser Ala Gly Thr Asn
            740                 745                 750

Ser Ile Ser Asn Val Asn Leu Ile Glu Gln Phe Lys Glu Arg Leu Ala
        755                 760                 765

Leu Tyr Glu His Asn Asn Arg Met Asp Ile Cys Val Val Arg Asn Thr
    770                 775                 780

Asp Asp Ile Lys Ala Cys Gly Thr Ala Ile Gly Asn Gln Ser Met Val
785                 790                 795                 800

Asn Asn Pro Asp Asn Tyr Lys Tyr Leu Ile Gly Lys Ala Trp Lys Asn
                805                 810                 815

Ile Gly Ile Ser Lys Thr Ala Asn Gly Ser Lys Ile Ser Val His Tyr
            820                 825                 830

Leu Gly Asn Ser Thr Pro Thr Glu Asn Ser Gly Asn Thr Thr Asn Leu
        835                 840                 845

Pro Thr Asn Thr Thr Ser Asn Ala Arg Ser Ala Lys Asn Ala Leu Ala
    850                 855                 860
```

```
Gln Asn Ala Pro Phe Ala Gln Pro Ser Ala Thr Pro Ser Leu Val Ala
865                 870                 875                 880

Ile Asn Gln His Asp Phe Gly Thr Ile Glu Ser Val Phe Glu Leu Ala
            885                 890                 895

Asn Arg Ser Lys Asp Ile Asp Thr Leu Tyr Thr His Ser Gly Ala Gln
        900                 905                 910

Gly Arg Asn Leu Leu Gln Thr Leu Leu Ile Asp Ser His Asp Ala Gly
    915                 920                 925

Tyr Ala Arg Gln Met Ile Asp Asn Thr Ser Thr Gly Glu Ile Ile Lys
930                 935                 940

Gln Leu Asn Ala Ala Thr Thr Leu Asn Asn Val Ala Ser Leu Glu
945                 950                 955                 960

His Lys Gln Ser Gly Leu Gln Thr Leu Ser Leu Ser Asn Ala Met Ile
                965                 970                 975

Leu Asn Ser Arg Leu Val Asn Leu Ser Arg Arg His Thr Asn Asn Ile
            980                 985                 990

Asp Ser Phe Ala Gln Arg Leu Gln  Ala Leu Lys Asp Gln  Lys Phe Ala
        995                 1000                1005

Ser Leu  Glu Ser Ala Ala Glu  Val Leu Tyr Gln Phe  Ala Pro Lys
    1010                1015                1020

Tyr Glu  Lys Pro Thr Asn Val  Trp Ala Asn Ala Ile  Gly Gly Thr
    1025                1030                1035

Ser Leu  Asn Asn Gly Gly Asn  Ala Ser Leu Tyr Gly  Thr Ser Ala
    1040                1045                1050

Gly Val  Asp Ala Tyr Leu Asn  Gly Glu Val Glu Ala  Ile Val Gly
    1055                1060                1065

Gly Phe  Gly Ser Tyr Gly Tyr  Ser Ser Phe Ser Asn  Gln Ala Asn
    1070                1075                1080

Ser Leu  Asn Ser Gly Ala Asn  Asn Thr Asn Phe Gly  Val Tyr Ser
    1085                1090                1095

Arg Leu  Phe Ala Asn Gln His  Glu Phe Asp Phe Glu  Ala Gln Gly
    1100                1105                1110

Ala Leu  Gly Ser Asp Gln Ser  Ser Leu Asn Phe Lys  Ser Ala Leu
    1115                1120                1125

Leu Arg  Asp Leu Asn Gln Ser  Tyr Asn Tyr Leu Ala  Tyr Ser Ala
    1130                1135                1140

Ala Thr  Arg Ala Ser Tyr Gly  Tyr Asp Phe Ala Phe  Phe Arg Asn
    1145                1150                1155

Ala Leu  Val Leu Lys Pro Ser  Val Gly Val Ser Tyr  Asn His Leu
    1160                1165                1170

Gly Ser  Thr Asn Phe Lys Ser  Asn Ser Thr Asn Gln  Val Ala Leu
    1175                1180                1185

Lys Asn  Gly Ser Ser Ser Gln  His Leu Phe Asn Ala  Ser Ala Asn
    1190                1195                1200

Val Glu  Ala Arg Tyr Tyr Tyr  Gly Asp Thr Ser Tyr  Phe Tyr Met
    1205                1210                1215

Asn Ala  Gly Val Leu Gln Glu  Phe Ala Asn Phe Gly  Ser Ser Asn
    1220                1225                1230

Ala Val  Ser Leu Asn Thr Phe  Lys Val Asn Ala Ala  Arg Asn Pro
    1235                1240                1245

Leu Asn  Thr His Ala Arg Val  Met Met Gly Gly Glu  Leu Lys Leu
    1250                1255                1260
```

Ala Lys Glu Val Phe Leu Asn Leu Gly Phe Val Tyr Leu His Asn
1265                1270                1275

Leu Ile Ser Asn Ile Gly His Phe Ala Ser Asn Leu Gly Met Arg
1280                1285                1290

Tyr Ser Phe
1295

<210> SEQ ID NO 10
<211> LENGTH: 1291
<212> TYPE: PRT
<213> ORGANISM: Helicobacter pylori

<400> SEQUENCE: 10

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
                20                  25                  30

Ala Ala Phe Phe Thr Thr Val Ile Ile Pro Ala Ile Val Gly Gly Ile
            35                  40                  45

Ala Thr Gly Ala Ala Val Gly Thr Val Ser Gly Leu Leu Gly Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Arg His Tyr Trp Val Lys Asp Gly Gln
        115                 120                 125

Trp Asn Lys Leu Glu Val Asp Met Gln Asn Ala Val Gly Thr Tyr Asn
    130                 135                 140

Leu Ser Gly Leu Ile Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Leu Ile Asp Asn Phe Leu Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Arg Glu Asn Ala Glu Ile Ser Leu Tyr Asp
225                 230                 235                 240

Gly Ala Thr Leu Asn Leu Ala Ser Asn Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp His Asn Ala Ala Gln Ala Gly Ile Ile Ala
    290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

-continued

```
Asp Lys Pro Ser Asn Thr Thr Gln Asn Asn Ala Lys Asn Asp Lys Gln
            340                 345                 350

Glu Ser Ser Gln Asn Asn Ser Asn Thr Gln Val Ile Asn Pro Pro Asn
        355                 360                 365

Ser Ala Gln Lys Thr Glu Ile Gln Pro Thr Gln Val Ile Asp Gly Pro
    370                 375                 380

Phe Ala Gly Gly Lys Asn Thr Val Val Asn Ile Asn Arg Ile Asn Thr
385                 390                 395                 400

Asn Ala Asp Gly Thr Ile Arg Val Gly Gly Phe Lys Ala Ser Leu Thr
                405                 410                 415

Thr Asn Ala Ala His Leu His Ile Gly Lys Gly Ile Asn Leu Ser
            420                 425                 430

Asn Gln Ala Ser Gly Arg Ser Leu Leu Val Glu Asn Leu Thr Gly Asn
        435                 440                 445

Ile Thr Val Asp Gly Pro Leu Arg Val Asn Asn Gln Val Gly Gly Tyr
    450                 455                 460

Ala Leu Ala Gly Ser Ser Ala Asn Phe Glu Phe Lys Ala Gly Thr Asp
465                 470                 475                 480

Thr Lys Asn Gly Thr Ala Thr Phe Asn Asn Asp Ile Ser Leu Gly Arg
                485                 490                 495

Phe Val Asn Leu Lys Val Asp Ala His Thr Ala Asn Phe Lys Gly Ile
        500                 505                 510

Asp Thr Gly Asn Gly Phe Asn Thr Leu Asp Phe Ser Gly Val Thr
    515                 520                 525

Asn Lys Val Asn Ile Asn Lys Leu Ile Thr Ala Ser Thr Asn Val Ala
530                 535                 540

Val Lys Asn Phe Asn Ile Asn Glu Leu Val Val Lys Thr Asn Gly Val
545                 550                 555                 560

Ser Val Gly Glu Tyr Thr His Phe Ser Glu Asp Ile Gly Ser Gln Ser
                565                 570                 575

Arg Ile Asn Thr Val Arg Leu Glu Thr Gly Thr Arg Ser Ile Tyr Ser
        580                 585                 590

Gly Gly Val Lys Phe Lys Gly Gly Glu Lys Leu Val Ile Asn Asp Phe
    595                 600                 605

Tyr Tyr Ala Pro Trp Asn Tyr Phe Asp Ala Arg Asn Ile Lys Asn Val
    610                 615                 620

Glu Ile Thr Asn Lys Leu Ala Phe Gly Pro Gln Gly Ser Pro Trp Gly
625                 630                 635                 640

Thr Ala Lys Leu Met Phe Asn Asn Leu Thr Leu Gly Gln Asn Ala Val
                645                 650                 655

Met Asp Tyr Ser Gln Phe Ser Asn Leu Thr Ile Gln Gly Asp Phe Val
        660                 665                 670

Asn Asn Gln Gly Thr Ile Asn Tyr Leu Val Arg Gly Gly Gln Val Ala
    675                 680                 685

Thr Leu Asn Val Gly Asn Ala Ala Met Phe Phe Ser Asn Asn Val
            690                 695                 700

Asp Ser Ala Thr Gly Phe Tyr Gln Pro Leu Met Lys Ile Asn Ser Ala
705                 710                 715                 720

Gln Asp Leu Ile Lys Asn Lys Glu His Val Leu Leu Lys Ala Lys Ile
                725                 730                 735

Ile Gly Tyr Gly Asn Val Ser Ala Gly Thr Asp Ser Ile Ala Asn Val
        740                 745                 750
```

-continued

```
Asn Leu Ile Glu Gln Phe Lys Glu Arg Leu Ala Leu Tyr Asn Asn Asn
        755                 760                 765

Asn Arg Met Asp Ile Cys Val Val Arg Asn Thr Asp Asp Ile Lys Ala
    770                 775                 780

Cys Gly Thr Ala Ile Gly Asn Gln Ser Met Val Asn Asn Pro Glu Asn
785                 790                 795                 800

Tyr Lys Tyr Leu Glu Gly Lys Ala Trp Lys Asn Ile Gly Ile Ser Lys
                805                 810                 815

Thr Ala Asn Gly Ser Lys Ile Ser Val His Tyr Leu Gly Asn Ser Thr
            820                 825                 830

Pro Thr Glu Asn Gly Gly Asn Thr Thr Asn Leu Pro Thr Asn Thr Thr
        835                 840                 845

Asn Lys Val Arg Phe Ala Ser Tyr Ala Leu Ile Lys Asn Ala Pro Phe
    850                 855                 860

Ala Arg Tyr Ser Ala Thr Pro Asn Leu Val Ala Ile Asn Gln His Asp
865                 870                 875                 880

Phe Gly Thr Ile Glu Ser Val Phe Glu Leu Ala Asn Arg Ser Asn Asp
                885                 890                 895

Ile Asp Thr Leu Tyr Ala Asn Ser Gly Ala Gln Gly Arg Asp Leu Leu
            900                 905                 910

Gln Thr Leu Leu Ile Asp Ser His Asp Ala Gly Tyr Ala Arg Thr Met
        915                 920                 925

Ile Asp Ala Thr Ser Ala Asn Glu Ile Thr Lys Gln Leu Asn Thr Ala
    930                 935                 940

Thr Thr Thr Leu Asn Asn Ile Ala Ser Leu Glu His Lys Thr Ser Gly
945                 950                 955                 960

Leu Gln Thr Leu Ser Leu Ser Asn Ala Met Ile Leu Asn Ser Arg Leu
                965                 970                 975

Val Asn Leu Ser Arg Arg His Thr Asn His Ile Asp Ser Phe Ala Lys
            980                 985                 990

Arg Leu Gln Ala Leu Lys Asp Gln Arg Phe Ala Ser Leu Glu Ser Ala
        995                 1000                1005

Ala Glu Val Leu Tyr Gln Phe Ala Pro Lys Tyr Glu Lys Pro Thr
    1010                1015                1020

Asn Val Trp Ala Asn Ala Ile Gly Gly Thr Ser Leu Asn Ser Gly
    1025                1030                1035

Gly Asn Ala Ser Leu Tyr Gly Thr Ser Ala Gly Val Asp Ala Tyr
    1040                1045                1050

Leu Asn Gly Glu Val Glu Ala Ile Val Gly Gly Phe Gly Ser Tyr
    1055                1060                1065

Gly Tyr Ser Ser Phe Ser Asn Gln Ala Asn Ser Leu Asn Ser Gly
    1070                1075                1080

Ala Asn Asn Thr Asn Phe Gly Val Tyr Ser Arg Ile Phe Ala Asn
    1085                1090                1095

Gln His Glu Phe Asp Phe Glu Ala Gln Gly Ala Leu Gly Ser Asp
    1100                1105                1110

Gln Ser Ser Leu Asn Phe Lys Ser Ala Leu Leu Arg Asp Leu Asn
    1115                1120                1125

Gln Ser Tyr Asn Tyr Leu Ala Tyr Ser Ala Ala Thr Arg Ala Ser
    1130                1135                1140

Tyr Gly Tyr Asp Phe Ala Phe Arg Asn Ala Leu Val Leu Lys
    1145                1150                1155

Pro Ser Val Gly Val Ser Tyr Asn His Leu Gly Ser Thr Asn Phe
```

```
            1160                1165                1170

Lys  Ser  Asn  Ser  Asn  Gln  Lys  Val  Ala  Leu  Lys  Asn  Gly  Ala  Ser
        1175                1180                1185

Ser  Gln  His  Leu  Phe  Asn  Ala  Ser  Ala  Asn  Val  Glu  Ala  Arg  Tyr
        1190                1195                1200

Tyr  Tyr  Gly  Asp  Thr  Ser  Tyr  Phe  Tyr  Met  Asn  Ala  Gly  Val  Leu
        1205                1210                1215

Gln  Glu  Phe  Ala  Asn  Phe  Gly  Ser  Ser  Asn  Ala  Val  Ser  Leu  Asn
        1220                1225                1230

Thr  Phe  Lys  Val  Asn  Ala  Thr  Arg  Asn  Pro  Leu  Asn  Thr  His  Ala
        1235                1240                1245

Arg  Val  Met  Met  Gly  Gly  Glu  Leu  Lys  Leu  Ala  Lys  Glu  Val  Phe
        1250                1255                1260

Leu  Asn  Leu  Gly  Phe  Val  Tyr  Leu  His  Asn  Leu  Ile  Ser  Asn  Ile
        1265                1270                1275

Gly  His  Phe  Ala  Ser  Asn  Leu  Gly  Met  Arg  Tyr  Ser  Phe
        1280                1285                1290

<210> SEQ ID NO 11
<211> LENGTH: 1297
<212> TYPE: PRT
<213> ORGANISM: Helicobacter pylori NCTC 11638

<400> SEQUENCE: 11

Met  Glu  Ile  Gln  Gln  Thr  His  Arg  Lys  Ile  Asn  Arg  Pro  Leu  Val  Ser
1                    5                   10                  15

Leu  Ala  Leu  Val  Gly  Ala  Leu  Val  Ser  Ile  Thr  Pro  Gln  Gln  Ser  His
            20                  25                  30

Ala  Ala  Phe  Phe  Thr  Thr  Val  Ile  Ile  Pro  Ala  Ile  Val  Gly  Gly  Ile
        35                  40                  45

Ala  Thr  Gly  Thr  Ala  Val  Gly  Thr  Val  Ser  Gly  Leu  Leu  Ser  Trp  Gly
    50                  55                  60

Leu  Lys  Gln  Ala  Glu  Glu  Ala  Asn  Lys  Thr  Pro  Asp  Lys  Pro  Asp  Lys
65                  70                  75                  80

Val  Trp  Arg  Ile  Gln  Ala  Gly  Lys  Gly  Phe  Asn  Glu  Phe  Pro  Asn  Lys
                85                  90                  95

Glu  Tyr  Asp  Leu  Tyr  Arg  Ser  Leu  Leu  Ser  Ser  Lys  Ile  Asp  Gly  Gly
            100                 105                 110

Trp  Asp  Trp  Gly  Asn  Ala  Ala  Arg  His  Tyr  Trp  Val  Lys  Gly  Gly  Gln
        115                 120                 125

Gln  Asn  Lys  Leu  Glu  Val  Asp  Met  Lys  Asp  Ala  Val  Gly  Thr  Tyr  Thr
    130                 135                 140

Leu  Ser  Gly  Leu  Arg  Asn  Phe  Thr  Gly  Gly  Asp  Leu  Asp  Val  Asn  Met
145                 150                 155                 160

Gln  Lys  Ala  Thr  Leu  Arg  Leu  Gly  Gln  Phe  Asn  Gly  Asn  Ser  Phe  Thr
                165                 170                 175

Ser  Tyr  Lys  Asp  Ser  Ala  Asp  Arg  Thr  Thr  Arg  Val  Asp  Phe  Asn  Ala
            180                 185                 190

Lys  Asn  Ile  Ser  Ile  Asp  Asn  Phe  Val  Glu  Ile  Asn  Asn  Arg  Val  Gly
        195                 200                 205

Ser  Gly  Ala  Gly  Arg  Lys  Ala  Ser  Ser  Thr  Val  Leu  Thr  Leu  Gln  Ala
    210                 215                 220

Ser  Glu  Gly  Ile  Thr  Ser  Asp  Lys  Asn  Ala  Glu  Ile  Ser  Leu  Tyr  Asp
225                 230                 235                 240
```

```
Gly Ala Thr Leu Asn Leu Ala Ser Ser Val Lys Leu Met Gly Asn
            245                 250                 255
Val Trp Met Gly Arg Leu Gln Tyr Val Gly Ala Tyr Leu Ala Pro Ser
        260                 265                 270
Tyr Ser Thr Ile Asn Thr Ser Lys Val Thr Gly Glu Val Asn Phe Asn
    275                 280                 285
His Leu Thr Val Gly Asp Lys Asn Ala Ala Gln Ala Gly Ile Ile Ala
290                 295                 300
Asn Lys Lys Thr Asn Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asn Thr Pro Ser Gln Ser Gly Ala Lys Asn Asp Lys Asn Glu Ser Ala
            340                 345                 350
Lys Asn Asp Lys Gln Glu Ser Ser Gln Asn Asn Ser Asn Thr Gln Val
        355                 360                 365
Ile Asn Pro Pro Asn Ser Ala Gln Lys Thr Glu Val Gln Pro Thr Gln
    370                 375                 380
Val Ile Asp Gly Pro Phe Ala Gly Gly Lys Asp Thr Val Val Asn Ile
385                 390                 395                 400
Asn Arg Ile Asn Thr Asn Ala Asp Gly Thr Ile Arg Val Gly Gly Phe
                405                 410                 415
Lys Ala Ser Leu Thr Thr Asn Ala Ala His Leu His Ile Gly Lys Gly
            420                 425                 430
Gly Val Asn Leu Ser Asn Gln Ala Ser Gly Arg Ser Leu Ile Val Glu
        435                 440                 445
Asn Leu Thr Gly Asn Ile Thr Val Asp Gly Pro Leu Arg Val Asn Asn
    450                 455                 460
Gln Val Gly Gly Tyr Ala Leu Ala Gly Ser Ser Ala Asn Phe Glu Phe
465                 470                 475                 480
Lys Ala Gly Thr Asp Thr Lys Asn Gly Thr Ala Thr Phe Asn Asn Asp
                485                 490                 495
Ile Ser Leu Gly Arg Phe Val Asn Leu Lys Val Asp Ala His Thr Ala
            500                 505                 510
Asn Phe Lys Gly Ile Asp Thr Gly Asn Gly Gly Phe Asn Thr Leu Asp
        515                 520                 525
Phe Ser Gly Val Thr Asp Lys Val Asn Ile Asn Lys Leu Ile Thr Ala
    530                 535                 540
Ser Thr Asn Val Ala Val Lys Asn Phe Asn Ile Asn Glu Leu Ile Val
545                 550                 555                 560
Lys Thr Asn Gly Ile Ser Val Gly Glu Tyr Thr His Phe Ser Glu Asp
                565                 570                 575
Ile Gly Ser Gln Ser Arg Ile Asn Thr Val Arg Leu Glu Thr Gly Thr
            580                 585                 590
Arg Ser Leu Phe Ser Gly Gly Val Lys Phe Lys Gly Gly Glu Lys Leu
        595                 600                 605
Val Ile Asp Glu Phe Tyr Tyr Ser Pro Trp Asn Tyr Phe Asp Ala Arg
    610                 615                 620
Asn Ile Lys Asn Val Glu Ile Thr Asn Lys Leu Ala Phe Gly Pro Gln
625                 630                 635                 640
Gly Ser Pro Trp Gly Thr Ser Lys Leu Met Phe Asn Asn Leu Thr Leu
                645                 650                 655
Gly Gln Asn Ala Val Met Asp Tyr Ser Gln Phe Ser Asn Leu Thr Ile
```

-continued

```
              660                 665                 670
Gln Gly Asp Phe Ile Asn Asn Gln Gly Thr Ile Asn Tyr Leu Val Arg
            675                 680                 685
Gly Gly Lys Val Ala Thr Leu Ser Val Gly Asn Ala Ala Ala Met Met
690                 695                 700
Phe Asn Asn Asp Ile Asp Ser Ala Thr Gly Phe Tyr Lys Pro Leu Ile
705                 710                 715                 720
Lys Ile Asn Ser Ala Gln Asp Leu Ile Lys Asn Thr Glu His Val Leu
            725                 730                 735
Leu Lys Ala Lys Ile Ile Gly Tyr Gly Asn Val Ser Thr Gly Thr Asn
            740                 745                 750
Gly Ile Ser Asn Val Asn Leu Glu Glu Gln Phe Lys Glu Arg Leu Ala
            755                 760                 765
Leu Tyr Asn Asn Asn Asn Arg Met Asp Thr Cys Val Val Arg Asn Thr
            770                 775                 780
Asp Asp Ile Lys Ala Cys Gly Met Ala Ile Gly Asp Gln Ser Met Val
785                 790                 795                 800
Asn Asn Pro Asp Asn Tyr Lys Tyr Leu Ile Gly Lys Ala Trp Lys Asn
            805                 810                 815
Ile Gly Ile Ser Lys Thr Ala Asn Gly Ser Lys Ile Ser Val Tyr Tyr
            820                 825                 830
Leu Gly Asn Ser Thr Pro Thr Glu Asn Gly Gly Asn Thr Thr Asn Leu
            835                 840                 845
Pro Thr Asn Thr Thr Ser Asn Ala Arg Ser Ala Asn Asn Ala Leu Ala
            850                 855                 860
Gln Asn Ala Pro Phe Ala Gln Pro Ser Ala Thr Pro Asn Leu Val Ala
865                 870                 875                 880
Ile Asn Gln His Asp Phe Gly Thr Ile Glu Ser Val Phe Glu Leu Ala
            885                 890                 895
Asn Arg Ser Lys Asp Ile Asp Thr Leu Tyr Ala Asn Ser Gly Ala Gln
            900                 905                 910
Gly Arg Asp Leu Leu Gln Thr Leu Leu Ile Asp Ser His Asp Ala Gly
            915                 920                 925
Tyr Ala Arg Lys Met Ile Asp Ala Thr Ser Ala Asn Glu Ile Thr Lys
            930                 935                 940
Gln Leu Asn Thr Ala Thr Thr Thr Leu Asn Asn Ile Ala Ser Leu Glu
945                 950                 955                 960
His Lys Thr Ser Gly Leu Gln Thr Leu Ser Leu Ser Asn Ala Met Ile
            965                 970                 975
Leu Asn Ser Arg Leu Val Asn Leu Ser Arg Arg His Thr Asn His Ile
            980                 985                 990
Asp Ser Phe Ala Lys Arg Leu Gln Ala Leu Lys Asp Gln Lys Phe Ala
            995                 1000                1005
Ser Leu Glu Ser Ala Ala Glu Val Leu Tyr Gln Phe Ala Pro Lys
            1010                1015                1020
Tyr Glu Lys Pro Thr Asn Val Trp Ala Asn Ala Ile Gly Gly Thr
            1025                1030                1035
Ser Leu Asn Asn Gly Ser Asn Ala Ser Leu Tyr Gly Thr Ser Ala
            1040                1045                1050
Gly Val Asp Ala Tyr Leu Asn Gly Gln Val Glu Ala Ile Val Gly
            1055                1060                1065
Gly Phe Gly Ser Tyr Gly Tyr Ser Ser Phe Asn Asn Arg Ala Asn
            1070                1075                1080
```

```
Ser Leu Asn Ser Gly Ala Asn Asn Thr Asn Phe Gly Val Tyr Ser
    1085            1090            1095

Arg Ile Phe Ala Asn Gln His Glu Phe Asp Phe Glu Ala Gln Gly
    1100            1105            1110

Ala Leu Gly Ser Asp Gln Ser Ser Leu Asn Phe Lys Ser Ala Leu
    1115            1120            1125

Leu Gln Asp Leu Asn Gln Ser Tyr His Tyr Leu Ala Tyr Ser Ala
    1130            1135            1140

Ala Thr Arg Ala Ser Tyr Gly Tyr Asp Phe Ala Phe Phe Arg Asn
    1145            1150            1155

Ala Leu Val Leu Lys Pro Ser Val Gly Val Ser Tyr Asn His Leu
    1160            1165            1170

Gly Ser Thr Asn Phe Lys Ser Asn Ser Thr Asn Gln Val Ala Leu
    1175            1180            1185

Lys Asn Gly Ser Ser Ser Gln His Leu Phe Asn Ala Ser Ala Asn
    1190            1195            1200

Val Glu Ala Arg Tyr Tyr Tyr Gly Asp Thr Ser Tyr Phe Tyr Met
    1205            1210            1215

Asn Ala Gly Val Leu Gln Glu Phe Ala His Val Gly Ser Asn Asn
    1220            1225            1230

Ala Ala Ser Leu Asn Thr Phe Lys Val Asn Ala Ala Arg Asn Pro
    1235            1240            1245

Leu Asn Thr His Ala Arg Val Met Met Gly Gly Glu Leu Lys Leu
    1250            1255            1260

Ala Lys Glu Val Phe Leu Asn Leu Gly Val Val Tyr Leu His Asn
    1265            1270            1275

Leu Ile Ser Asn Ile Gly His Phe Ala Ser Asn Leu Gly Met Arg
    1280            1285            1290

Tyr Ser Phe Phe
    1295
```

TOLEROGENIC COMPOSITIONS COMPRISING AND USES THEREOF

CROSS-REFERENCE TO RELATED APPLICATION

This application is the U.S. national stage application of International Patent Application No. PCT/IB2015/050703, filed Jan. 30, 2015.

The Sequence Listing for this application is labeled "Seq-List.txt" which was created on Jul. 29, 2016 and is 116 KB. The entire content of the sequence listing is incorporated herein by reference in its entirety.

FIELD OF THE INVENTION

The present invention relates to prevention or treatment of allergic disorders, in particular asthma and food allergies, and in particular to compositions useful for the prevention of hypersensitivity to allergens, in particular asthma disorders, and/or the desensitization to allergens.

BACKGROUND OF THE INVENTION

The prevalence of allergic asthma and allergic diseases has reached epidemic proportions in both adult and pediatric, developed and developing populations (Eder et al., 2006, *N. Engl. J. Med.*, 355:2226-2235). The lack of early childhood infections or microbial exposure due to improved sanitation, and the gradual loss of the indigenous microbiota, have alternately been proposed to account for this major public health trend (Blaser, 2009, *Nat. Rev. Microbiol.*, 7:887-894). In 2011, 235-300 million people globally have been diagnosed with asthma, and it caused 250,000 deaths.

Asthma is now the most prevalent chronic disease in childhood in developed countries; approximately 300 million people suffer from this disease worldwide. Asthma is caused by a combination of genetic and environmental factors. The Global Initiative of Asthma defines asthma as a chronic inflammatory disorder of the airways. Chronic pulmonary inflammation is associated with airway hyper-responsiveness, which leads to the classical symptoms of asthma: recurrent episodes of wheezing, breathlessness, chest tightness and coughing. The most common clinical phenotype is allergic asthma. In childhood, more than 90% of patients with severe asthma are allergic; among asthmatic adults, 60% are sensitized to common aero-allergens (Holgate et al., 2003, *Eur. Respir. J.*, 22:470-477). In allergic asthma, inflammation and airway obstruction are triggered by allergen exposure in atopic individuals. The pathophysiology underlying the disease is rather complex. The inflammatory processes underlying the development of allergic airway disease have been investigated in humans and also in animal models of the disease. The understanding of the different cell types and mediators involved in asthma development has increased in the last decade. Indeed, findings support an important role of Th2 cells and Th2 cytokines (IL-4, IL-5 and IL-13) in the development of allergen-induced inflammation and airway hyper-responsiveness (AHR).

The state-of-the-art immunomodulatory treatment of acute symptoms of asthma involves inhaled or oral corticosteroids. Asthma patients generally respond to β2-adrenergic receptor agonists (such as salbutamol) and leukotrienes, which relax smooth muscle cells. In very severe cases, intravenous administration of corticosteroids or immunomodulatory drugs such as neutralizing antibodies to interleukins and hospitalization may be required. Anti-IL-13, anti-IL-5 and anti-IL-9 monoclonal antibodies are all currently in clinical trials for asthma.

*Helicobacter pylori* is a persistent bacterial pathogen colonizing the gastric mucosa of humans. It is typically acquired in early childhood and, in the absence of antibiotic therapy, may persist for the entire lifespan of the host. The extraordinary ability of *H. pylori* to resist a vigorous adaptive immune response driven in large part by Th1 and/or Th17-polarized effector T-cells has been attributed to its adaptation to and manipulation of the human innate and adaptive immune systems. *H. pylori* has colonized its human host for at least 60,000 years and during this long period of co-evolution has evolved elaborate ways to systemically manipulate adaptive immune responses and to promote its persistence through the preferential induction of regulatory T-cell (Treg) over immunogenic T-cell responses through T-effector cell responses. Treg-predominant responses are characteristic of heavily colonized but asymptomatic carriers.

It has been shown that experimental live *H. pylori* infection, especially when initiated during the neonatal period, protects effectively against allergen-induced asthma that is induced by allergen sensitization and challenge (Arnold et al., 2011, *The Journal of Clinical Investigation*, 121:3088-3093). Mechanistically, asthma protection is due to the development of (Treg-mediated) immune tolerance to *H. pylori*, which cross-protects against allergen-specific Th2 responses. The protective effects of live *H. pylori* are abrogated by antibiotic eradication therapy clearing the bacteria (Arnold et al., 2011, supra). Similarly, the induction of protective Tregs required live bacteria in vivo and could not be achieved by dead extract.

Aside from Tregs, dendritic cells (DCs) have emerged as a critical cell type required for immune tolerance. *H. pylori*-experienced DCs are reprogrammed toward a tolerance-promoting phenotype in vitro and in vivo (Oertli et al., 2013, *PNAS*, 110(8):3047-3052). It has been observed that DC reprogramming requires two *H. pylori*-secreted proteins (virulence determinants or factors), the vacuolating cytotoxin (VacA) and the γ-glutamyl-transpeptidase (GGT) (Oertli et al., 2013, supra), since *H. pylori* mutants that lack one of the two virulence factors (but are otherwise wild-type) fail to reprogram DCs in vivo and in vitro, and therefore cannot induce Tregs with suppressive activity in mice (Oertli et al., 2013, supra). As a consequence, both *H. pylori* mutant strains are cleared effectively by the mice (Oertli et al., 2013, supra). Furthermore, both GGT and VacA have been used or reported to be used to trigger vaccine-induced protective immunity to *H. pylori*, i.e., with the opposite goal (strong T effector rather than Treg responses) of the present aim of the invention (Malfertheiner et al., 2008, *Gastroenterology*, 135(3):787-95).

The use of live *H. pylori* as a therapeutic intervention or preventive measure has been unattractive due to the well-documented carcinogenic potential of chronic infection with this organism, since *H. pylori* induces gastric and duodenal ulcers (Marshall et al., 1984, *Lancet*, 1:1311-1315), and is also widely accepted to be the leading cause of gastric adenocarcinoma (Parsonnet et al., 1991, *N. Engl. J. Med.*, 325:1127-1131). Further, it is important to note that those vaccination strategies using *H. pylori* are aimed at inducing an immune response that would protect the subject from *H. pylori* infection and counter-acting the ability of *H. pylori* to avoid or bypass the immune system response.

Since all the current treatments of asthma induce more or less severe side effects, alternative treatment strategies are desperately needed. Therefore, there are important needs for new strategies of prevention of asthma development, particularly for children and young people that present a predisposition towards developing hypersensitivity reactions and for treatment of asthma causes and symptoms.

SUMMARY OF THE INVENTION

The present invention relates to the unexpected finding that oral, intranasal or intraperitoneal (i.e., systemic) administration of a composition comprising *H. pylori* VacA (administered either in the form of a dead cell extract such as prepared by mechanic disruption of logarithmically growing *H. pylori* using a French pressure cell "French press" or in the form of purified or recombinant protein), when administered at regular intervals, is able to induce protection against allergen-induced asthma. Although the presence of this virulence determinant or factor was earlier found to be required for persistence and Treg induction, it was in combination with the virulence determinant GGT and in the context of live bacteria and it could not be anticipated that it would have been sufficient alone for asthma protection. Further, the fact that VacA has successfully been included in preclinical and phase 1 human trials of *H. pylori*-specific vaccination argues that it is immunogenic (at least in combination with a suitable adjuvant) and triggers either T-cell and/or antibody-mediated immunity. Since strong immunogenicity and strong immunomodulatory properties, as required for the suppression of allergen-specific immune responses, are usually mutually exclusive and not typically found in the same protein, the tolerogenic properties of compositions according to the invention are particularly surprising. The present invention further relates to the unexpected finding that it is possible to induce a peripheral tolerance avoiding an immune response to *H. pylori* infection through the use of VacA and thereby achieving a rather non-specific form of tolerogenic immunomodulation.

A first aspect of the invention provides a polypeptide selected from a VacA protein, a fragment or variant thereof or a formulation thereof for use in the prevention and/or treatment of an allergic disorder, in particular allergen-induced or atopic asthma.

A second aspect of the invention relates to a polypeptide selected from a VacA protein or a fragment or variant thereof for inducing a tolerization response to an allergen.

A third aspect of the invention relates a use of a polypeptide selected from a VacA protein or a fragment or variant thereof for the preparation of a medicament for prevention and/or treatment of an allergic disorder, in particular atopic asthma, and/or inducing a tolerization response to an allergen.

A fourth aspect according to the invention relates to a pharmaceutical formulation comprising a VacA protein or a fragment or variant thereof and at least one pharmaceutically acceptable carrier, diluent or excipient thereof.

A fifth aspect of the invention relates to a method of inducing a tolerization response to an allergen in a subject, said method comprising administering to a subject in need thereof an effective amount a polypeptide selected from a VacA protein, a fragment or variant thereof, or a pharmaceutical formulation thereof.

A sixth aspect of the invention relates to a method of preventing, repressing or treating an allergic response, in particular an allergic disorder in a subject, said method comprising administering to a subject in need thereof a therapeutically effective amount a polypeptide selected from a VacA, a fragment or variant thereof, or a pharmaceutical formulation thereof.

A seventh aspect of the invention relates to a pharmaceutical formulation comprising a polypeptide selected from a VacA protein or a fragment or variant thereof, combined with at least one co-agent useful in the prevention and/or treatment of an allergic disorder, in particular atopic asthma, and/or for inducing a tolerization response to an allergen, and at least one pharmaceutically acceptable carrier, diluent or excipient thereof.

An eighth aspect of the invention relates to a VacA protein, a fragment or variant thereof or a pharmaceutical formulation thereof for the prevention and/or treatment of an allergic disorder, in particular asthma, and/or for inducing a tolerization response to an allergen.

These data support that, unexpectedly, the administration of VacA alone in purified form is able to induce asthma protection comparable to the whole cell extract and therefore may be administered in purified form to prevent allergic asthma.

FIG. 5 shows examples of amino acid sequences of the VacA polypeptides described herein. A: s1m1 VacA (Q48245 *H. pylori* strain ATCC 49503/60190) of SEQ ID NO: 1; B: s2m2 VacA of SEQ ID NO: 2; C: negative control mutant (46-27) VacA of SEQ ID NO: 3; D-K: SEQ ID NO: 4 to SEQ ID NO: 11.

Figure 6:
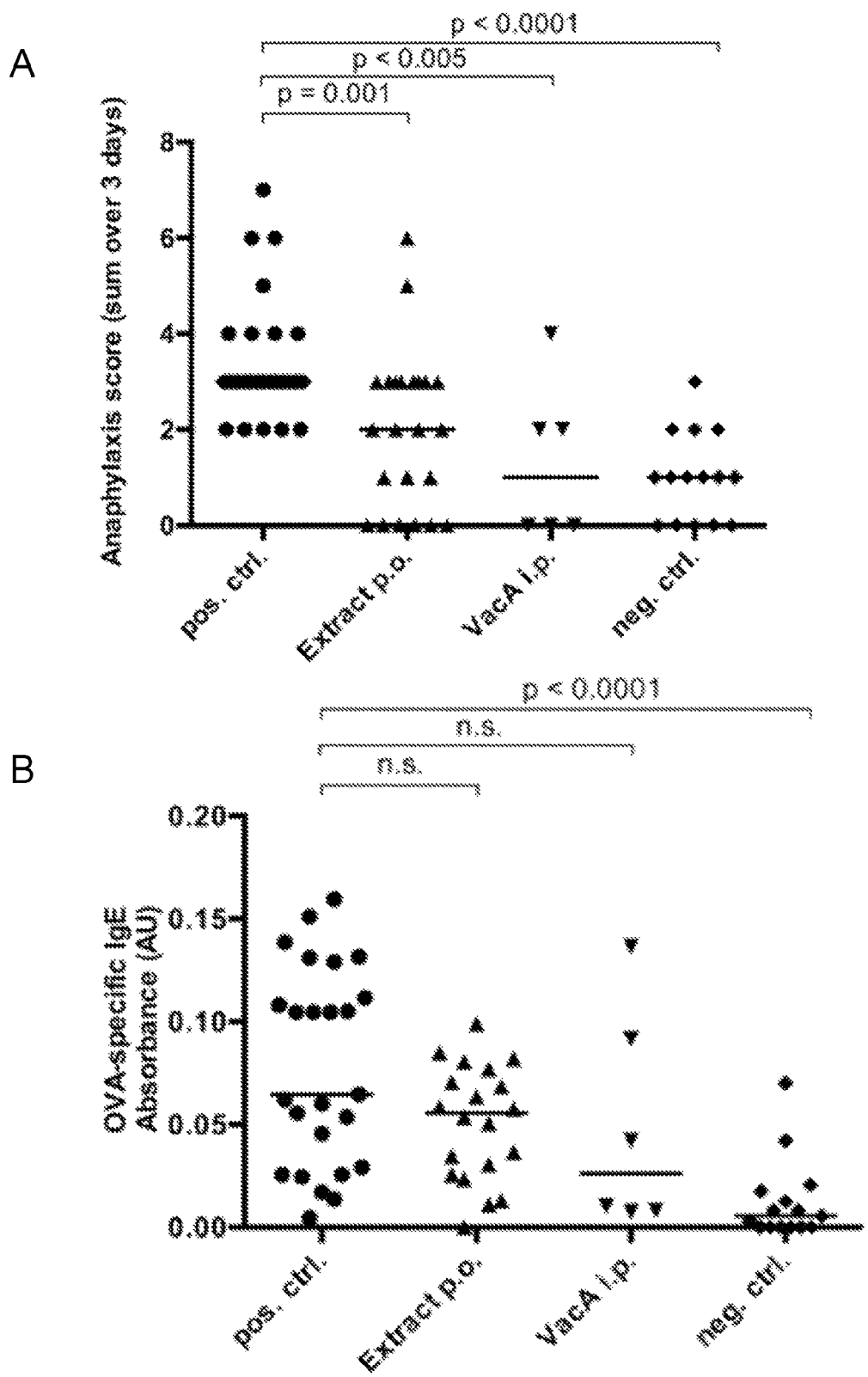
Figure 6:
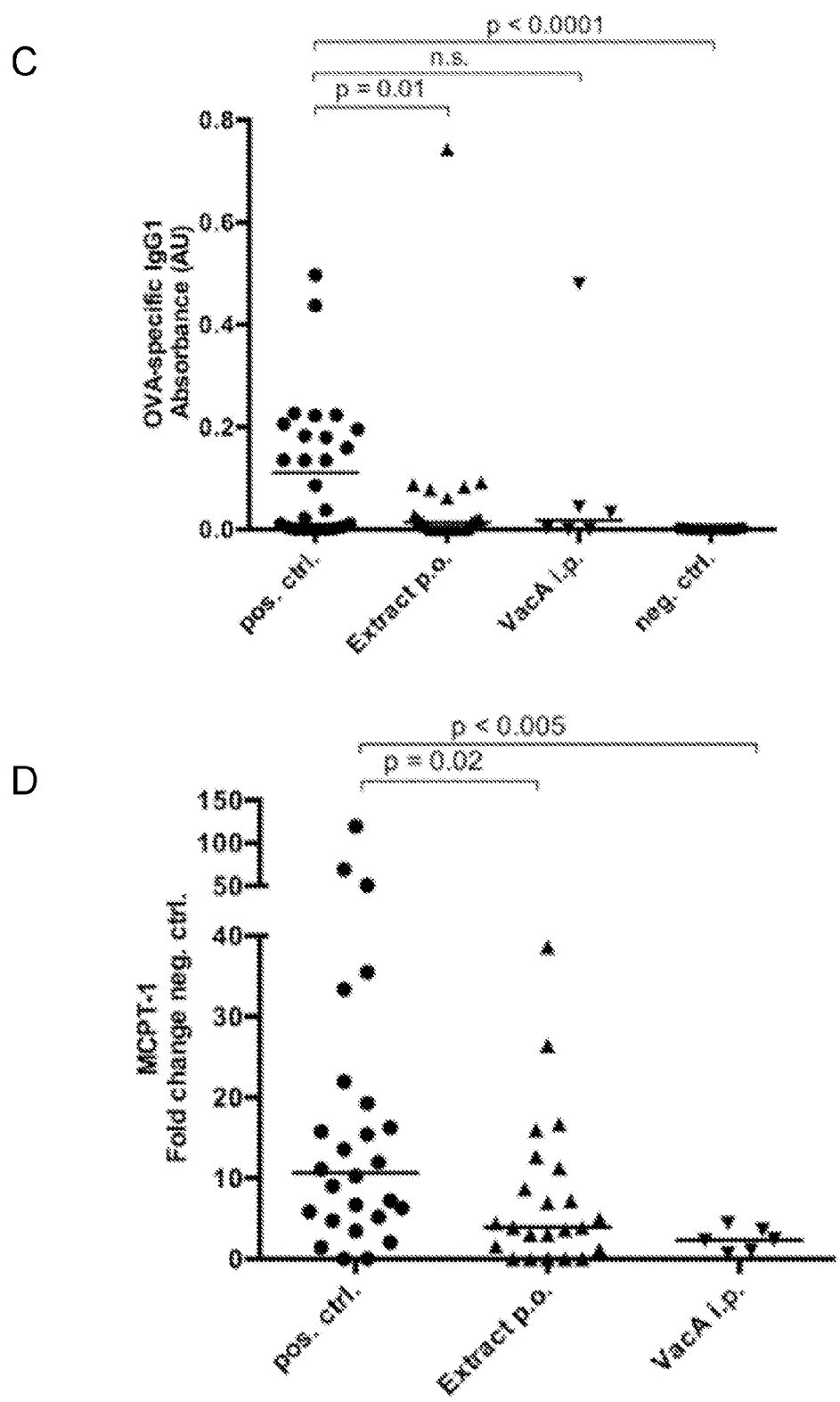
Figure 6:
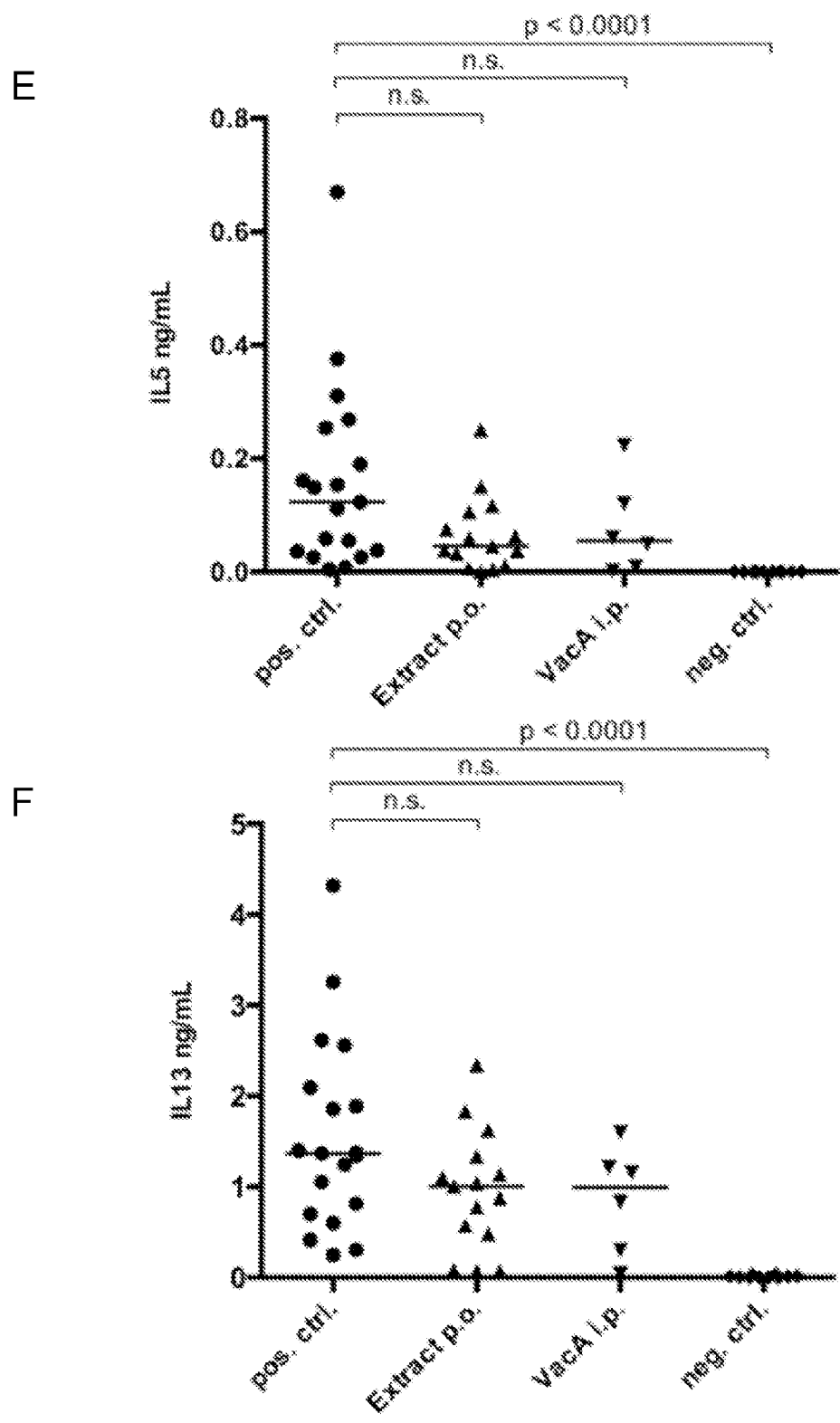

FIG. 6 shows beneficial effects of *H. pylori* extract and HpVacA based on clinical scoring (A) and on systemic parameters of food allergy (C to F) as described in Example 5. These data support that, unexpectedly, the administration of VacA alone in purified form is able to induce food allergy protection comparable to the whole cell extract and therefore may be administered in purified form to prevent allergic asthma.

DETAILED DESCRIPTION

The term "allergic disorder" refers to allergic settings and hypersensitivity to allergens such as allergen-induced or atopic asthma, atopic dermatitis (eczema), atopic rhinitis (hay fever), allergic conjunctivitis, food allergy, occupational allergy, allergic broncho-pulmonal aspergillosis and hypersensitivity pneumonitis.

The term "asthma" refers to a disorder of the airways characterized by airway inflammation, hyper-responsiveness, and obstruction which often causes spasms of the bronchial smooth muscle system, and affects both the upper and lower respiratory tracts. There are several forms of asthma, characterized by varying degrees of severity. Mild asthma, for example, is defined as brief episodes of wheezing, with or without dyspnea or cough. Moderately severe asthma is defined as wheezing and dyspnea, and can be with or without cough and expectoration, but generally interferes with daily activities and/or sleeping. Severe asthma is characterized by incapacitation due to dyspnea, and the afflicted patient typically is unable to eat or sleep normally, is very anxious, and is often exhausted. A condition known as status asthmaticus is the most severe form of asthma, and generally requires intensive hospital care, and may even prove fatal. The disease may occur as a result of both allergic and non-allergic mechanisms.

The term "allergen-induced asthma" or "atopic asthma" refers to asthma resulting from a hypersensivity to an antigen/allergen. This includes, but is not limited to, all inhalable allergens including pollen form trees, grass, weeds or herbs or other groups of allergens such as house dust mites, animal dander, cockroaches, fungi and molds. Furthermore, occupational allergens, such as flour, soy, cow, latex and different mites (*Tyrophagus putrescentiae, Lepidoglyphus destructor, Acarus siro*) are included. Hypersensitivity to allergens, in particular antigen/allergen-induced asthma, is usually diagnosed on the basis of the pattern of symptoms such as coughing, sneezing, irritation/itching of the nose or eyes, increased lacrimation and running nose, and itching of the skin with formation of eczema, as well as nausea, vomiting, abdominal pain and discomfort and diarrhea in food allergy. Atopic asthma is clinically classified according to the frequency of symptoms, decreased forced expiratory volume in one second (FEV1) or peak expiratory flow rate (Peak Flow), increased Peak Flow variability, airway hyper-responsiveness and increased levels of allergen-specific IgE.

The term "food allergy" refers to an abnormal response of the human immune system to harmless foods, caused by the immune system's reaction to some food proteins, usually involving human antibodies produced against specific allergens found in the food. Examples of common food allergens include components of milk, soy, fish and shellfish, tree nuts, peanuts, wheat (gluten), and eggs.

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising tolerogenic fragments.

The term "fragments" refers to polypeptides comprising a portion of peptide sequence corresponding to contiguous amino acids of a polypeptide set forth herein, including all intermediate lengths and variants thereof.

The term "VacA" includes s1m1 VacA (SEQ ID NOs: 1, 4-11) and s2m2 VacA (SEQ ID NO: 2), such as described in Cover et al., 1992, *J. Biol. Chem.*, 267:10570-1057 and Cover et al., 1997, *J. Cell. Biol.*, 138:759-769. According to a particular embodiment, VacA is s1m1 VacA of SEQ ID NO: 1. According to another embodiment, VacA is s2m2 VacA of SEQ ID NO: 2. According to another embodiment, VacA is s1m1 VacA of SEQ ID NO: 9.

The term "variant" applies to both a polynucleotide or a polypeptide. A polypeptide "variant," as the term is used herein, is a peptide or a polypeptide substantially homologous to the referenced peptide sequence, but which has an amino acid sequence different from that of the referenced. Such variants may be naturally occurring or may be synthetically generated, for example, by modifying one or more of the above polypeptide sequences of the invention described herein using any of a number of techniques well-known in the art. In many instances, a variant will contain conservative substitutions. Substantially homologous means a variant amino acid sequence which is identical to the referenced peptide sequence except for the deletion, insertion and/or substitution of a few amino acids, e.g., 1, 2, 3, 4, 5, or 6 amino acids. Substantially homologous means a variant amino acid sequence that is at least 80%, at least 85%, at least 90%, at least 95%, at least 96%, at least 97%, at least 98% or at least 99% identical to the referenced amino acid sequence. A variant nucleic acid sequence can be at least 80%, at least 85%, at least 90%, at least 95%, at least 96%, at least 97%, at least 98% or at least 99% identical to the referenced nucleic acid sequence. The identity of two amino acid sequences or of two nucleic acid sequences can be determined by visual inspection and/or mathematical calculation, or more easily by comparing sequence information using known computer programs used for sequence comparison such as the Clustal package, version 1.83.

A variant may comprise a sequence having at least one conservatively substituted amino acid. A "conservative substitution" is one in which an amino acid is substituted for another amino acid that has similar properties, such that one skilled in the art of peptide chemistry would expect the secondary structure and hydropathic nature of the polypeptide to be substantially unchanged (e.g., having similar physiochemical characteristics). Modifications may be made in the structure of the polynucleotides and polypeptides of the present invention and still obtain a functional molecule that encodes a variant or derivative polypeptide with desirable characteristics, e.g., with tolerogenic characteristics. When it is desired to alter the amino acid sequence of a polypeptide to create an equivalent, or even an improved, tolerogenic variant or portion of a polypeptide of the invention, one skilled in the art will typically change one or more of the codons of the encoding DNA sequence. In making such changes, the hydropathic index, polarity, charge, solubility, hydrophobicity, hydrophilicity and/or amphipathic nature of the amino acids are considered. The importance of the hydropathic amino acid index in conferring interactive biological functions on a protein is generally understood in the art (Kyte et al., 1982, *J. Mol. Biol.*, 157: 105-131). Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well-known (Kyte et al., 1982, supra). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below. The term "variant" also includes a peptide or polypeptide substantially homologous to the referenced peptide sequence, but which has an amino acid sequence different from that of the referenced sequence because one or more amino acids have been chemically modified or substituted by amino acid analogs. This term also includes glycosylated polypeptides.

TABLE 1

| Original residues | Examples of substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile, Met, Leu, Phe, Ala |

Generally, substitutions for one or more amino acids present in the original polypeptide should be made conservatively. Polypeptides of the invention, polypeptide fragments and variants thereof are capable of inducing tolerance to an antigen/allergen when administered in vivo.

By "tolerogenic fragment" is meant a fragment that can induce tolerance to antigens/allergens described in the present application. In certain embodiments, a tolerogenic fragment can induce tolerance to antigens/allergens at least as well as the full-length VacA polypeptide can and in certain embodiments may be more effective than the full-length VacA polypeptide at inducing tolerance. However, in certain embodiments, a tolerogenic fragment induces tolerance to antigens/allergens but may not induce tolerance as effectively as the full-length VacA polypeptide. Such tolerogenic fragments may still be useful in the present invention, particularly where said tolerogenic fragments have other advantageous properties, such as, but not limited to, ease of preparation or purification as compared to the full-length VacA polypeptide. As would be recognized by the skilled person, a variety of known assays can be used to assess induction of tolerance, including measuring delayed-type hypersensitivity (DTH) responses, measuring cytokine productions by ELISA or other methods, T cell proliferation or cytotoxicity assays, B cell proliferation assays, antibody production, and the like. Such assays are known in the art and are described, for example, in *Current Protocols in Immunology*, Coligan et al. (ed.), 2001, John Wiley & Sons, N.Y., N.Y.; Ausubel et al., *Current Protocols in Molecular Biology*, 2001, Greene Publ. Assoc. Inc. & John Wiley & Sons, N.Y., N.Y.).

Polypeptides of the invention are prepared using any of a variety of well-known synthetic and/or recombinant techniques, the latter of which are further described below. Polypeptides, portions and other variants generally less than about 150 amino acids can be generated by synthetic means, using techniques well-known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain (Merrifield, 1963, *J. Am. Chem. Soc.*, 85:2149-2146).

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and is not necessarily meant to imply cure or complete abolition of symptoms, but refers to any type of treatment that imparts a benefit to a patient and includes: (a) preventing the disease from occurring in a subject which may be predisposed to the disease but has not yet been diagnosed as having it, for example based on familial history, overweight status or age; (b) inhibiting the disease, i.e., arresting its development; or (c) relieving the disease, i.e., causing regression of the disease and/or its symptoms or conditions, such as improvement or remediation of damage.

In particular, prevention and/or treatment of allergic disorders according to the invention comprises normalization or decrease of the antigen/allergen sensitivity of an individual. The term "treatment" refers to any type of treatment or prevention that imparts a benefit to a subject afflicted with or at risk of developing a hypersensitive immune response to an allergen/allergen of interest, including improvement in the condition of the subject (e.g., in one or more symptoms), delay in the onset of symptoms or slowing the progression of symptoms, etc. According to a particular aspect, prevention and/or treatment of allergic disorders according to the invention comprises inducing peripheral tolerance to allergens.

According to one aspect, effects of a treatment according to the invention may be observed through one or more the following: prevention or reduction of airway hyper-responsiveness, prevention or reduction of cell penetration into bronchial tubes (typically through the functional mechanisms for inhibiting production of IL-4, which is a cytokine secreted by Th2 cells and involved in inflammatory mechanisms of allergic reaction), and prevention or reduction of pulmonary inflammation, bronchoalveolar eosinophilia, goblet cell metaplasia, mucus production and Th2 cytokine production, which are hallmarks of allergen-induced asthma. Treatment success may also be evident by the observation of the generation of IL-10 in regulatory lymphocytes or other cells or in total lungs (BALF, sputum) or serum, which can be assessed by ELISA.

The term "subject" as used herein refers to mammals. For example, mammals contemplated by the present invention include humans, primates, and domesticated animals such as cattle, sheep, pigs, horses, laboratory rodents and the like.

The term "high-risk" subjects or individuals are subjects that are at risk of developing hypersensitivity to allergens/antigens, in particular of developing atopic or allergen-induced asthma. Those include genetic predisposition such as a family history of atopic diseases in close relatives, smoking mother during pregnancy, smoking to environment after birth, viral respiratory infections such as by respiratory syncytial virus and rhinovirus, and occupational exposure to known occupational allergens (e.g., flour). The risk or predisposition of developing hypersensitivity to allergens/antigens, in particular of developing atopic or allergen-induced asthma, can be assessed by recording the complete history including family history of the patient, skin prick testing, assessment of serum IgE, specific serum IgE levels and measurement of airway hyperreactivity.

The term "efficacy" of a treatment or method according to the invention can be measured based on changes in the course of a disease or condition in response to a use or a method according to the invention. For example, the efficacy of a treatment or method according to the invention can be measured by measuring the level of tolerance of the subject before and after the treatment, for example as described below.

The term "tolerance" as referred herein is defined as immune unresponsiveness to an antigen/allergen, usually an antigen/allergen implicated in causing disease. Although tolerance may be induced by administering antigens/allergens by different routes, oral tolerance refers to the oral administration of the composition, which results in inducing tolerance to an antigen/allergen when administered in vivo. The induction of tolerance can therefore be monitored by various techniques, including measuring the response to the allergen in a skin prick test, assessment of allergen-specific IgE and assessment of specific T cell responses for the allergen (proliferation and cytokine production).

The term "tolerogenic effective amount" as used herein refers to an amount of at least one polypeptide selected from VacA, a VacA fragment or VacA variant or a pharmaceutical formulation thereof according to the invention that elicits a detectable tolerogenic response in a subject that is being administered to said subject.

As used herein, the term "antigen" refers to a foreign substance that when introduced into the body triggers an immune system response, resulting in production of an antibody as part of the body's defense against disease.

The term "allergen" is meant to designate an antigen capable of eliciting a hypersensitive immune response (such as described herein) in an individual, such as an animal, such as a human. The allergen may be a sensitizing allergen or a cross-reacting allergen.

The term "non-denatured" refers to the absence of observed denaturation of the protein (e.g., structure). This can be verified by any method well-known in the art such as gel electrophoresis, gel filtration or mass spectrometry.

The polypeptides of the invention and formulations thereof have immunomodulatory properties that can be useful for tolerization strategies such as in allergic disorders and in particular allergic asthma. The polypeptides of the invention and formulations thereof can be useful in particular in tolerization treatments for asthma prevention in high-risk individuals.

VacA Polypeptides of the Invention in the Form of Dead Cell Extracts or Purified Peptides VacA polypeptides of the invention, fragments and variants thereof include substances described in the detailed description and they can be administered in different forms including in the form of a cell extract (dead) containing VacA or in the form of a purified synthetic polypeptide (recombinantly produced or obtained by synthesis).

In one aspect, the present invention provides VacA polypeptides of the invention, including fragments and variants thereof, in the form of an *H. pylori* bacterial dead cell extract.

In a further aspect, the present invention provides VacA polypeptides of the invention, including fragments and variants thereof, in the form of an *H. pylori* bacterial cell extract, wherein bacterial cells are non-denatured killed *H. pylori* bacterial cells.

In a further aspect, the present invention provides VacA polypeptides of the invention, including fragments and variants thereof, in the form of an *H. pylori* bacterial dead cell extract, wherein the *H. pylori* bacteria strain is *H. pylori* PMSS1 (Arnold et al., 2011, *Gastroenterology*, 140:199-209), or any other useful human patient isolate of *H. pylori*, or mutants of said isolates that lack one or more genes due to gene deletion or insertion mutagenesis or point mutations.

The processes which may be used for preparing *H. pylori* cell extracts are known to the skilled person and include the use of physical means that produce non-denatured killed cell bacteria, i.e., under non-denaturating conditions such as described in Laemmli et al., 1970, *Nature*, 277, 680-685, such as the use of the so called "French pressure cell press" (Kelemen et al., 1979, *J. Cell Sci.*, 35:431-441). Alternatively, ultrasonication or other methods such as extended freeze-drying, repeated cycles of freezing and thawing, lyophilization, homogenization techniques and other cell disruption techniques using physical forces can be applied, as long as they preserve *H. pylori* proteins in native form such as described in Bhaduri et al., 1983, *Appl. Environ. Microbiol.*, 46(4):941-3.

In another further aspect, the present invention provides VacA polypeptides of the invention and fragments and variants thereof in the form of an *H. pylori* bacterial cell extract obtainable by a process comprising the steps of:
 (i) harvesting a culture of living bacterial cells;
 (ii) submitting the harvested bacteria to several freeze/thaw cycles in water or an aqueous solution of a salt;
 (iii) disrupting the bacterial cells under high pressure, e.g., using a French pressure cell press; and
 (iv) collecting the cell extract.

In another further aspect, the present invention provides VacA polypeptides of the invention and fragments and variants thereof, in the form of an *H. pylori* bacterial cell extract obtainable by a process as described above, comprising a further step of removing the cell debris after or when collecting the cell extract.

In another aspect, the present invention provides VacA polypeptides of the invention, including fragments and variants thereof, in the form of a purified VacA polypeptide.

In another further aspect, the present invention provides VacA polypeptides of the invention, including fragments and variants thereof, in the form of a purified recombinant VacA polypeptide.

In another further aspect, the present invention provides VacA polypeptides of the invention, including fragments and variants thereof, in the form of VacA polypeptide composition essentially pure, i.e., essentially free from other native extract antigen components such as CagA and or NAP (neutrophil-activating protein). For example, such essentially pure VacA polypeptide compositions can be obtained from mutated *H. pylori* strains that have the other component(s)'s genes knocked out, such as where the CagA gene is knocked out.

The preparation of VacA polypeptide, fragments and variants thereof according to the invention recombinantly, can be achieved by various techniques known in the art. Nucleic acid sequence encoding for said VacA polypeptide, fragments and variants thereof can be inserted in the recombinant expression vector by methods well-known to a person skilled in the art, such as those described in *Molecular Cloning: A Laboratory Manual*, Sambrook et al., 4th Ed., Cold Spring Harbor Laboratory Press, Cold Spring Harbor, N.Y., 2001.

In a further embodiment, it is provided a host cell comprising a recombinant vector according to the invention.

The introduction of the recombinant vector into a host cell can be carried out according to methods that are well-known to a person skilled in the art, such as those described in *Basic Methods in Molecular Biology*, Davis et al., 2nd ed., McGraw-Hill Professional Publishing, 1995, and *Molecular Cloning: A Laboratory Manual*, supra, such as transfection by calcium phosphate, transfection by DEAE dextran, transfection, microinjection, transfection by cationic lipids, electroporation, transduction or infection.

The host cells can be, for example, bacterial cells such as *E. coli*, cells of fungi such as yeast cells, cells of *Aspergillus* and *Streptomyces*, insect cells, Chinese Hamster Ovary (CHO) cells, the C127 mouse cell line, the BHK cell line of Syrian hamster cells, or Human Embryonic Kidney 293 (HEK 293) cells. In a particular embodiment, the host cell is a CHO cell or an HEK 293 cell.

The host cells can be used, for example, to express a polypeptide of the invention. After purification by standard methods, the polypeptide of the invention can be used in a method described hereinafter.

For instance, when expression systems that secrete the recombinant protein are employed, the culture medium may first be concentrated using a commercially available protein concentration filter, for example, an ultrafiltration unit. Following the concentration step, the concentrate can be applied to a purification matrix such as a gel filtration medium. Alternatively, an anion exchange and/or an affinity resin can be employed. The matrices can be acrylamide, agarose, dextran, cellulose or other types commonly employed in protein purification. Alternatively, a cation exchange step can be employed. Some or all of the foregoing purification steps, in various combinations, are well-known and can be employed to provide a substantially homogeneous recombinant protein.

Recombinant polypeptides produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of other physical or chemical cell lysing agents, including detergents.

In another aspect, VacA polypeptide of the invention can be prepared recombinantly as a full-length protein as described in McClain et al., 2003, *J. Biol. Chem.*, 278: 12101-12108, or through the reconstitution of its two domains, p33 and p55, in the presence of detergents as described in Gonzalez-Rivera et al., 2010, *Biochemistry*, 49:5743-5752 and Gangwer et al., 2007, *PNAS*, 104(41): 16293-8.

In another aspect, the present invention provides variants or fragments of the VacA polypeptides described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along their length, to polypeptide sequences set forth herein.

In another aspect, the VacA polypeptides, fragments and variants thereof can be used associated with a pharmaceutically acceptable salt or a combination of pharmaceutically acceptable salts.

Compositions

The invention provides VacA polypeptides, variants or fragments thereof, pharmaceutical compositions thereof, and methods for treating a subject, in particular a mammalian subject, and most particularly a human patient who is suffering from a hypersensitivity to an antigen/allergen or a risk of developing hypersensitivity to an antigen/allergen, in particular allergen-induced or atopic asthma or food allergy.

According to another aspect, the invention provides VacA polypeptides, variants or fragments thereof, pharmaceutical compositions thereof and methods for controlling hypersensitivity to an antigen/allergen in a subject, in particular inducing a tolerance to said antigen/allergen.

In a particular embodiment, the invention provides VacA polypeptides or variants or fragments thereof and a pharmaceutical formulation according to the invention for use as a medicament.

Pharmaceutical compositions of the invention can contain at least one VacA polypeptide or variant or fragment thereof according to the invention in any form described herein. According to a particular aspect, the pharmaceutical compositions of the invention are tolerogenic compositions. In a particular aspect, pharmaceutical compositions of the invention are tolerogenic compositions capable of inducing a peripheral tolerance and diminishing the immune response to antigens through immunoregulation. In a particular embodiment, pharmaceutical compositions of the invention comprise at least one VacA polypeptide or variant or fragment thereof which is essentially free from immunogenic components such as immunogenic epitopes or allergens.

In another particular aspect, pharmaceutical compositions of the invention are tolerogenic compositions comprising at least one VacA polypeptide or variant or fragment thereof in combination with known allergens, such as food allergens, such as allergens deriving from milk, peanut, fish or shellfish, wheat (gluten), soy, egg or the like.

In another particular aspect, pharmaceutical compositions of the invention are tolerogenic compositions comprising at least one VacA polypeptide or variant or fragment thereof in combination with known allergens, such as allergens derived from pollens, such as pollens from grasses, trees, and weeds or the like. According to a particular aspect, such tolerogenic compositions have the ability of inducing allergen-specific immune tolerance and diminishing the immune response through immunoregulation (known as desensitization, hyposensitization or immunotherapy).

According to a particular aspect, at least one VacA polypeptide or variant or fragment thereof of the invention is administered in combination with known allergens, in particular food allergens. The combination might be achieved by concomitant administration of said at least one VacA polypeptide or variant or fragment thereof and the allergen, or administration of said at least one VacA polypeptide or variant or fragment thereof and the allergen within the same single formulation, or administration of said at least one VacA polypeptide or variant or fragment thereof when covalently linked to some immunogenic component of said allergen.

Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based on injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to a particular embodiment, compositions according to the invention are injectable.

Compositions of this invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methylcellulose, glucose/sugar syrup, gelatin, hydroxyethylcellulose, carboxymethylcellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include, but are not limited to, poly(ethylene glycol), glycerol, bovine serum albumin, Tween® and Span®.

Further materials as well as formulation processing techniques and the like are set out in Part 5 of *Remington: The Science and Practice of Pharmacy*, 22$^{nd}$ Edition, 2012, University of the Sciences in Philadelphia, Lippincott Williams & Wilkins, the content of which is incorporated herein by reference.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well-known in the art.

Compositions of this invention may also be formulated for inhalation, which may be in a form including, but not limited to, a solution, suspension, or emulsion that may be administered as a dry powder or in the form of an aerosol or spray using a propellant.

The compounds of this invention can also be administered in sustained release forms or from sustained release drug delivery systems.

In certain embodiments, the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, and stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and improve solubility.

The pharmaceutical composition of the invention may consist of dosage units that can be administered as an aerosol. The term "aerosol" is used to denote a variety of systems ranging from those of a colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation, may determine preferred aerosols.

According to one aspect, the invention provides an oral pharmaceutical composition.

According to one aspect, the invention provides an injectable pharmaceutical composition.

According to one aspect, the invention provides an inhalable pharmaceutical composition.

As described elsewhere herein, in certain embodiments, a prophylactic/therapeutically effective dose of a VacA polypeptide, a variant or fragment thereof, or a pharmaceutical composition thereof as used herein is a dose sufficient to induce tolerance to an antigen/allergen measured using any of a variety of methods as described herein. In a further embodiment, a prophylactic/therapeutically effective dose of a VacA polypeptide, a variant or fragment thereof, or a pharmaceutical composition thereof as used herein is a dose sufficient to induce T cell tolerance to an antigen/allergen as measured using any of a variety of methods as described herein, such as cytokine release assays, intracellular cytokine staining and flow cytometry, and the like. Functional T-cell assays or T-cell suppression assays measuring the suppression of proliferation or cytokine secretion by co-cultured effector T-cells may also be used.

Mode of Administration

Polypeptides and compositions of this invention may be administered in any manner including intravenous injection, intraperitoneal injection, subcutaneous injection, oral route, intranasal administration, intrapulmonary instillation or inhalation. In certain embodiments, a combination of different routes may also be used.

The exact dose of polypeptides and compositions is readily determined by one of skill in the art based on the teachings herein, along with the potency of the specific polypeptide and composition, and the age, weight, sex and physiological condition of the subject.

By way of example, in various embodiments the dosage of a tolerizing polypeptide and composition required to achieve (or maintain) tolerance in a subject is low relative to traditional tolerization regimens. For instance, as few as one or a few doses (e.g., fewer than about three, or fewer than about five doses) of agent may be sufficient to induce tolerance. By way of example, a weekly dose from about 5 to about 500 mg/dose might be used to achieve tolerization effects.

According to one embodiment, polypeptides and compositions of the invention are administered before or at the beginning of the onset of the allergic symptoms or the exposure to the allergen challenge. For example, polypeptides and compositions of the invention are administered before the subject is subjected to the allergen(s), typically in the case of patients at risk of suffering from a seasonal allergic disorder such as pollen allergy, or before the patient has already developed allergic symptoms, in the case of infants at risk of suffering from an allergic disorder (e.g., genetic or environmental risk) such as atopic asthma. Administration during pregnancy (oral, intranasal or via any other route) to pregnant mothers at risk of atopy can be envisioned as well, either alone or in combination with continued treatment of the newborn infant such as described in Pfefferle et al., 2013, *J. Allergy Clin. Immunol.,* 131(6): 1453-63.

According to a further embodiment, the polypeptides and compositions of the invention are administered at least two weeks (e.g., from about two to about 12 weeks) before the usual period of allergen exposure. According to a further embodiment, the polypeptides and compositions of the invention are administered by repeated administrations before and/or until and/or throughout the allergen exposure, such as from about once or twice a week to about once or twice a month. In the case of administration to pregnant mothers with the goal to reduce asthma and allergic risk in the newborn, the administration should be initiated early, ideally already in the first trimester (Pfefferle et al., 2013, supra).

Combination

According to the invention, a VacA polypeptide, a variant or fragment thereof and pharmaceutical formulations thereof can be administered alone or in combination with a co-agent useful in the prevention and/or treatment of hypersensitivity, in particular allergic disorders such as atopic asthma, e.g., a co-agent selected from a bronchodilator, a co-administered allergen used for hyposensitization with a co-agent useful in the tolerization to an antigen/allergen, e.g., antibodies or other reagents that interfere with co-stimulation or co-inhibition (e.g., via PD1, CTLA-4, CD28, CD40 and others expressed on lymphocytes and other immune cells).

The invention encompasses the administration of a VacA polypeptide, a variant or fragment thereof and pharmaceutical formulations thereof to an individual prior to, simultaneously or sequentially with other therapeutic/prophylactic/immunotherapeutic regimens or co-agents in the prevention or treatment of antigen/allergen hypersensitivity, in particular allergic disorders such as atopic asthma (e.g., combined tolerization regimen), in a therapeutically effective amount. A VacA polypeptide, a variant or fragment thereof or a pharmaceutical formulation thereof that is administered simultaneously with said co-agents can be administered in the same or different composition(s) and by the same or different route(s) of administration.

According to another aspect, the VacA polypeptides or variants or fragments thereof according to the invention may be used in an immunotherapy regimen wherein the VacA polypeptides, variants or fragments thereof according to the invention are associated with at least one antigen of a broad range of antigens (allergens). *H. pylori* extract or VacA polypeptides could be mixed and administered with house dust mite allergen, pollen-derived allergens, or any of the above listed food allergens (peanut-, milk-, soy-derived or other) or any other allergens to promote desensitization (hyposensitization) in an allergen-specific manner (Khinchi et al., 2004, *Allergy,* 59(1):45-53).

According to one embodiment, a pharmaceutical formulation is provided comprising a VacA polypeptide or a variant or fragment thereof, combined with at least one co-agent useful in the prevention and/or treatment of hypersensitivity, in particular allergic disorders such as atopic asthma, and at least one pharmaceutically acceptable carrier, diluent or excipient thereof.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a disorder selected from an allergic disorder such as allergen-induced or atopic asthma (eczema), atopic dermatitis (hay fever), atopic rhinitis, allergic conjunctivitis, food allergy, occupational allergy, allergic broncho-pulmonal aspergillosis and hypersensitivity pneumonitis.

In another embodiment, patients according to the invention are patients at risk of suffering from an allergic disorder.

In another further embodiment, patients according to the invention are suffering from allergen-induced or atopic asthma.

In another embodiment, patients according to the invention are patients at risk of suffering from a seasonal allergic disorder such as pollen allergy, including food-pollen allergy.

In another further embodiment, patients according to the invention are children or infants, for example infants before the age of about three years.

In another further embodiment, patients according to the invention are pregnant mothers with a high risk of atopy or pregnant mothers of children with a high risk of atopy, which may be treated during pregnancy.

In another further embodiment, patients according to the invention are suffering from an allergic disorder selected from atopic dermatitis, atopic rhinitis and allergic conjunctivitis.

In another further embodiment, patients according to the invention are suffering from food allergy.

Use According to the Invention

In accordance with one aspect of the present invention, a process is provided for tolerizing a subject or inducing a tolerization response in said subject to at least one antigen/allergen by use of a polypeptide, formulation or combination as herein described. The polypeptide, formulation or combination according to the invention is administered in an amount and in accordance with a dosage regimen that is effective for inducing tolerance in a subject.

In one embodiment of the invention a use of a polypeptide or a formulation thereof according to the invention is provided for the preparation of a pharmaceutical composition for the prevention, repression and/or treatment of an allergic disorder or an allergic response, in particular atopic asthma.

In another embodiment of the invention a use of a polypeptide or a formulation thereof according to the invention is provided for the preparation of a pharmaceutical composition for the repression or treatment of allergen hypersensitivity.

In another embodiment of the invention a use of a polypeptide or a formulation thereof according to the invention is provided for the preparation of a pharmaceutical composition for tolerizing a subject or inducing a tolerization response in said subject.

In another embodiment of the invention a method for tolerizing a subject or inducing a tolerization response in said subject is provided, said method comprising administering in a subject in need thereof an effective or tolerizing amount of a polypeptide or a formulation thereof according to the invention.

In another embodiment of the invention a method for preventing, repressing or treating an allergic response is provided, in particular, an allergic disorder, in particular atopic asthma, in a subject, said method comprising administering to a subject in need thereof a therapeutically effective amount a polypeptide according to the invention, a fragment or variant thereof, or a pharmaceutical formulation thereof according to the invention.

According to another embodiment of the invention, a method for treating allergen intolerance in a subject is provided, said method comprising administering sequentially or simultaneously to said subject a polypeptide according to the invention or a composition thereof and the allergen(s) or an antigenic component or fragment or analog thereof in an amount effective to induce tolerance to said allergen in said subject.

In a further embodiment of the invention a use or a method according to the invention is provided, wherein the subject is predisposed to or at risk of developing an allergic disorder, in particular atopic asthma, for example based on familial history, overweight status or age.

According to another embodiment, the invention relates to a pharmaceutical formulation comprising a polypeptide selected from a VacA protein or a fragment or variant thereof, combined with at least one co-agent useful in the prevention, repression and/or treatment of an allergic disorder, in particular atopic asthma, and/or for inducing a tolerization response to an allergen, and at least one pharmaceutically acceptable carrier, diluent or excipient thereof.

In another embodiment, a use or a method according to the invention is provided, wherein a polypeptide or a composition of the invention is to be used in combination with an allergen.

In another embodiment, a polypeptide, composition or method according to the invention is provided, wherein said polypeptide or a composition thereof is to be administered by the oral, intranasal, intrapulmonary, parenteral or systemic route.

In another embodiment, a polypeptide, composition or method according to the invention is provided, wherein VacA is s1m1 VacA.

In another embodiment, is polypeptide, composition or method according to the invention is provided, wherein VacA is s2m2 VacA.

In another embodiment, a polypeptide, composition or method according to the invention is provided, wherein VacA is a VacA protein comprising an amino acid sequence selected from SEQ ID NOs: 1, 2, 4, 5, 6, 7, 8, 9, 10 and 11.

In another embodiment, a polypeptide, composition or method according to the invention is provided, wherein VacA is a VacA protein comprising an amino acid sequence of SEQ ID NO: 1 or a fragment or variant thereof.

In another embodiment, a polypeptide, composition or method according to the invention is provided, wherein VacA is a VacA protein comprising an amino acid sequence of SEQ ID NO: 2 or a fragment or variant thereof.

In another embodiment, a medicinal kit is provided, comprising in compartmental form a first compartment or series of compartments comprising a polypeptide, a fragment or variant thereof or a composition thereof and a second compartment or series of compartments comprising an allergen or source of allergen or antigenic fragments, components or analogs thereof with instructions for use.

Examples illustrating the invention will be described hereinafter in a more detailed manner and by reference to the embodiments represented in the Figures.

EXAMPLES

The following abbreviations refer respectively to the definitions below:

BALF (bronchoalveolar lavage fluid), BCA (bicinchoninic acid assay), EDTA (ethylene-diaminetetraacetic acid), FCS (fetal calf serum), GM-CSF (granulocyte-macrophage colony-stimulating factor), H&E (hematoxylin and eosin, i.p. (intraperiotoneally), MCTP1 (mast cell protease P1), MLN (mesenteric lymph node), PAS (periodic acid-Schiff), PBS (phosphate buffered saline), RPMI (Royal Park Memorial Institute (culture medium).

Example 1: *H. pylori* Dead Cell Extract in Allergen-Induced Asthma

Figure 1:
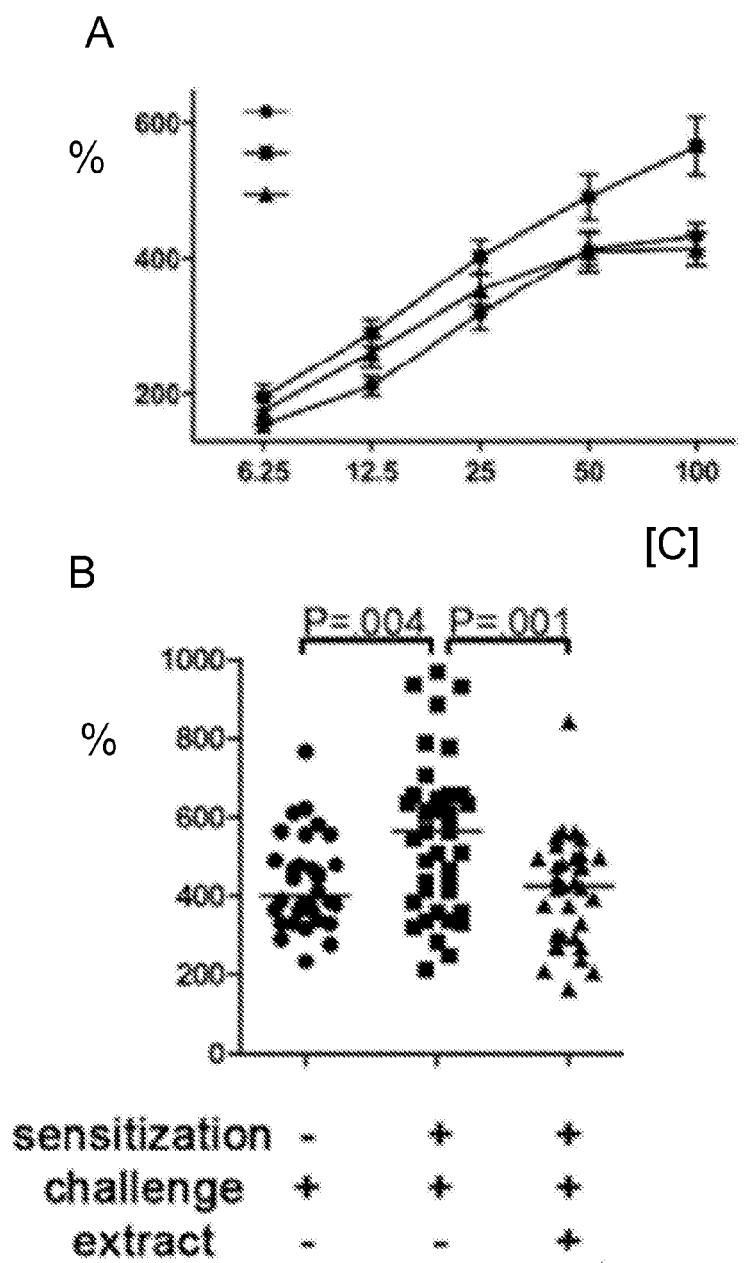
FIG. 1 shows the alleviation of experimentally induced asthma by treatment with a composition according to the invention as described in Example 1, for the group subjected to *H. pylori* extract (-▲-) as compared to positive controls (sensitized mice but no treatment) (-■-) and negative controls (mock-sensitized mice) (-•-). A, B: Airway hyperresponsiveness in response (change in % from baseline levels, which are individually determined for every mouse) to increasing doses of metacholine ([C] in mg/ml) and the highest dose of 100 mg/ml, respectively; C, D: total cells and eosinophils contained in 1 ml of BALF; E-G: tissue inflammation and goblet cell metaplasia as scored by two blinded experimenters on H&E and PAS-stained tissue sections; representative micrographs taken at 100× (H&E) and 400× (PAS); original magnifications are shown in G; pooled data from 5 independent studies are shown in A-F; H, I: IL-5 and IL-13 secretion by single cell lung preparations restimulated with ovalbumin, as assessed by ELISA as described in Example 1; pooled data from two studies are shown.
Figure 1:
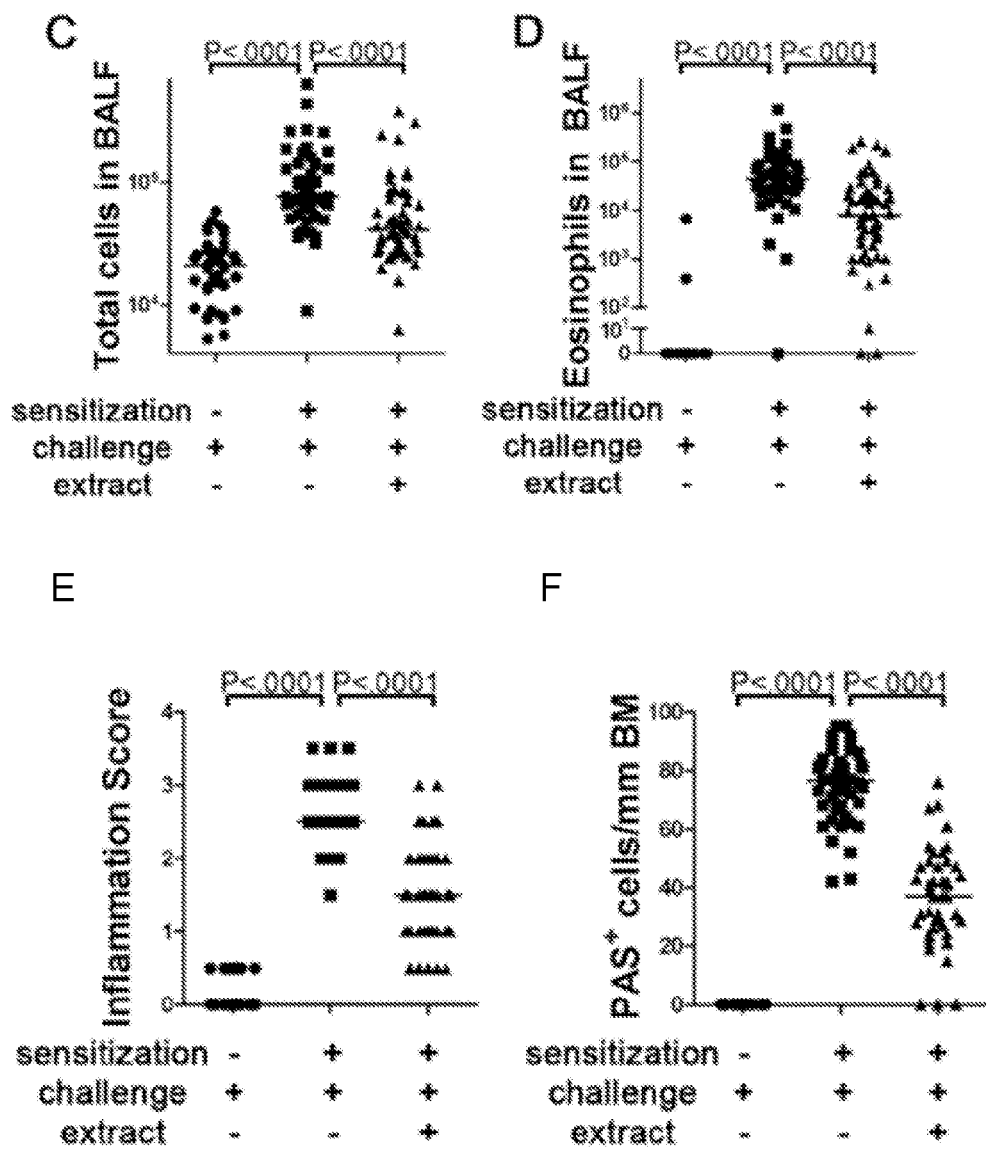
Figure 1:
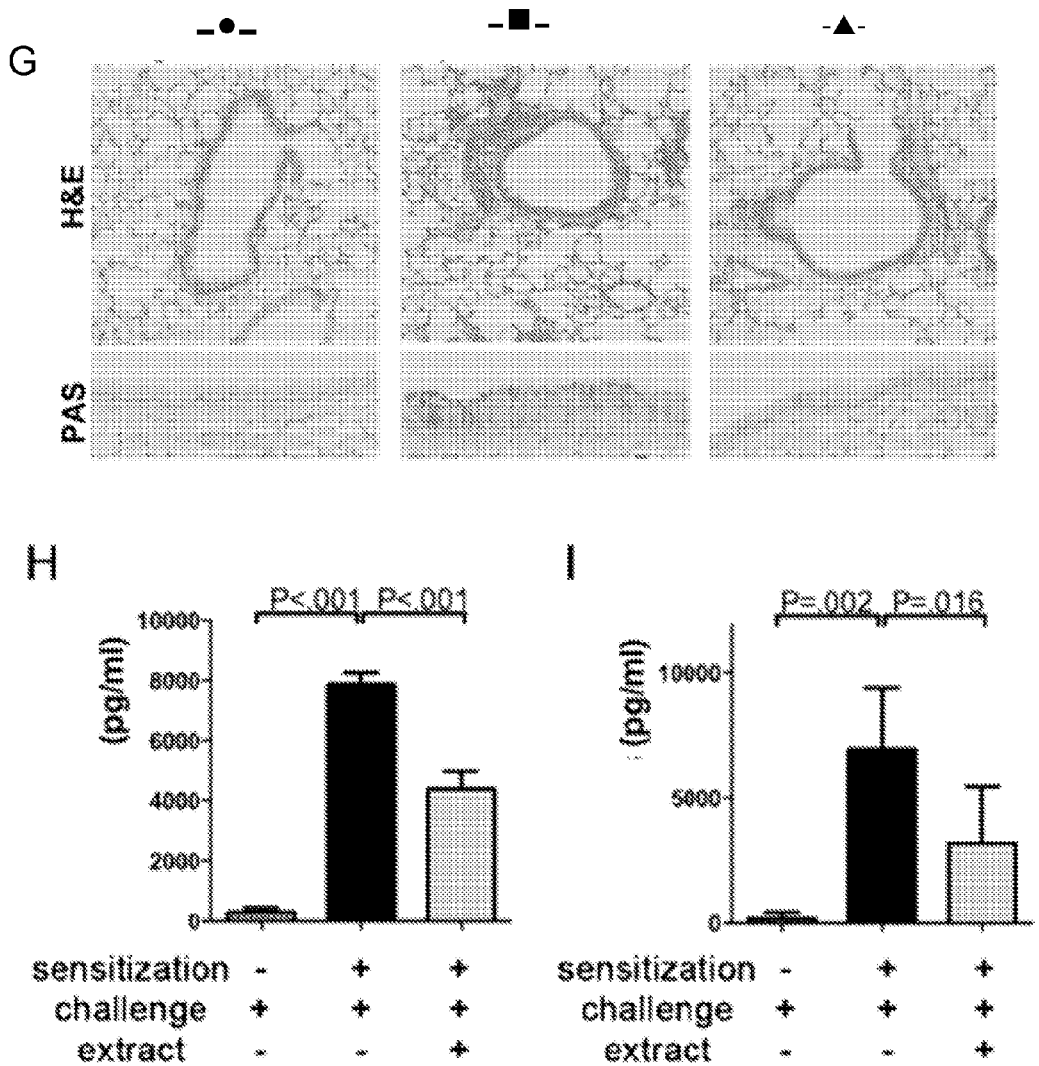

To assess whether regular administration of compositions of the invention provided in the form of an *H. pylori* dead cell extract protects against allergen-induced responses such as asthma, the following model was used: mice were administered with weekly doses intragastrically of whole dead cell extract (prepared as described below) from age 7 days onwards prior to subjecting them to ovalbumin sensitization and challenge with alum-adjuvanted ovalbumin as described below. Control mice that had received ovalbumin but no *H. pylori* dead cell extract developed airway hyper-responsiveness to methacholine (FIGS. 1A-B) and bronchoalveolar immune cell infiltration and eosinophilia as measured by staining and quantification of cells harvested by bronchoalveolar lavage (FIGS. 1C-D), as well as histologically evident lung inflammation and goblet cell metaplasia as determined by histological assessment and scoring of H&E and PAS-stained paraffin sections (FIGS. 1E-G). The re-stimulation of single cell lung preparations with ovalbumin induced the production of high levels of the Th2 cytokines IL-5 and IL-13 as measured by ELISA and cytometric bead array (following the manufacturer's instructions, R&D Biosystems; BD Biosciences) (FIGS. 1H-I). In contrast, mice that had received *H. pylori* dead cell extract were protected against airway hyper-responsiveness (FIGS. 1A-B), and exhibited significantly lower levels of bronchoalveolar and pulmonary inflammation, eosinophilia and goblet cell metaplasia (FIGS. 1C-G). Th2 cytokine production upon allergen re-stimulation of lung preparations by ELISA and cytometric bead array was also reduced (FIGS. 1H-I). The failure of dead cell extract-treated mice to develop allergen-induced symptoms of asthma was not due to an impaired primary response to the allergen, as the levels of ovalbumin-specific serum IgE as measured by ELISA were similar in all sensitized mice.

To address the specificity of the observed effects and elucidate key prerequisites of protection, various administration routes and regimens and ages at treatment onset were investigated, as well as extracts from other gastrointestinal pathogens. Interestingly, the systemic (intraperitoneal) administration of *H. pylori* dead cell extract was as efficient as the intragastric route at conferring protection against allergen-induced asthma. Intragastric treatment was less effective when initiated in adult mice as opposed to neonates. Heat-inactivated *H. pylori* extract, as well as identical amounts of extracts generated from cultures of *E. coli* or *Salmonella typhimurium*, failed to confer protection against the examined hallmarks of allergic airway disease.

In conclusion, the beneficial effects of dead cell extract treatment are specific to *H. pylori* and require a heat-sensitive component of the bacteria, and are most pronounced if the treatment is initiated in young mice.

Preparation of *H. pylori* Dead Cell Extract and Purification of GGT and VacA

*H. pylori* strain PMSS1 (Arnold et al. 2011, supra) secreting s2m2 VacA was cultured in *Brucella* broth supplemented with 10% FCS, pelleted by centrifugation and washed once with PBS. Bacteria were subjected to three freeze/thaw cycles and disrupted by three passes through a French pressure cell press (Stansted Fluid Power, Cell Pressure Homogenizer) at 30,000 bars. Cell debris were removed by centrifugation and the supernatant filtered through a 2 µm filter leading to the dead cell extracts used in the present examples. Protein concentrations were determined using the BCA Protein Kit (R&D Systems).

*H. pylori* VacA was purified from *H. pylori* culture supernatants using previously published procedures (Cover et al., 1992, *J. Biol. Chem.*, 267:10570-1057; Cover et al., 1997, *J. Cell. Biol.*, 138:759-769), with the following slight modifications. *H. pylori* strain ATCC 49503/60190, which was first described in 1990 (Cover et al., 1990, *Infect. Immun.*, 58:603-610), was cultured in sulfite-free *Brucella* broth containing either cholesterol or 0.5% charcoal. After centrifugation of the culture, supernatant proteins were precipitated with a 50% saturated solution of ammonium sulfate. The oligomeric form of VacA was isolated by gel filtration chromatography with a Superose 6 HR 16/50 column in PBS containing 0.02% sodium azide and 1 mM EDTA.

Animal Experimentation

C57BL/6 and BL/6.BATF3−/− mice (Jackson Labs) were orally infected with *H. pylori* strain PMSS1 as described (Arnold et al., 2011, supra), or received either once-weekly oral or i.p. doses of 200 µg dead cell extract (prepared as described above) of *H. pylori* wild-type PMSS1 or the mutant strain, lacking the VacA gene (PMSS1ΔvacA) (described in Oertli et al., 2013, supra), *Salmonella typhimurium*, or *E. coli* or once-weekly i.p. doses of 25 µg s1m1 type VacA (SEQ ID NO: 1) wild-type produced as explained above or the deleted variant Δ6-27 purified from *H. pylori* strain ATCC 49503/0190 of SEQ ID NO: 3 as described in Vinion-Dubiel et al., 1999, *J. Biol. Chem.*, 274:37736-37742.

Mice were sensitized by intraperitoneal injection with alum-adjuvanted ovalbumin (20 µg ovalbumin (Sigma-Aldrich) emulsified in 2.25 mg aluminum hydroxide (Alum Imject; Pierce)) at 8 and 10 weeks of age and challenged with 1% aerosolized ovalbumin using an ultrasonic nebulizer (NE-U17; Omron) for 20 min daily on days 31, 32 and 33 post-initial sensitization. Unsensitized mice served as negative controls. One group received once-weekly doses of 200 µg *H. pylori* dead extract intragastrically from day 7 of age until the second sensitization.

Airway resistance measurements were performed on anesthetized, intubated and mechanically ventilated mice and airway resistance (as measured using the FinePointe Resistance and Compliance System, Buxco Electronics) was recorded in response to increasing doses of inhaled methacholine.

In vivo blocking of IL-10 signaling as described in Example 2 was achieved by three i.p. injections of 250 µg anti-IL-10R antibody (clone 1B1.3A, BioXCell) during the challenge phase. Lungs were lavaged via the trachea with 1 ml PBS. Bronchoalveolar lavage fluid (BALF) cells were counted using trypan blue dye exclusion. Differential cell counts of macrophages, lymphocytes, neutrophils and eosinophils were performed on cyto-centrifuged preparations stained with the Microscopy Hemacolor® Set (Merck). For lung histopathology, lungs were fixed by inflation and immersion in 10% formalin and embedded in paraffin. Tissue sections were stained with H&E and periodic acid-Schiff and examined in blinded fashion on a BX40 Olympus microscope. Peribronchial inflammation was scored on a scale from 0 to 4. PAS-positive goblet cells were quantified per 1 mm of basement membrane.

Example 2: Role of Cell Extracts on IL-10 Production

*H. pylori* is known to induce the production of IL-10 in various immune cell compartments (Sayi et al., 2011, *J. Immunol.*, 186:878-890) and high gastric levels of IL-10 ensure *H. pylori* persistence and promote *H. pylori*-specific immune tolerance (Arnold et al., 2011, supra).

Figure 2:
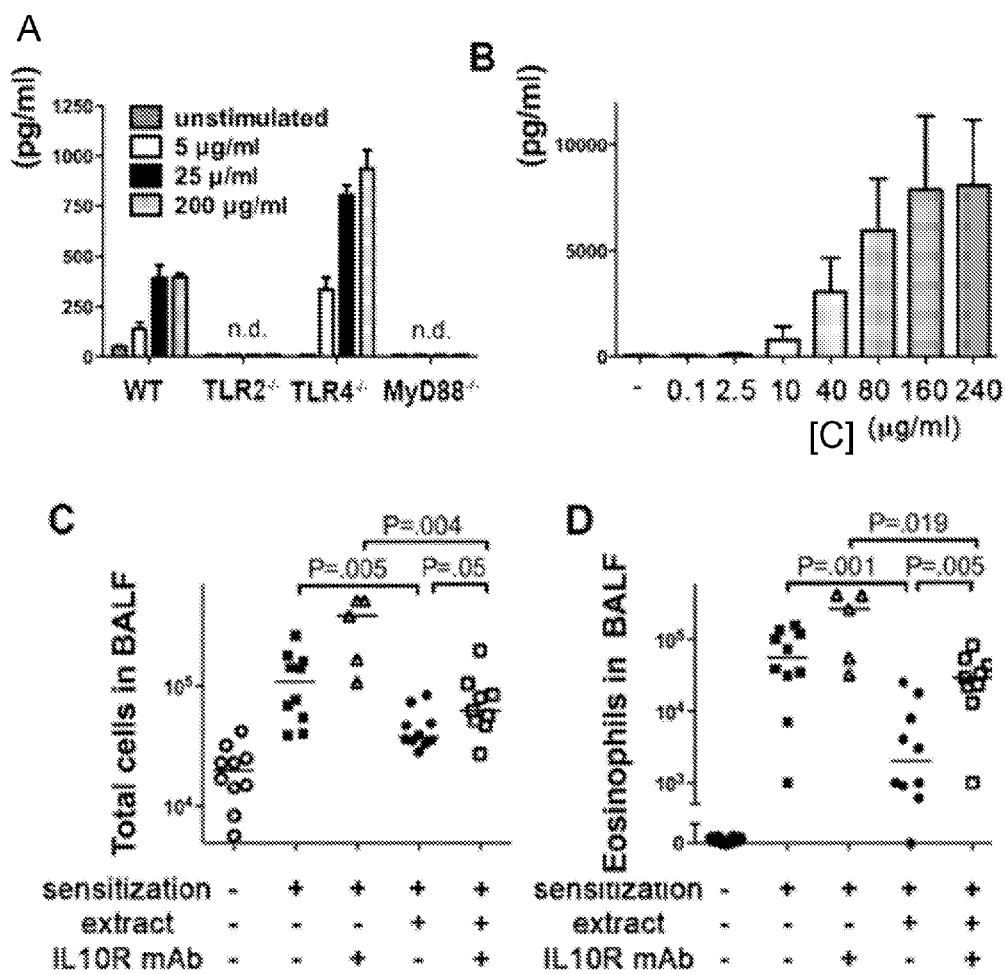
FIG. 2 shows that IL-10 signalling is required for dead cell extract-induced protection against asthma. A, B: IL-10 secretion by murine bone-marrow-derived DCs and human monocyte-derived DCs from six healthy volunteers after exposure to the indicated amounts of *H. pylori* dead cell extract ([C]) of the invention as described in Example 2. A: one representative experiment of three; B: pooled data for all six donors is shown in B; C-F: mice treated as described in FIG. 1; the indicated groups received 3 doses of anti-IL-10R antibody during the challenge phase of the protocol as described in Example 2; C, D: total cells and eosinophils contained in 1 ml of BALF; E, F: tissue inflammation and goblet cell metaplasia. In scatter plots, each symbol represents one mouse; horizontal lines indicate the medians.
Figure 2:
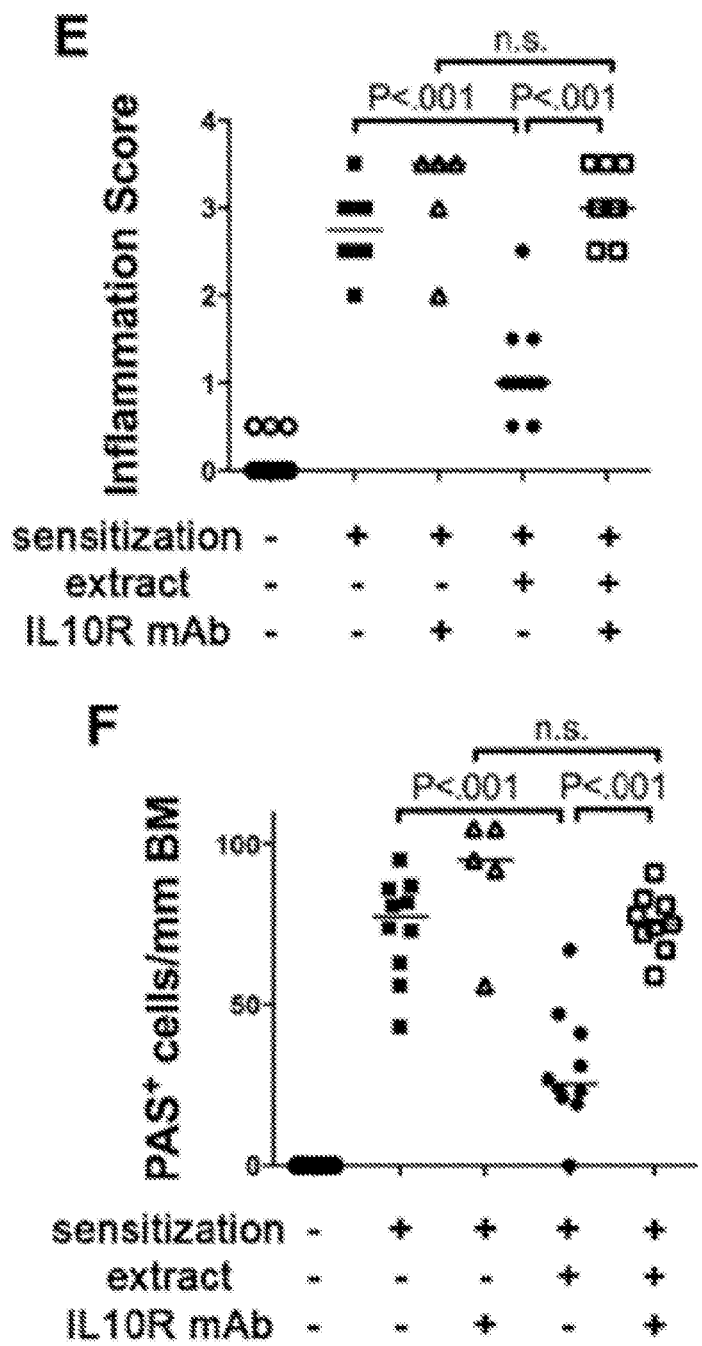
Figure 3:
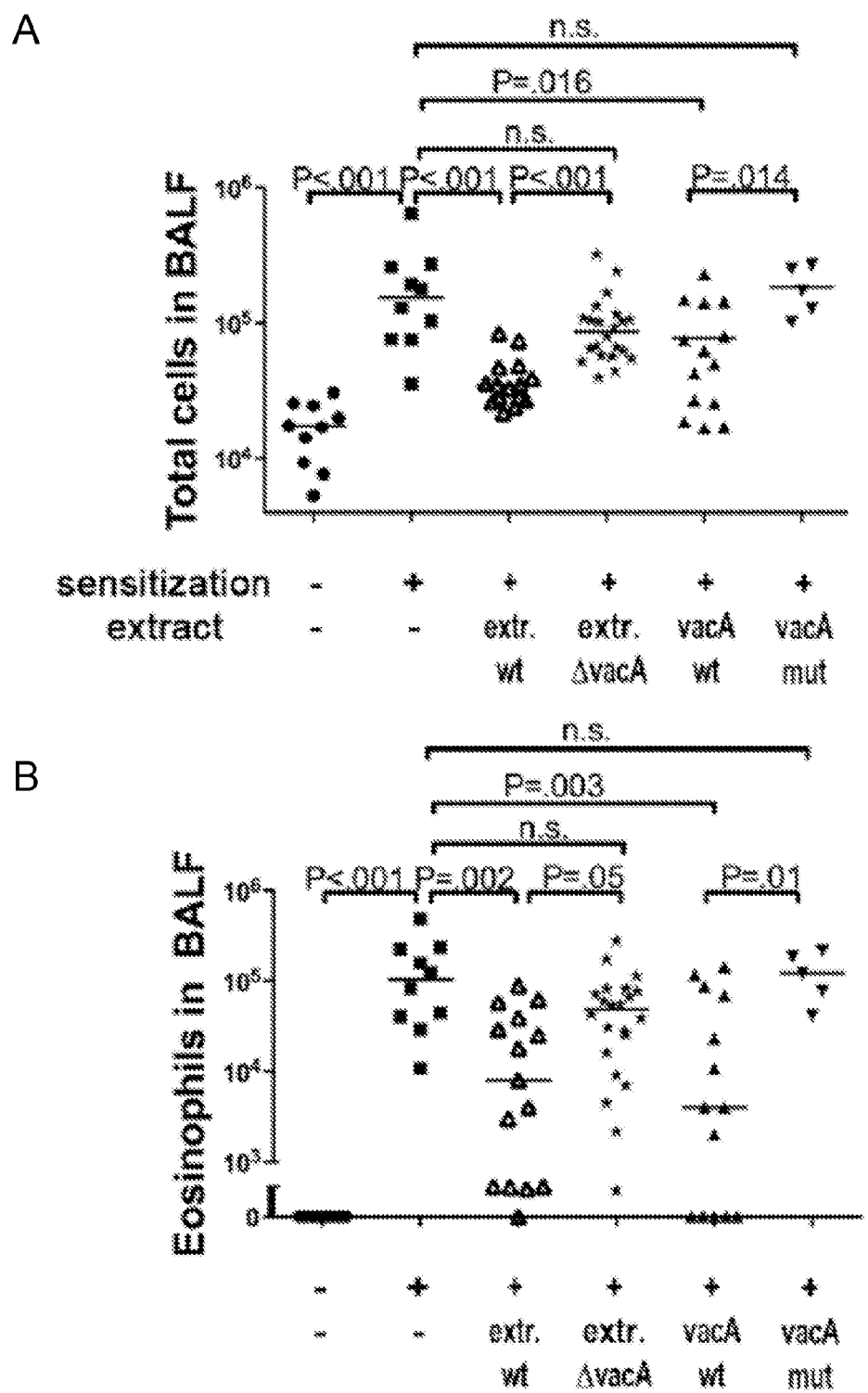
FIG. 3 shows that VacA is both required and sufficient for protection against allergic airway disease in the model of allergen-induced asthma. Extract from an *H. pylori* mutant lacking the VacA gene ("extr. ΔvacA") was consistently less efficient than wild-type extract ("extr. wt") at protecting allergen-sensitized and -challenged mice against bronchoalveolar and pulmonary inflammation, eosinophilia and goblet cell metaplasia (FIG. 3A-D). To examine whether VacA alone is sufficient to provide protection, oligomeric VacA purified from culture supernatants of *H. pylori*, as described in Example 1, was intraperitoneally administered, once weekly from day 7 of age onwards. No adverse effects were observed in any of the mice, despite their young age at the time of the first doses. Strikingly, VacA provided a level of protection against asthma that was comparable to the protection conferred by extract treatment (FIG. 3A-D). A negative control VacA protein lacking an amino-terminal hydrophobic region of three tandem repeats that have been described as being essential for VacA's cytotoxic activity (Vinion-Dubiel et al., 1999, supra), i.e., of SEQ ID NO: 3 (FIG. 5), failed to protect against asthma (FIGS. 3A-D).

In order to assess whether DCs produce IL-10 in response to *H. pylori* dead extract, cultured murine bone marrow-derived (BM) DCs were treated with increasing concentrations of dead cell extract prepared as described above. Indeed, BM-DCs produced and secreted large amounts of IL-10, and this was dependent on TLR2 and MyD88 signalling (FIG. 2A). A clear dose-dependent secretion of IL-10 could also be observed in human blood-derived DCs from six independent donors cultured with *H. pylori* dead cell extract (FIG. 2B). To address whether IL-10 is required for asthma protection conferred by dead extract tolerization, two doses of IL-10 receptor (IL-10R)-neutralizing antibody were administered during the challenge phase of the protocol to mice that had received dead cell extract from the neonatal period onwards and it was shown that IL-10 signalling was required for protection against asthma (FIGS. 2C-F).

In summary, *H. pylori* dead cell extracts are able to induce IL-10 production in both murine and human DCs and the beneficial effects of dead cell extract treatment in allergic asthma depend on the IL-10 signaling proficiency of the host.

Preparation of Murine and Human DCs and IL-10 ELISA

For generation of murine BM-DCs, bone marrow isolated from the hind legs of donor mice (BL/6.TLR2$^{-/-}$, BL/6.TLR4$^{-/-}$, and BL/6.MyD88$^{-/-}$ mice, all from Jackson Labs) was seeded at 50,000 cells per well in 96-well plates in RPMI/10% FCS and 4 ng/ml GM-CSF and cultured for 5 days. DCs were stimulated with the indicated amounts of *H. pylori* PMSS1 extract prepared as described above for 16 h and supernatants were subjected to mIL-10 ELISA (BD Pharmingen). Human monocyte-derived dendritic cells were generated from peripheral blood mononuclear cells as follows. Venous blood was drawn from 6 healthy volunteers according to protocols approved by the Institutional Review Board of Leiden University Medical Center. Cells were collected after density gradient centrifugation on Ficoll and CD14+ monocytes were positively isolated by magnetic-activated cell sorting (MACS) using CD14 microbeads (Miltenyi Biotec). Cells were cultured in RPMI-1640 (Invitrogen) supplemented with penicillin (100 U/ml, Astellas Pharma), streptomycin (100 µg/ml, Sigma), pyruvate (1 mM, Sigma), glutamate (2 mM, Sigma), 10% fetal calf serum (FCS), 20 ng/ml human recombinant granulocyte-macrophage colony-stimulating factor (rGM-CSF, Invitrogen/Life Technologies), and 0.86 ng/ml human rIL-4 (R&D Systems) for 6 days. On day 3, the medium and the supplements were refreshed. Monocyte-derived DCs were stimulated with *H. pylori* dead cell extract for 48 hours. Secretion of IL-10 by the DCs in the supernatant was measured by ELISA (Sanquin).

The differential susceptibility to successful tolerization of neonates and adults may be attributable to the general tolerogenic bias of the immature neonatal immune system, with its higher Treg/Teffector cell ratios and Treg-predominant responses to foreign antigens (Arnold et al., 2005, *Trends Immunol.*, 26:406-411). Parallel observations have been reported in humans: *H. pylori*-infected children, but not adults, are characterized by Treg-predominant gastric *H. pylori*-specific T-cell responses (Harris et al., 2008, *Gastroenterology*, 134:491-4). Children benefit more from harboring *H. pylori* than adults in terms of their asthma risk (Chen et al., 2007, *Arch. Intern. Med.*, 167:821-827); similarly, early onset asthma in adolescents and young adults is more strongly inversely correlated with *H. pylori* seropositivity than adult-onset asthma (Chen et al, 2008, *J. Infect. Dis.*, 198:553-560). The available epidemiological and experimental data thus suggest that childhood acquisition of *H. pylori*, and the Treg-predominant immune responses associated with early-life acquisition, mediate the reduced risks of asthma and other allergic disease manifestations by suppressing allergen-specific T-cell responses.

The data presented here imply that children at high risk of developing asthma are more likely than adults to benefit from tolerization strategies of the invention.

Example 3: Role of VacA Polypeptide and Truncated Variant Thereof in Purified Form from the Invention In order to support that VacA in the form of a purified polypeptide might contribute alone to asthma protection conferred by extract tolerization, the protective properties of bacterial extracts (prepared as described above) from wild-type bacteria and VacA$^-$ deficient isogenic mutants (as described above) were compared. Interestingly, mutant extracts were consistently less efficient than wild-type extracts at protecting allergen-sensitized and -challenged mice against bronchoalveolar and pulmonary inflammation, eosinophilia and goblet cell metaplasia (FIGS. 3A-D). To examine whether VacA alone is sufficient to provide protection, oligomeric VacA purified from culture supernatants of *H. pylori* as described above was intraperitoneally administered, once weekly from day 7 of age onwards. No adverse effects were observed in any of the mice, despite their young age at the time of the first doses. Strikingly, VacA provided a level of protection against asthma that was comparable to the protection conferred by extract treatment (FIGS. 3A-D).

A negative control VacA deleted protein lacking an amino-terminal hydrophobic region of three tandem that are described as being essential for VacA's cytotoxic activity (Vinion-Dubiel et al., 1999, supra), i.e., of SEQ ID NO: 3 (FIG. 5), fails to protect against asthma (FIGS. 3A-D).

Figure 4:
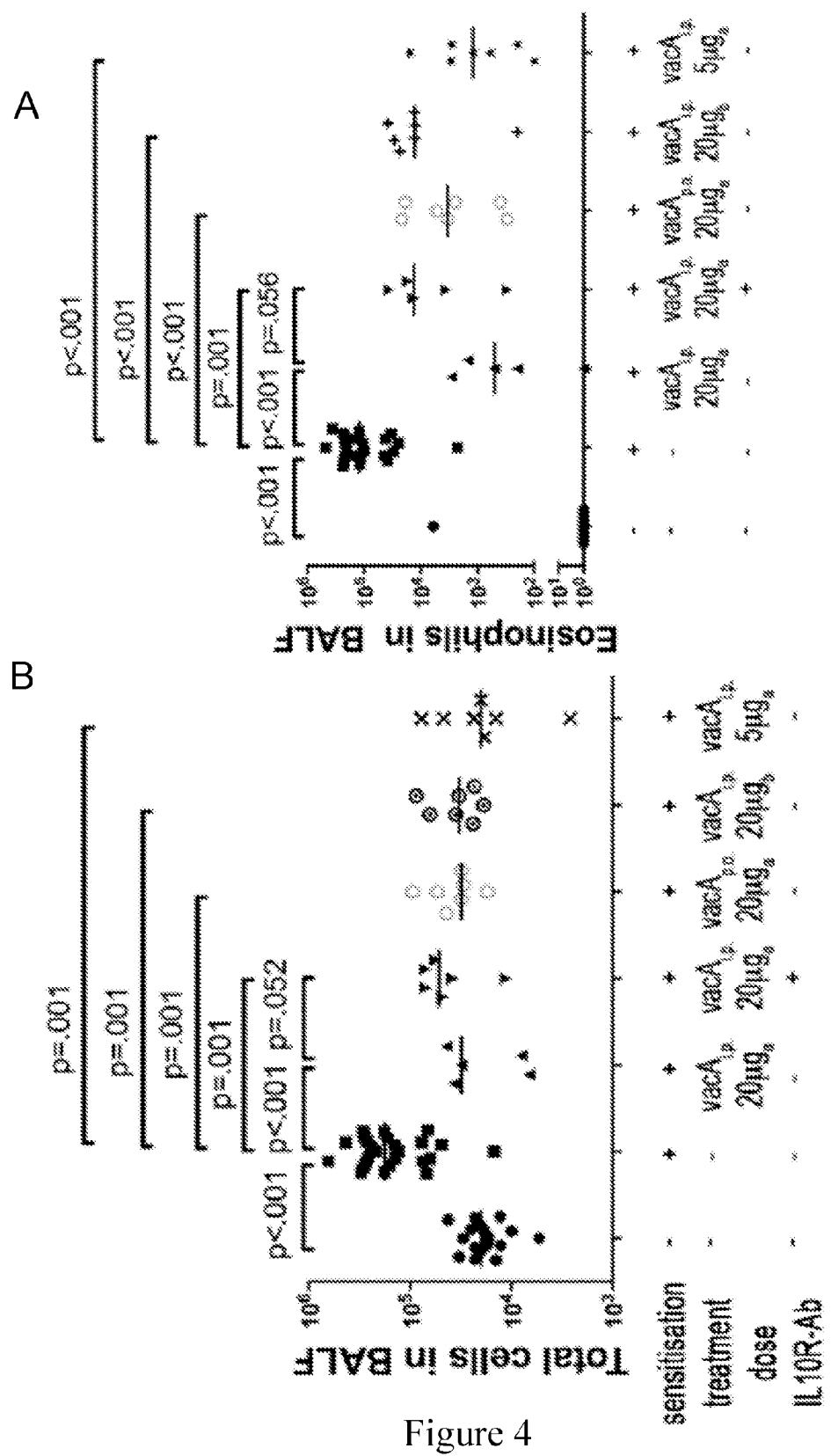
FIG. 4 shows the beneficial effects of various concentrations, delivery routes and dosing regimens of purified VacA in allergic asthma. VacA that was prepared as described above was either administered intraperitoneally or intragastrically at various concentrations and intervals in mice. 5 µg of VacA administered intraperitoneally in weekly intervals from age 7 days onwards until 2 weeks before challenge (as indicated by subscript "a") was as effective as 20 µg of VacA at preventing bronchoalveolar inflammation and eosinophilia (FIGS. 4A-B). Intragastrically (perorally, p.o.) administered VacA (again delivered weekly from day 7 until 2 weeks before challenge) also provided significant protection (FIGS. 4A-B). Three doses of intraperitoneally delivered VacA (delivered in weeks 1, 2 and 3 of life, denoted by subscript "b" in FIG. 4) were insufficient to provide full protection (FIGS. 4A-B). Blocking IL-10 signaling with two doses of a neutralizing antibody delivered intraperitoneally during ovalbumin challenge abrogated protection (FIGS. 4A-B).

Example 4: Role of VacA Polypeptide in Purified Form from the Invention at Various Concentrations and Delivery Routes In order to elucidate the minimal effective dose, number of required doses and optimal delivery route, purified VacA prepared as described above was administered either intraperitoneally or intragastrically at various concentrations and intervals in mice as described above. 5 µg of VacA administered intraperitoneally at weekly intervals from day 7 of age onwards until 2 weeks before challenge (as indicated by subscript "a" in FIG. 4) was as effective as 20 µg of VacA at preventing bronchoalveolar inflammation and eosinophilia (FIGS. 4A-B). Intragastrically (perorally, p.o.) administered VacA (again delivered weekly from day 7 until 2 weeks before challenge) also provided significant protection (FIGS. 4A-B). Three doses of intraperitoneally delivered VacA (delivered in weeks 1, 2 and 3 of life, denoted by subscript "b" in FIG. 4) were insufficient to provide full protection (FIGS. 4A-B). Blocking IL-10 signaling with two doses of a neutralizing antibody delivered intraperitoneally during ovalbumin challenge abrogated protection (FIGS. 4A-B).

Those data support that, unexpectedly, the administration of VacA alone in purified form is able to induce asthma protection comparable to the whole cell extract and therefore may be administered in purified form to prevent allergic asthma.

These findings are particularly unexpected as it was believed that only live *H. pylori* extracts would exhibit the ability to induce Tregs and that VacA alone was not expected to be sufficient for asthma protection, since, in particular, mutants lacking the ggt gene have been observed to be incapable of colonizing mice persistently and this phenotype has been attributed to DC tolerization by GGT in vitro and in vivo (Oertli et al., 2013, supra).

Altogether those data show that asthma protection of compositions of the invention was highly specific and was not conferred by extracts from other gram-negative enteropathogens such as *E. coli* or *Salmonella typhimurium*. The treatment was particularly successful when initiated in young mice relative to adult mice. Therefore, VacA and compositions thereof can be exploited for therapeutic purposes as a viable tolerization strategy for asthma prevention and treatment in high-risk individuals.

Example 5: Role of *H. pylori* Dead Cell Extract and of VacA Polypeptide of the Invention in Purified Form in a Preclinical Model of Food Allergy In order to assess the protective effect of *H. pylori* whole cell extract or purified VacA on the development of food allergy, mice were sensitized with two intraperitoneal doses of alum-adjuvanted ovalbumin prior to intragastric injection of ovalbumin as described below. Symptoms of food allergy were measured by clinical scoring and in serum by mast cell protease ELISA and ovalbumin-specific IgE and IgG1 ELISA. Th2 cytokines were quantified in ovalbumin-restimulated MLN or spleen single cell cultures.

Mice were sensitized twice i.p. at 2 weekly intervals with alum-adjuvanted ovalbumin and challenged with intragastrically delivered ovalbumin on three consecutive days starting 2 weeks after the last sensitization. One group of mice received once-weekly doses of 200 µg *H. pylori* strain PMSS1 wild-type extract intragastrically from day 7 of age onwards ("extract p.o."). Another group received once-weekly doses of 20 µg of purified HpVacA from *H. pylori* strain ATCC 49503/60190. All mice were observed for 40 min after the last challenge and scored with respect to scratching, puffiness of the eyes, mouth and nose and other symptoms of anaphylaxis such as described in Sun et al., 2007, *J. Immunol.*, 179:6696-6703. The obtained scores are represented in FIG. 6A. Ovalbumin-specific IgE and IgG1 and the mast cell protease MCPT1 were quantified in serum by ELISA and the corresponding levels are represented in FIGS. 6B-D. Splenocytes were restimulated with the above allergen for three days and the production and secretion of the Th2 cytokines IL-5 and IL-13 was measured by ELISA and the corresponding levels are represented in FIGS. 6E-F. MCPT1 data are normalized to the negative controls. Pooled data from three studies are shown for all groups except for the VacA-treated group.

Altogether, those data obtained in a food allergy model strongly suggest protective effects of *H. pylori* extract as well as VacA protein treatment.

The invention claimed is:

1. A method of preventing, repressing or treating an allergic response or an allergic disorder in a subject, said method comprising administering to a subject in need thereof, a therapeutically effective amount of a polypeptide consisting of a sequence of a VacA protein selected from SEQ ID NO: 1, 2, 4, 5, 6, 7, 8, 9, 10 or 11 or a sequence at least 90% homologous with the sequence of a VacA protein selected from SEQ ID NO: 1, 2, 4, 5, 6, 7, 8, 9, 10 or 11 or a composition thereof.

2. The method according to claim 1, wherein the polypeptide is isolated from dead *H. pylori* bacterial cell extract.

3. The method according to claim 2, wherein the *H. pylori* bacterial cell extract is from the *H. pylori* bacterial strain of ATCC 49503/60190.

4. The method according to claim 1, wherein said polypeptide is purified from an extract of non-denatured killed *H. pylori* bacterial cells.

5. The method according to claim 2, wherein the dead *H. pylori* bacterial cell extract is obtained by a process comprising the steps of:
   (i) harvesting a culture of living bacterial cells;
   (ii) submitting the harvested bacteria to several freeze/thaw cycles in water or an aqueous solution of a salt;
   (iii) disrupting the bacterial cells under high pressure; and
   (iv) collecting the cell extract.

6. The method according to claim 1, wherein said polypeptide is a recombinant VacA protein.

7. The method according to claim 1, wherein administering the polypeptide induces a tolerization response to an allergen in the subject.

8. The method according to claim 1, comprising administering the polypeptide in a form essentially free from any other *H. pylori* antigen component.

9. The method according to claim 1, wherein the allergic disorder is atopic asthma.

10. The method according to claim 1, wherein the allergic disorder is a food allergy.

11. The method according to claim 1, comprising administering the polypeptide or the composition thereof by an oral, intranasal, parenteral, intrapulmonary or systemic route.

12. The method according to claim 1, wherein the composition of the polypeptide is a pharmaceutical tolerogenic composition comprising a VacA protein consisting of a sequence selected from SEQ ID NO: 1, 2, 4, 5, 6, 7, 8, 9, 10 or 11 or a sequence at least 90% homologous with a VacA protein selected from SEQ ID NO: 1, 2, 4, 5, 6, 7, 8, 9, 10 or 11 and at least one pharmaceutically acceptable carrier, diluent or excipient thereof, essentially free from other *H. pylori* antigen components.

13. A pharmaceutical tolerogenic composition comprising a Vac A protein consisting of a sequence selected from SEQ ID NO: 1, 2, 4, 5, 6, 7, 8, 9, 10 or 11 or a sequence at least 90% homologous with a VacA protein selected from SEQ ID NO: 1, 2, 4, 5, 6, 7, 8, 9, 10 or 11 and at least one pharmaceutically acceptable carrier, diluent or excipient thereof, wherein said composition induces a tolerization response to an allergen and is essentially free from other *H. pylori* antigen components, and further comprises at least one co-agent useful in the prevention and/or treatment of an allergic disorder or an allergic response or inducing a tolerization response to an allergen.

14. The pharmaceutical tolerogenic composition according to claim 13, wherein said composition is an oral pharmaceutical composition.

15. The pharmaceutical tolerogenic composition according to claim 13, wherein said composition is an injectable pharmaceutical composition.

16. A pharmaceutical tolerogenic composition comprising a VacA protein consisting of a sequence selected from SEQ ID NO: 1, 2, 4, 5, 6, 7, 8, 9, 10 or 11 or a sequence at least 90% homologous with a VacA protein selected from SEQ ID NO: 1, 2, 4, 5, 6, 7, 8, 9, 10 or 11 and at least one pharmaceutically acceptable carrier, diluent or excipient thereof, wherein said composition induces a tolerization response to an allergen and is essentially free from other *H. pylori* antigen components and further comprises an allergen.

17. The pharmaceutical tolerogenic composition according to claim 16, wherein the allergen is at least one food allergen or a mixture thereof.

18. The method of claim 1, wherein the composition of the polypeptide is a pharmaceutical composition comprising the polypeptide and a pharmaceutically acceptable carrier, diluent or excipient.

* * * * *